(12) United States Patent
Sauer

(10) Patent No.: US 10,799,227 B2
(45) Date of Patent: Oct. 13, 2020

(54) MINIMALLY INVASIVE SURGICAL SUTURING DEVICE WITH IMPROVED VISUALIZATION

(71) Applicant: LSI Solutions, Inc., Victor, NY (US)

(72) Inventor: Jude S. Sauer, Pittsford, NY (US)

(73) Assignee: LSI Solutions, Inc., Victor, NY (US)

( * ) Notice: Subject to any disclaimer, the term of this patent is extended or adjusted under 35 U.S.C. 154(b) by 312 days.

(21) Appl. No.: 15/536,493

(22) PCT Filed: Dec. 15, 2015

(86) PCT No.: PCT/US2015/065828
§ 371 (c)(1),
(2) Date: Jun. 15, 2017

(87) PCT Pub. No.: WO2016/100348
PCT Pub. Date: Jun. 23, 2016

(65) Prior Publication Data
US 2017/0360430 A1    Dec. 21, 2017

Related U.S. Application Data

(60) Provisional application No. 62/092,222, filed on Dec. 15, 2014.

(51) Int. Cl.
*A61B 17/04*    (2006.01)
*A61B 17/02*    (2006.01)
(Continued)

(52) U.S. Cl.
CPC ...... *A61B 17/0206* (2013.01); *A61B 17/0469* (2013.01); *A61B 17/0482* (2013.01);
(Continued)

(58) Field of Classification Search
CPC ............ A61B 17/0206; A61B 17/0469; A61B 17/0482; A61B 2017/00685;
(Continued)

(56) References Cited

U.S. PATENT DOCUMENTS 5,431,666 A    7/1995 Sauer
5,562,686 A    10/1996 Sauer
(Continued)

OTHER PUBLICATIONS

Jun. 29, 2017; International Preliminary Report on Patentability for PCT/US2015/065828.

*Primary Examiner* — George J Ulsh
*Assistant Examiner* — Andrew P. Restaino
(74) *Attorney, Agent, or Firm* — David J. Gervasi; Christopher B. Miller

(57) ABSTRACT

A suturing device is disclosed. The suturing device has a guide tip. The guide tip has first and second framing arms that define a viewing port from a first orientation. The guide tip also has proximal and distal ends of the guide tip which, with the first and second framing arms, define a tissue bite area from a second orientation. The suturing device also has a ferrule holder located in the distal end of the guide tip and centered relative to the first orientation. The suturing device further has a needle movable within the guide tip along a path through the tissue bite area and centrally viewable in the viewing port relative to the first orientation.

18 Claims, 61 Drawing Sheets

(51) Int. Cl.
  *A61B 17/00* (2006.01)
  *A61B 17/34* (2006.01)

(52) U.S. Cl.
  CPC ............ *A61B 2017/00685* (2013.01); *A61B 2017/00862* (2013.01); *A61B 2017/0237* (2013.01); *A61B 2017/3427* (2013.01)

(58) Field of Classification Search
  CPC .. A61B 2017/3427; A61B 2017/00862; A61B 2017/0237; A61B 2017/06042; A61B 17/0625; A61B 17/0483; A61B 17/0057; A61B 17/06066; A61B 17/062; A61B 17/06004; A61B 17/06061; A61B 17/06166; A61B 2017/06014; A61B 2017/06052; A61B 17/06
  USPC ........................................................ 606/144
  See application file for complete search history.

(56) References Cited

U.S. PATENT DOCUMENTS

| | | |
|---|---|---|
| 6,997,931 B2 | 2/2006 | Sauer |
| 7,211,093 B2 | 5/2007 | Sauer |
| 7,407,505 B2 | 8/2008 | Sauer |
| 7,731,727 B2 | 6/2010 | Sauer |
| 8,313,796 B2 | 11/2012 | Sauer |
| 2002/0193809 A1 | 12/2002 | Meade |
| 2003/0065338 A1* | 4/2003 | Takamoto .......... A61B 17/0469 606/144 |
| 2007/0255296 A1* | 11/2007 | Sauer ................. A61B 17/0057 606/144 |
| 2010/0211083 A1 | 8/2010 | Sauer |
| 2011/0118758 A1* | 5/2011 | Sauer ................. A61B 17/0469 606/144 |
| 2011/0276064 A1* | 11/2011 | Henrichsen ........ A61B 17/0469 606/145 |
| 2015/0359531 A1* | 12/2015 | Sauer ................. A61B 17/0482 606/148 |

\* cited by examiner

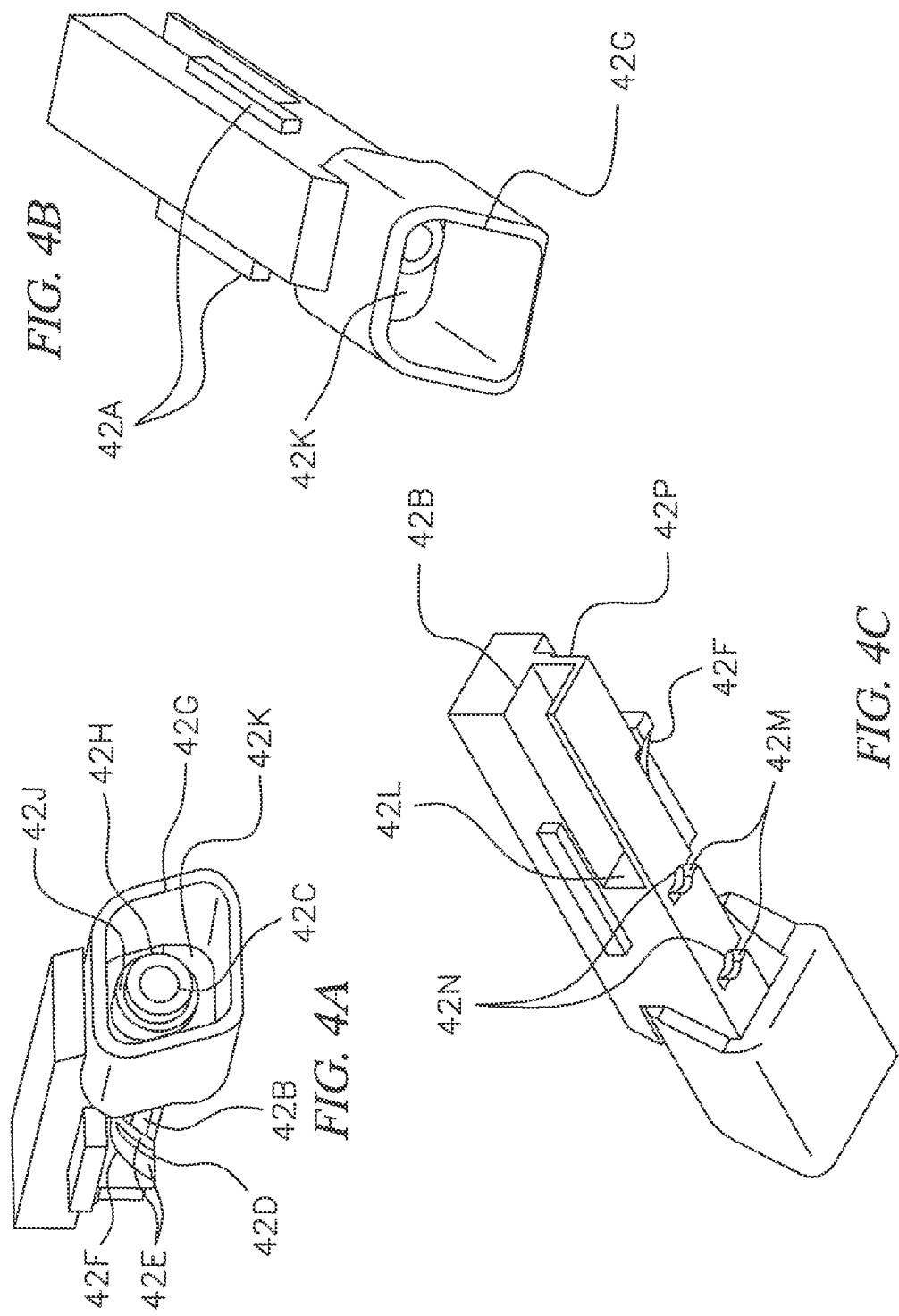

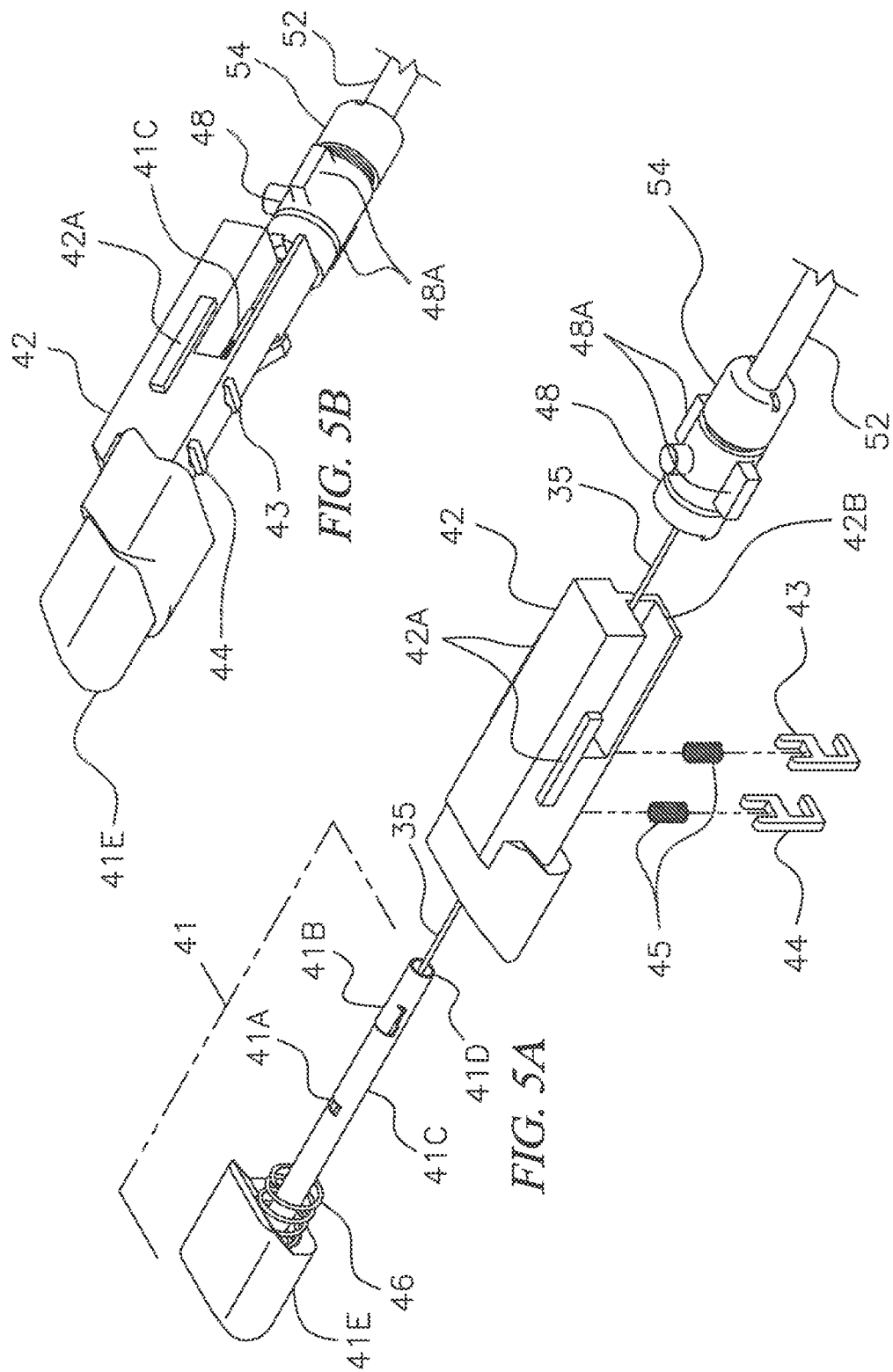

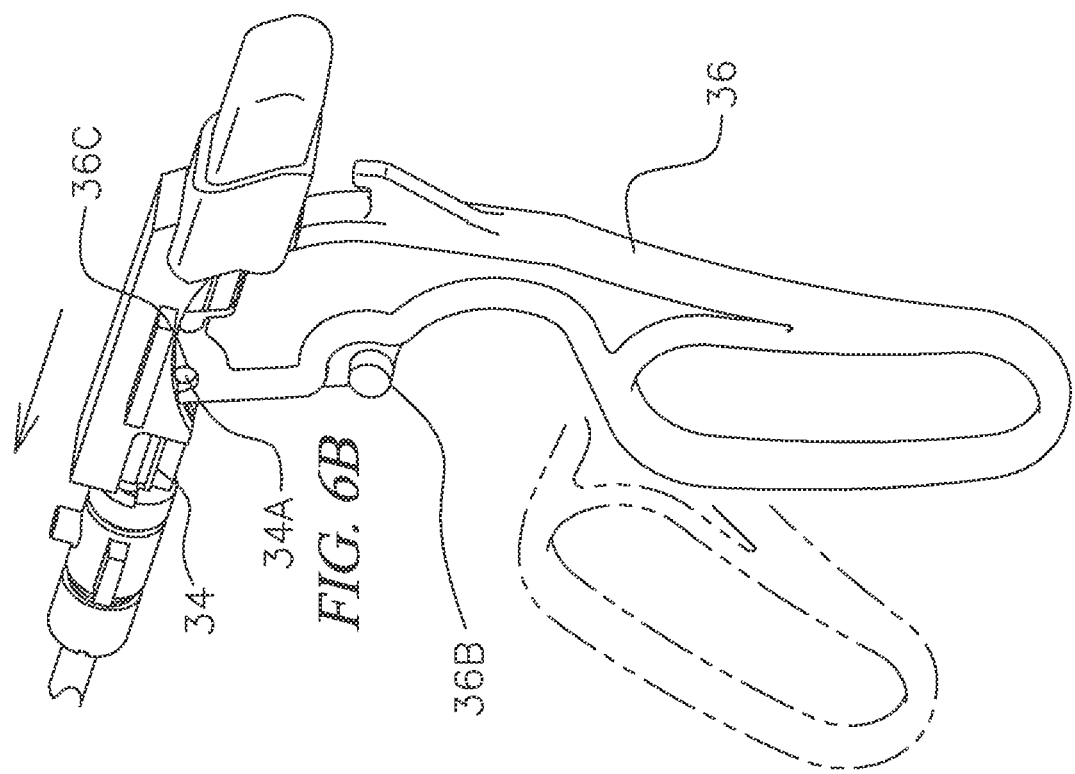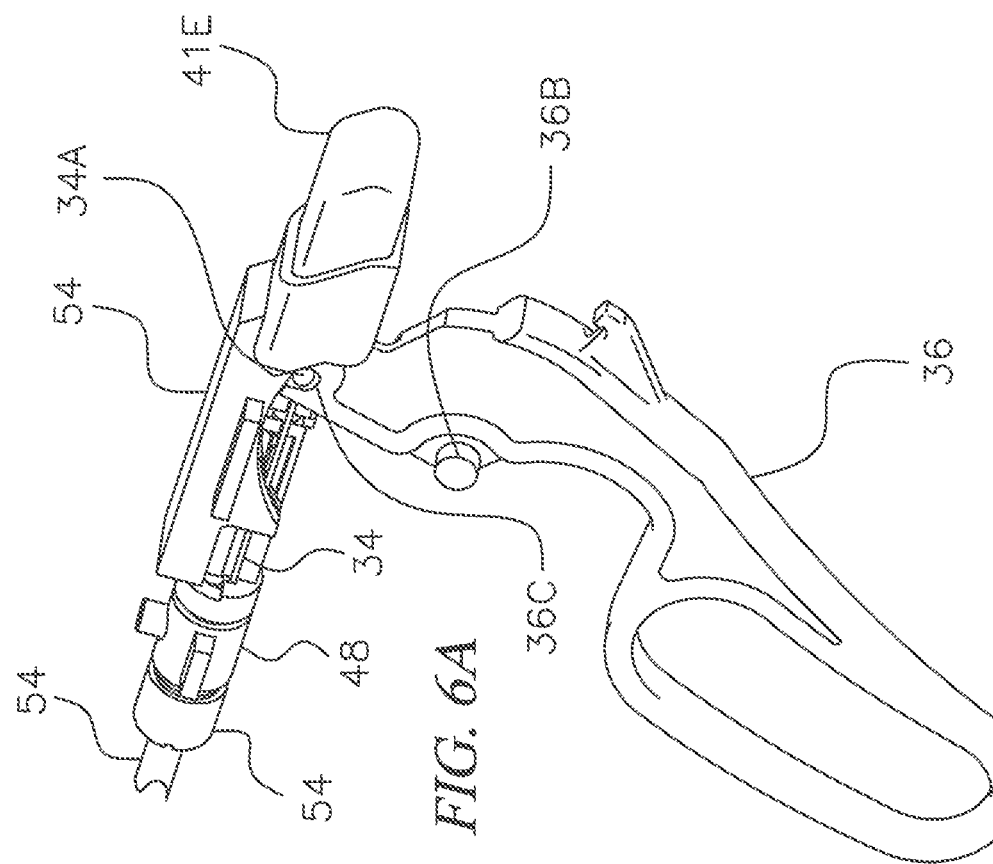

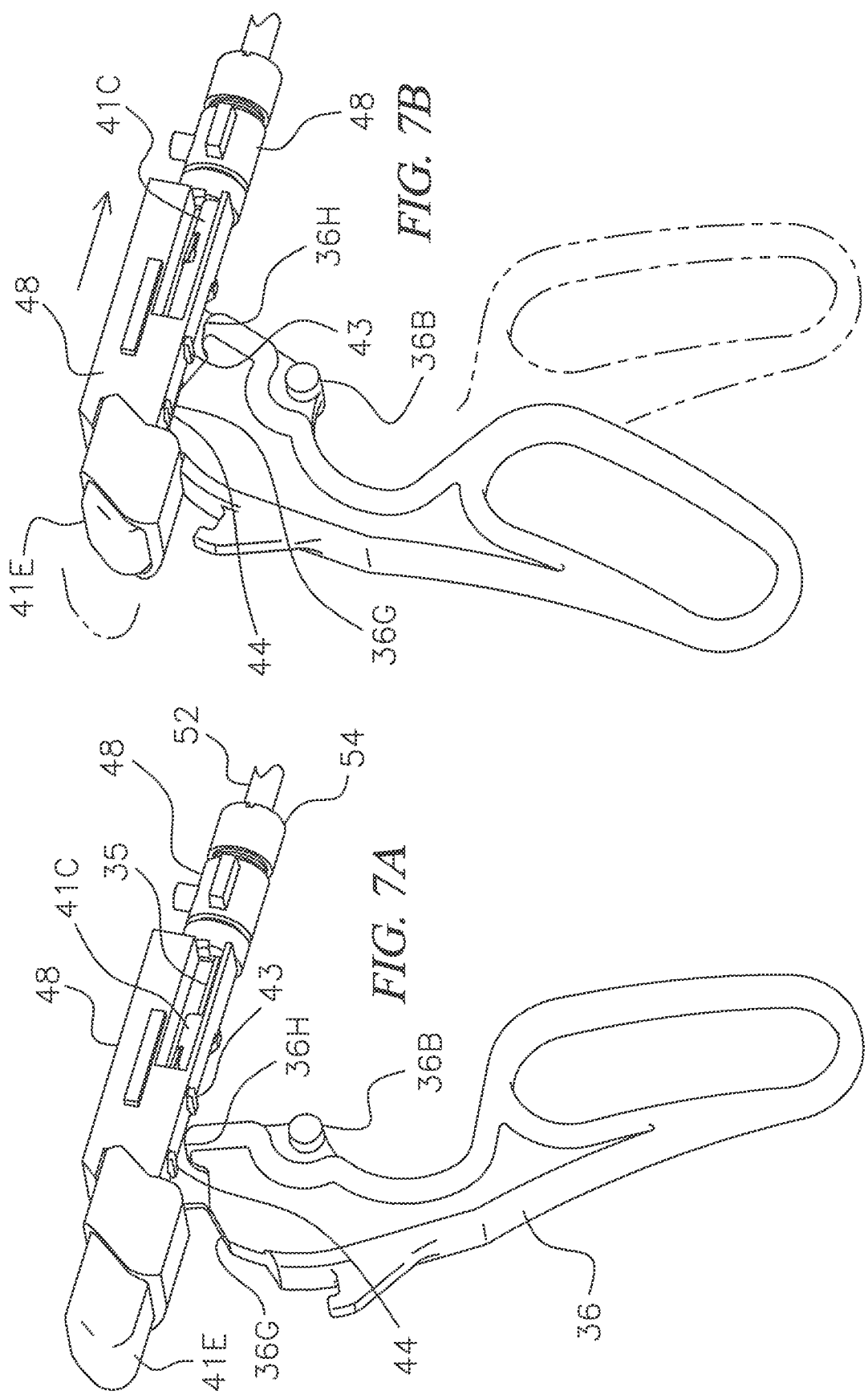

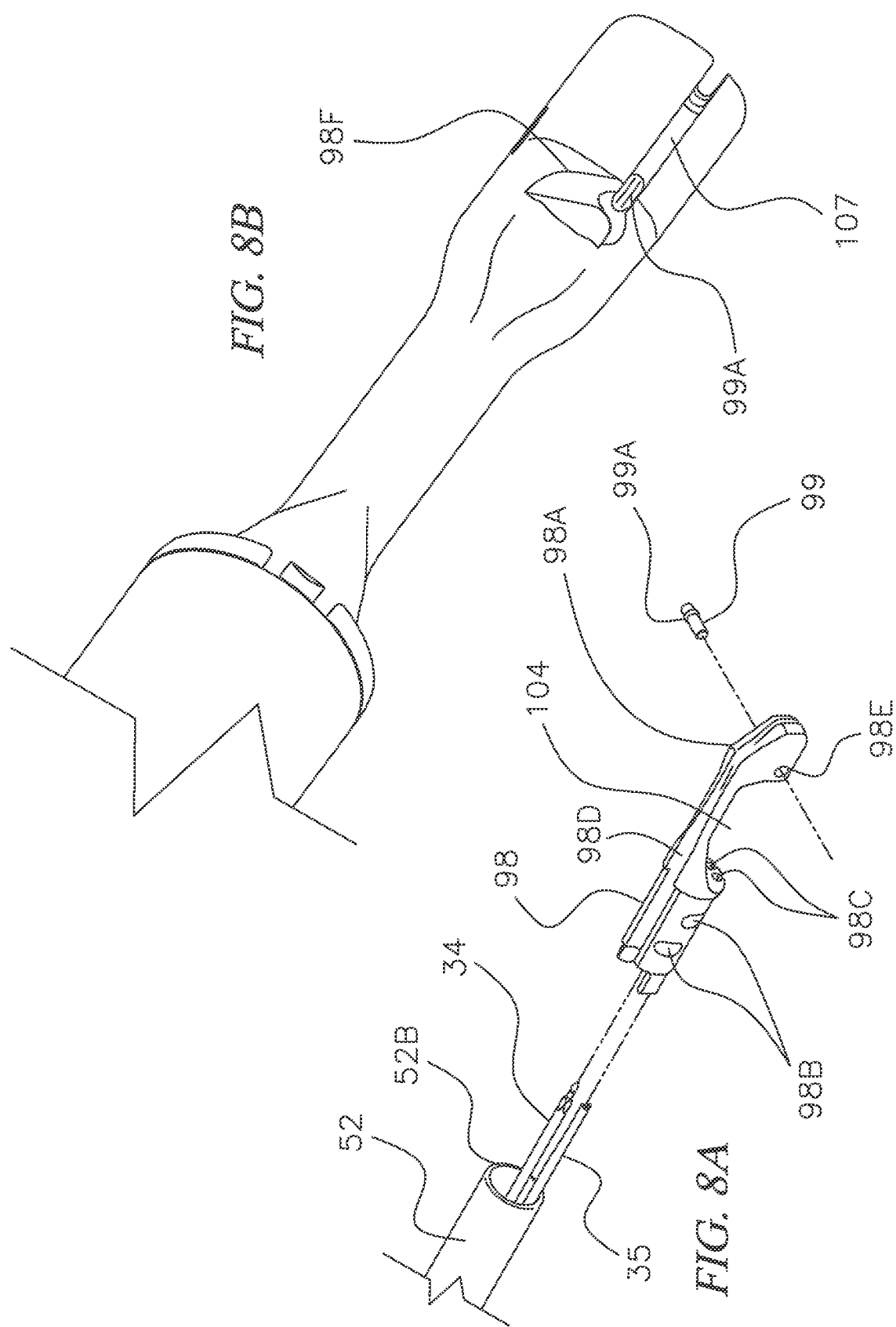

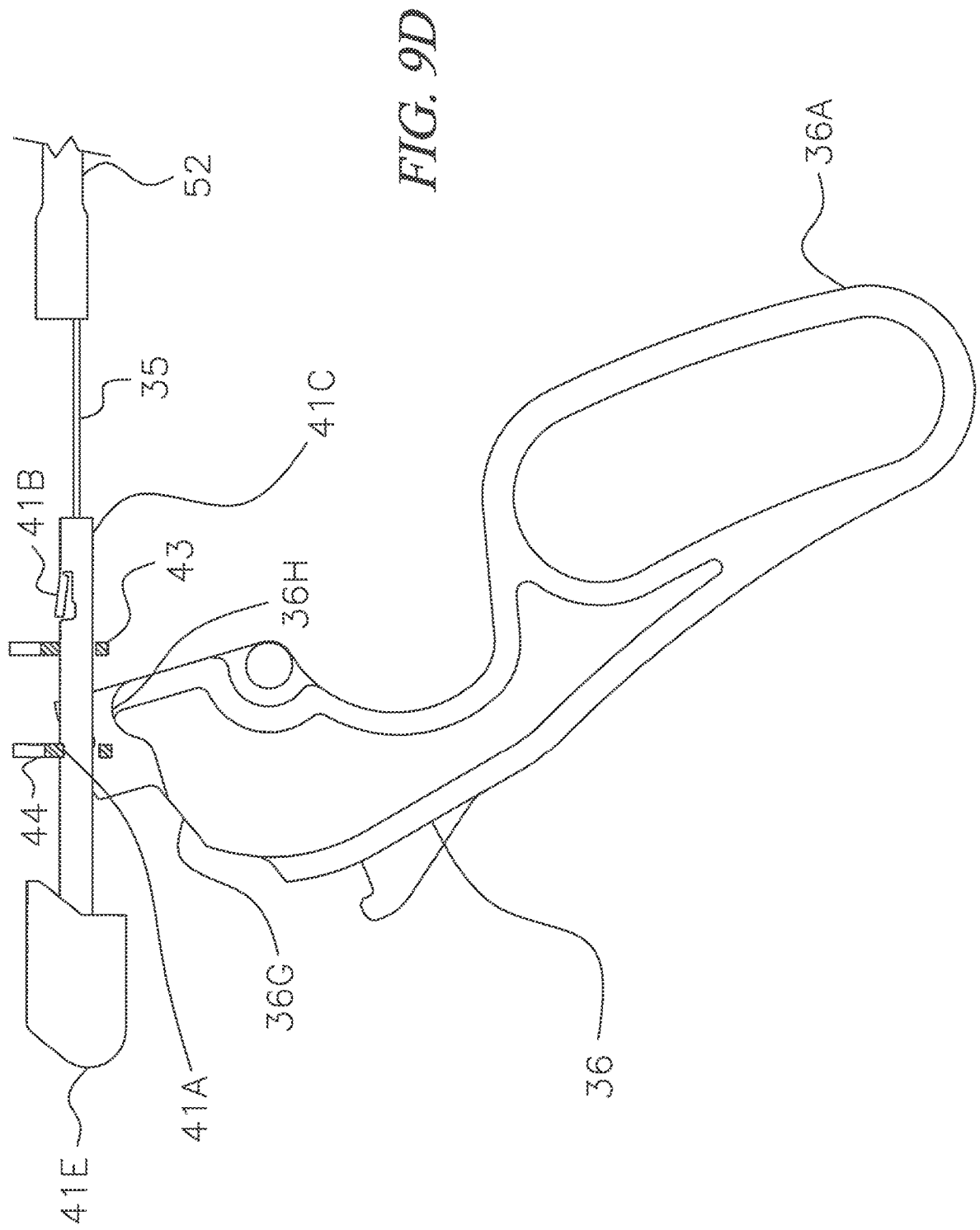

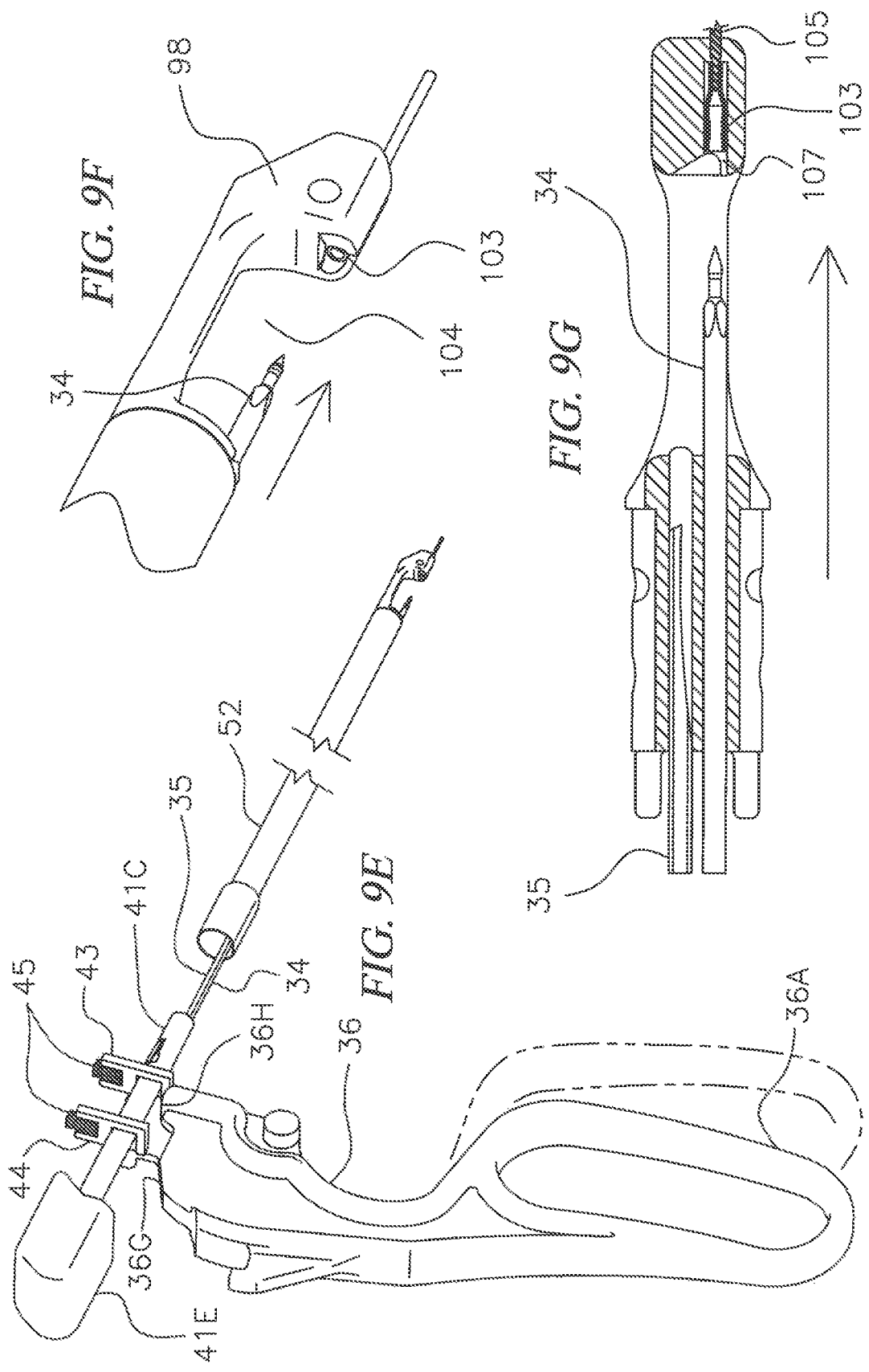

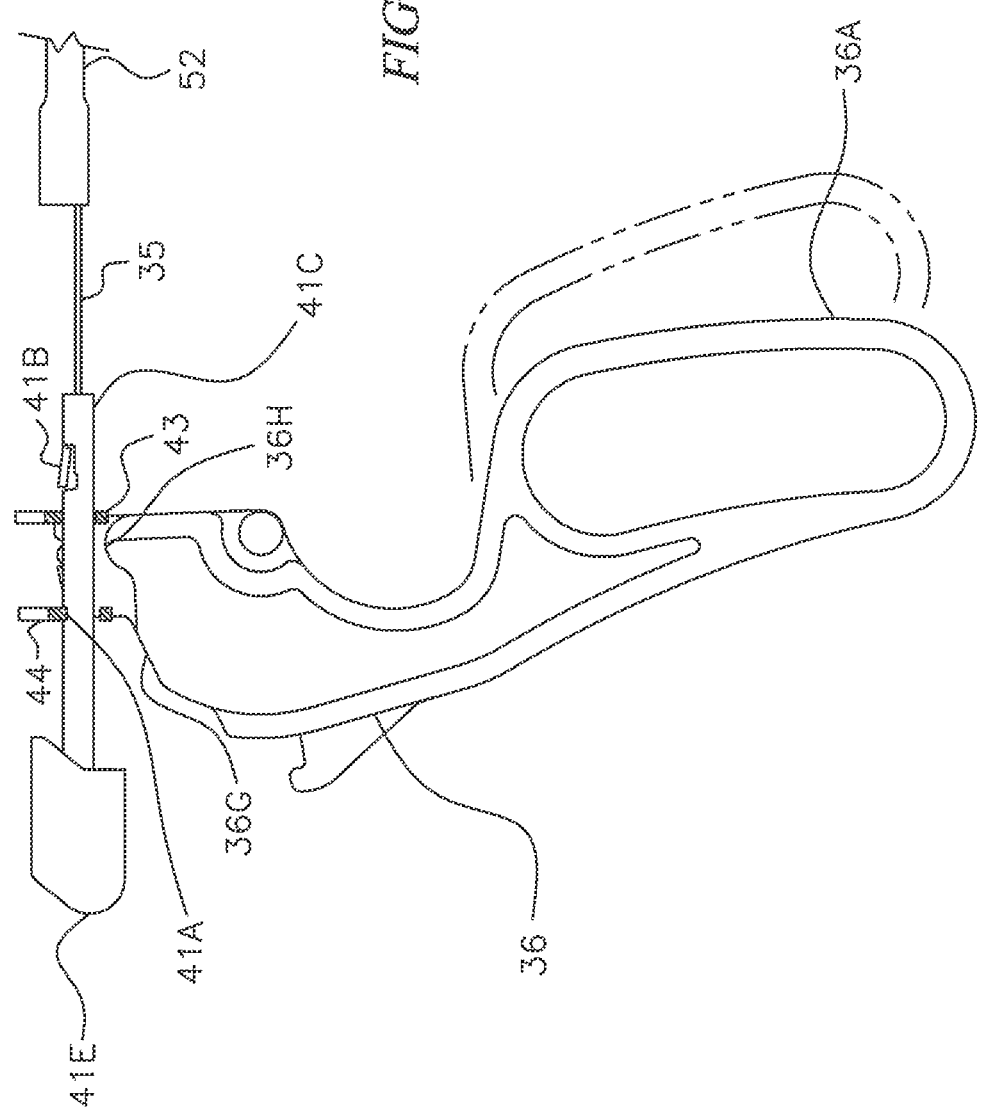

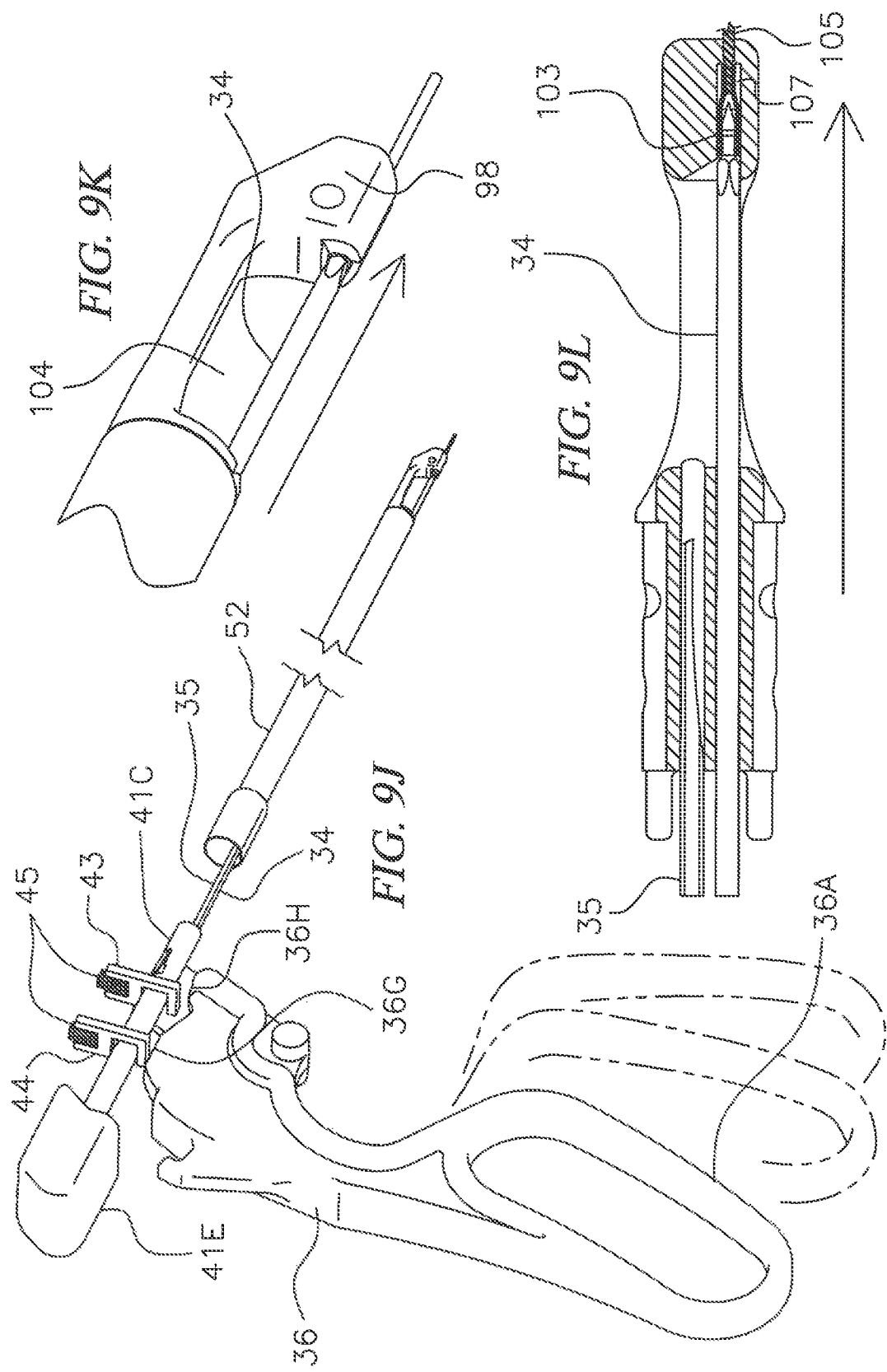

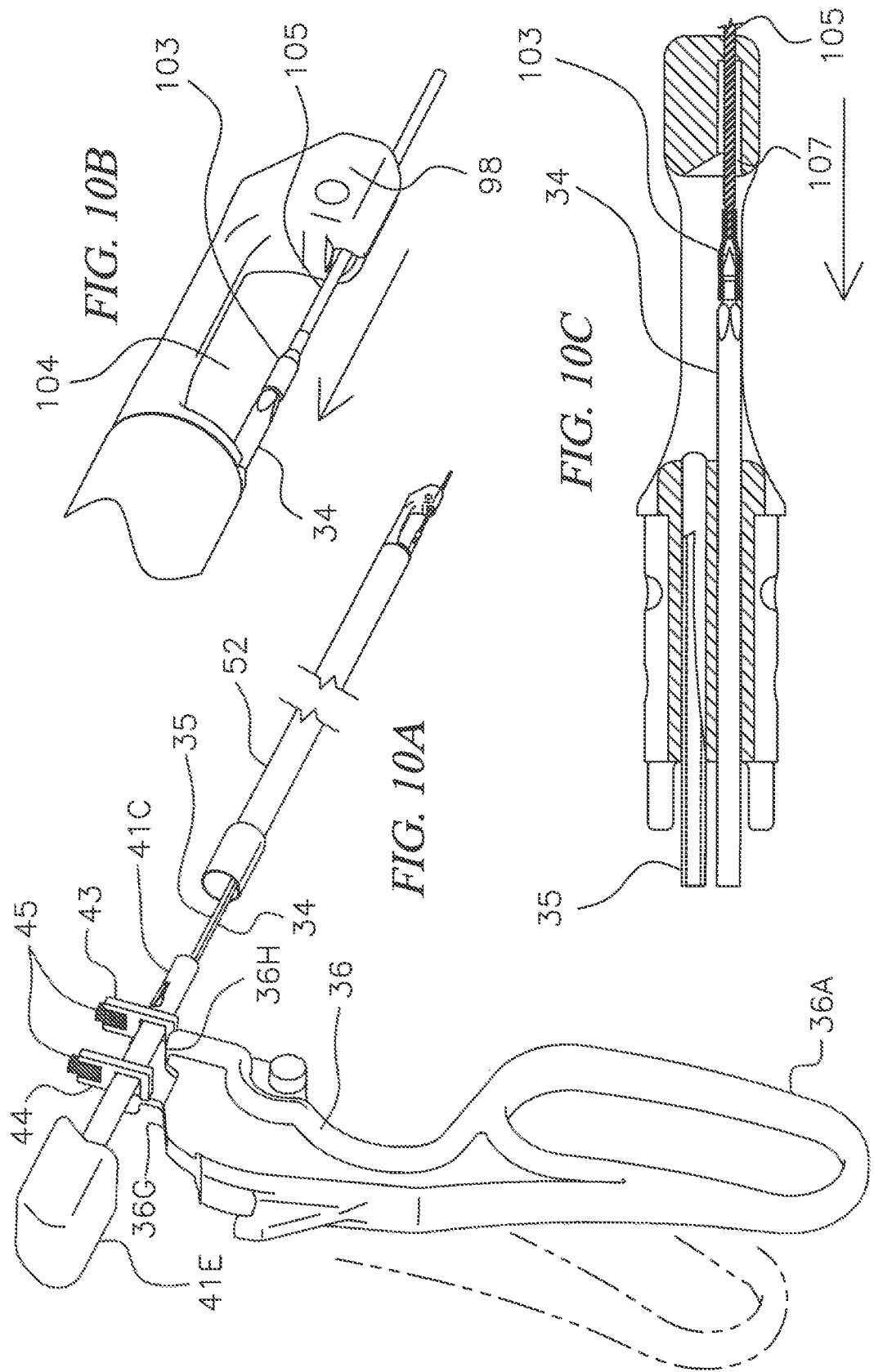

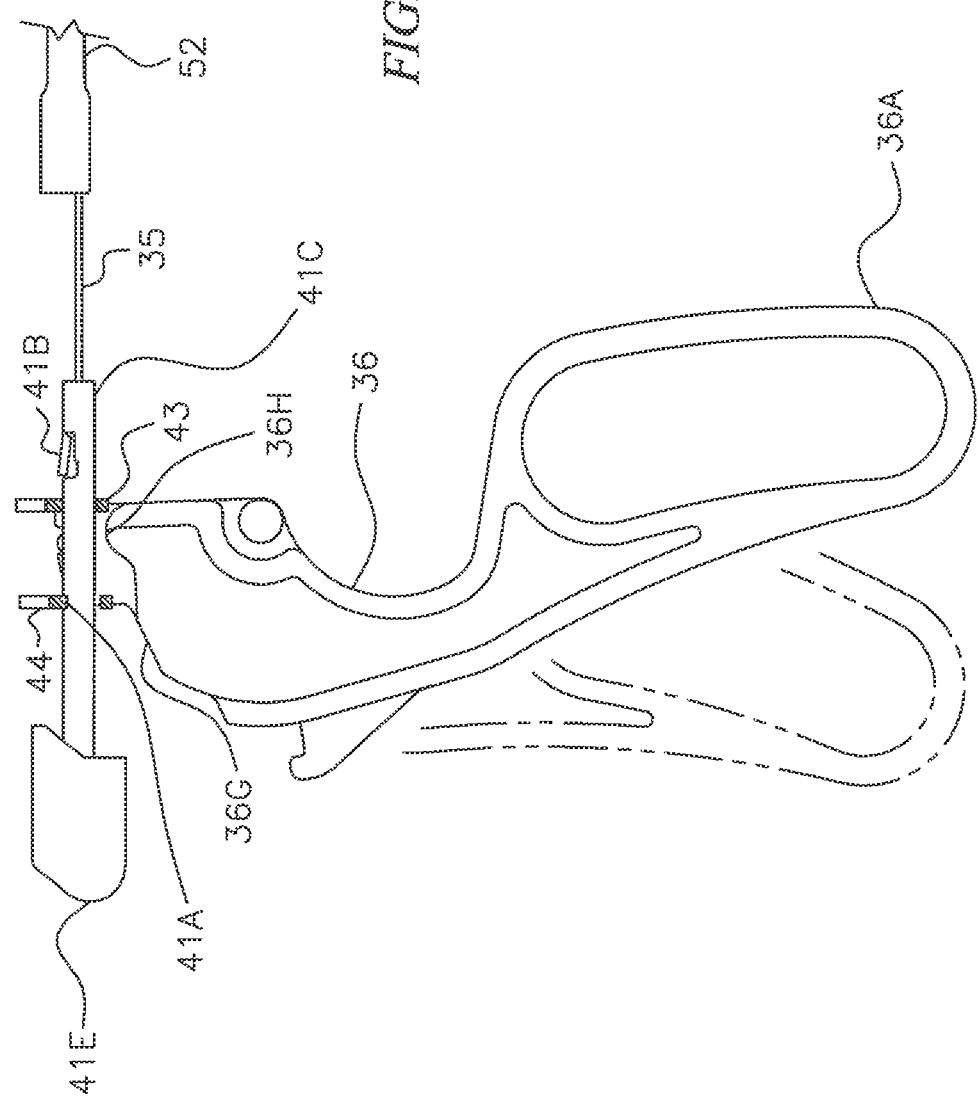

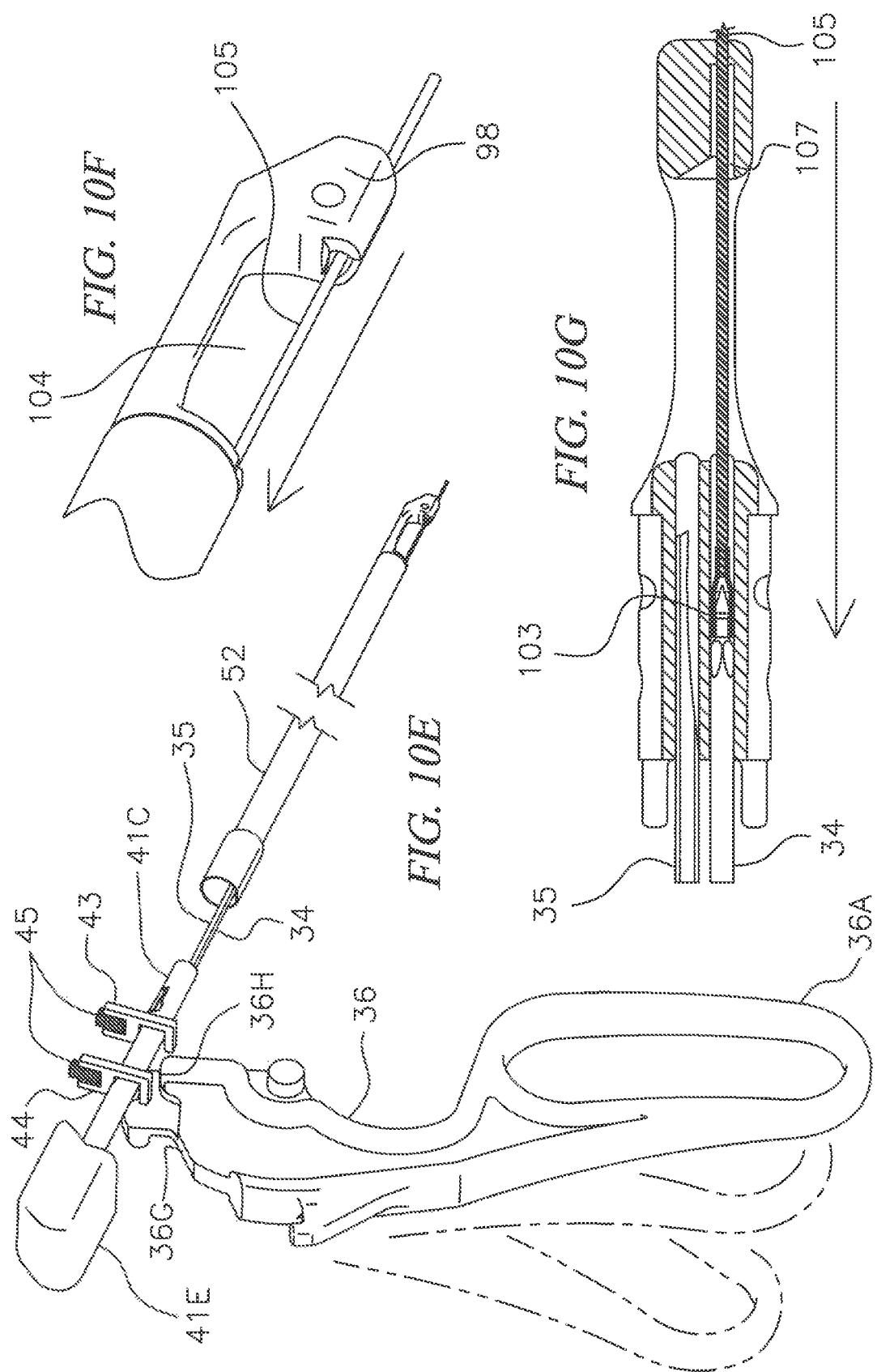

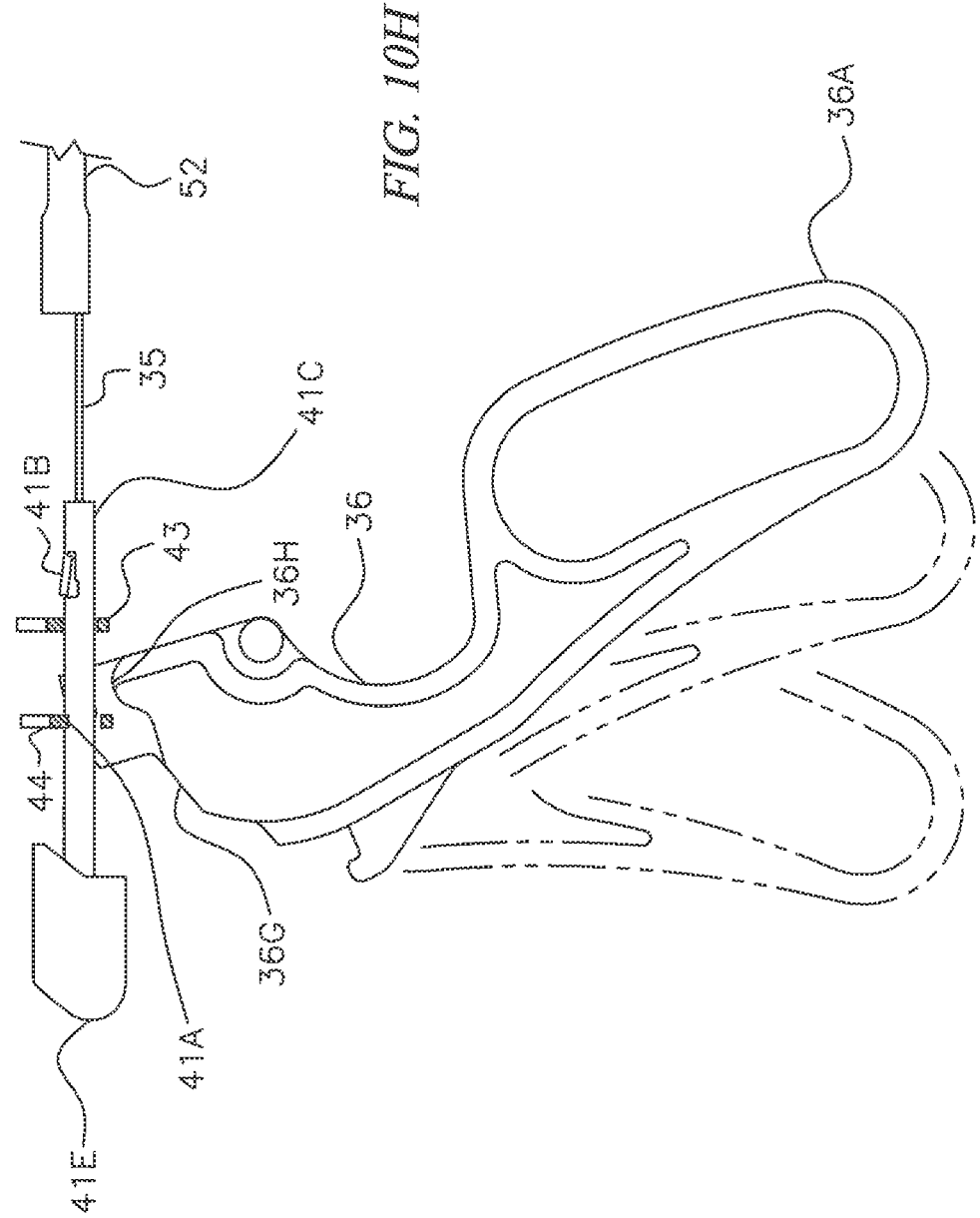

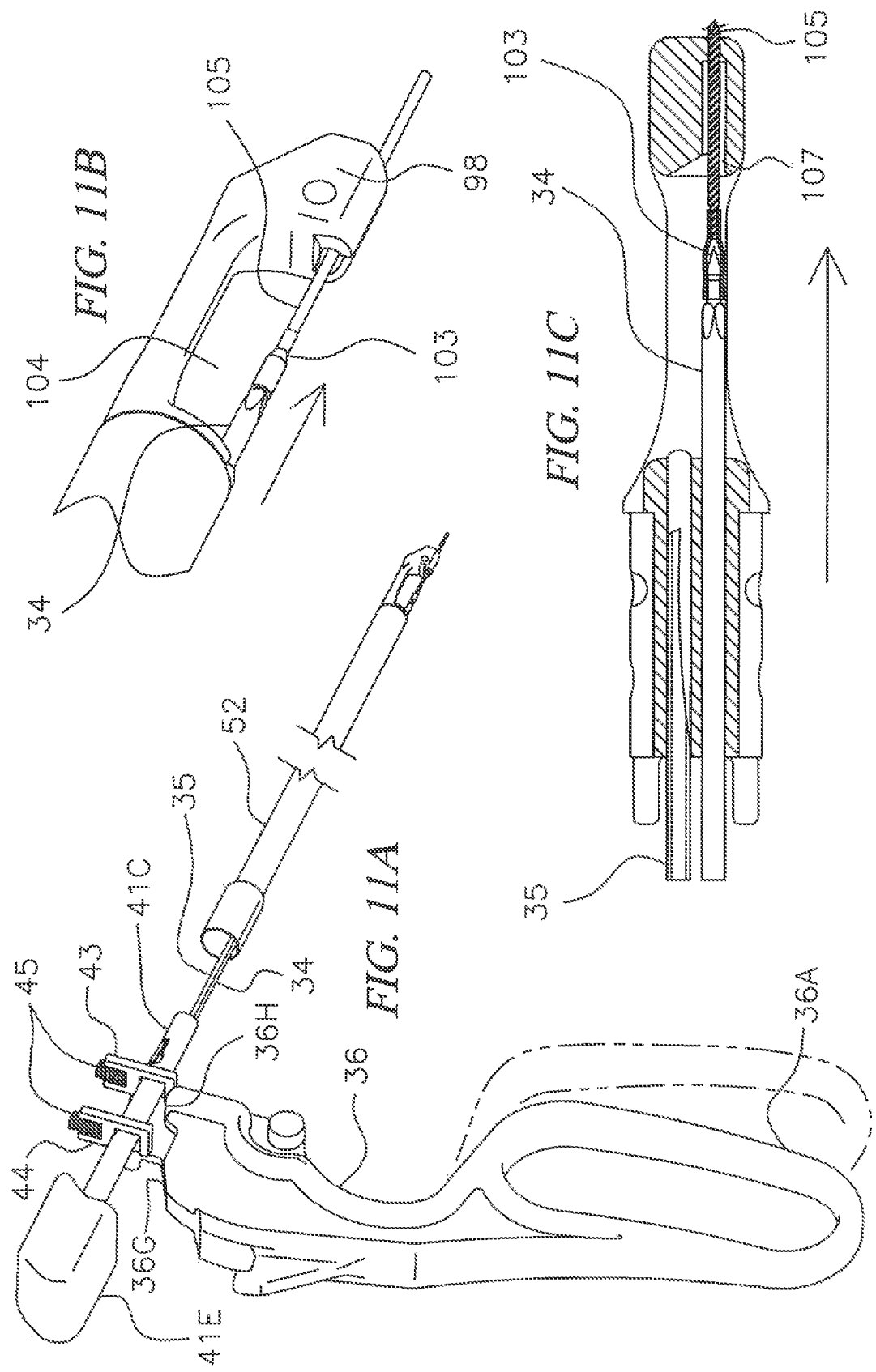

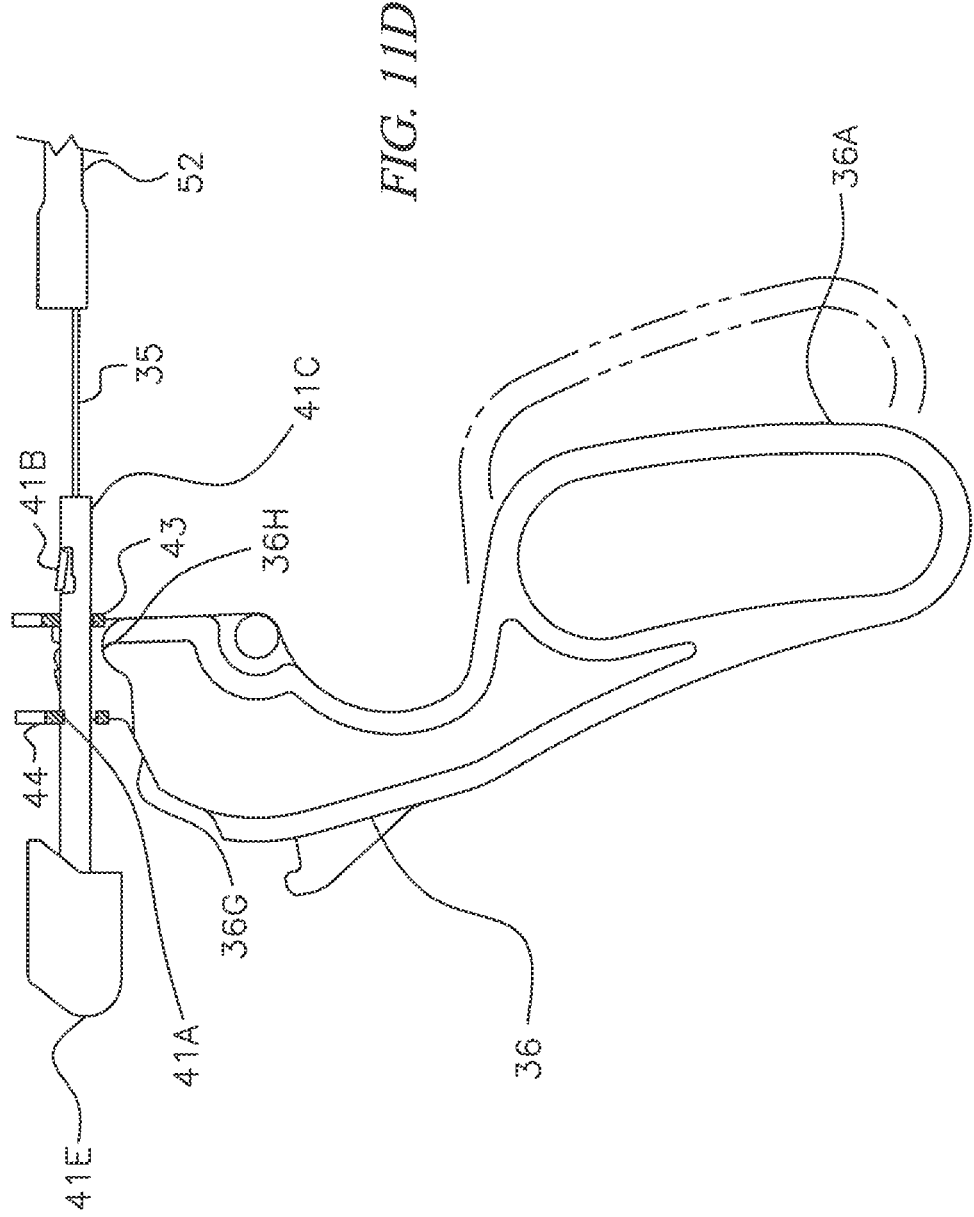

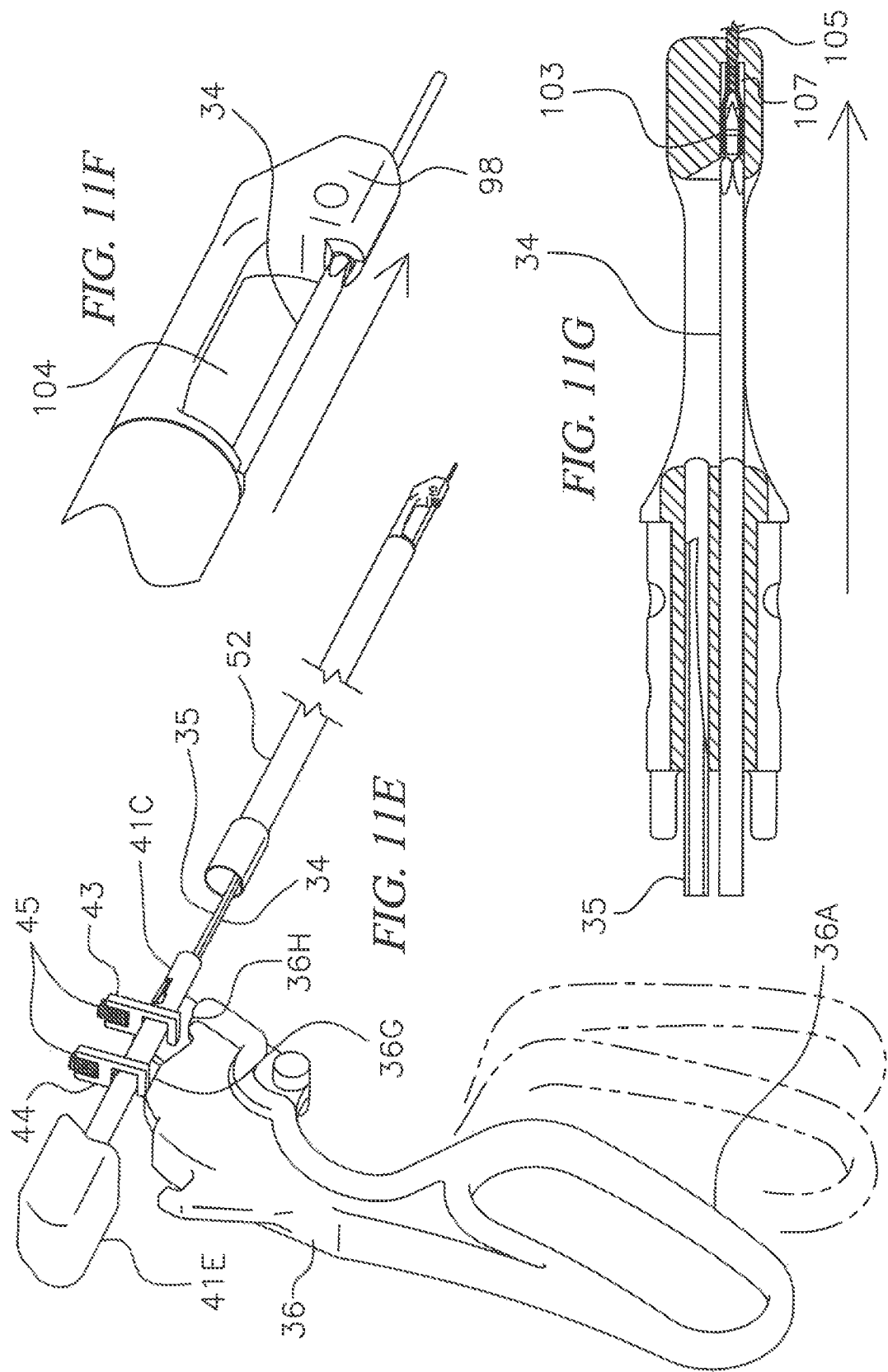

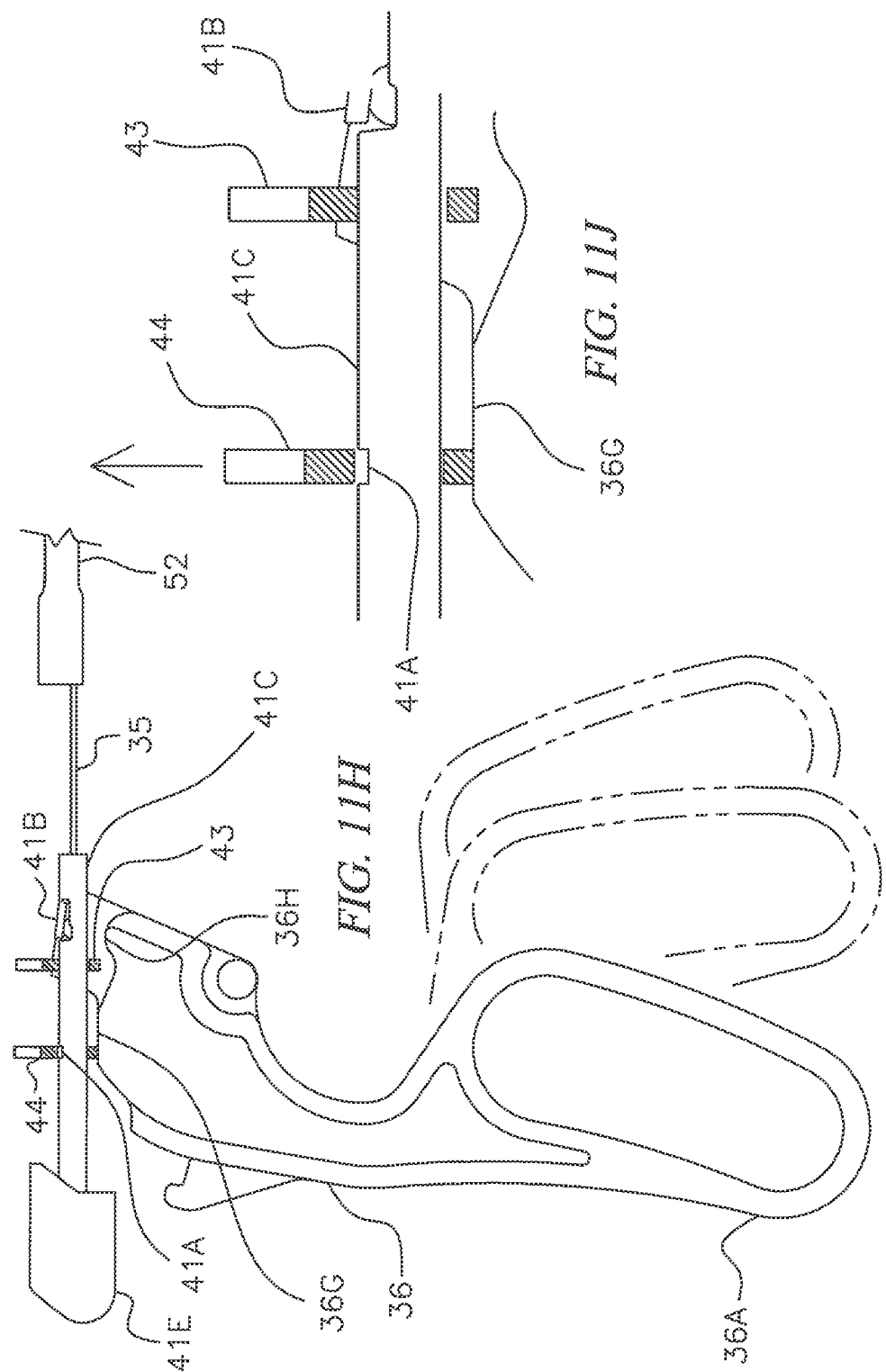

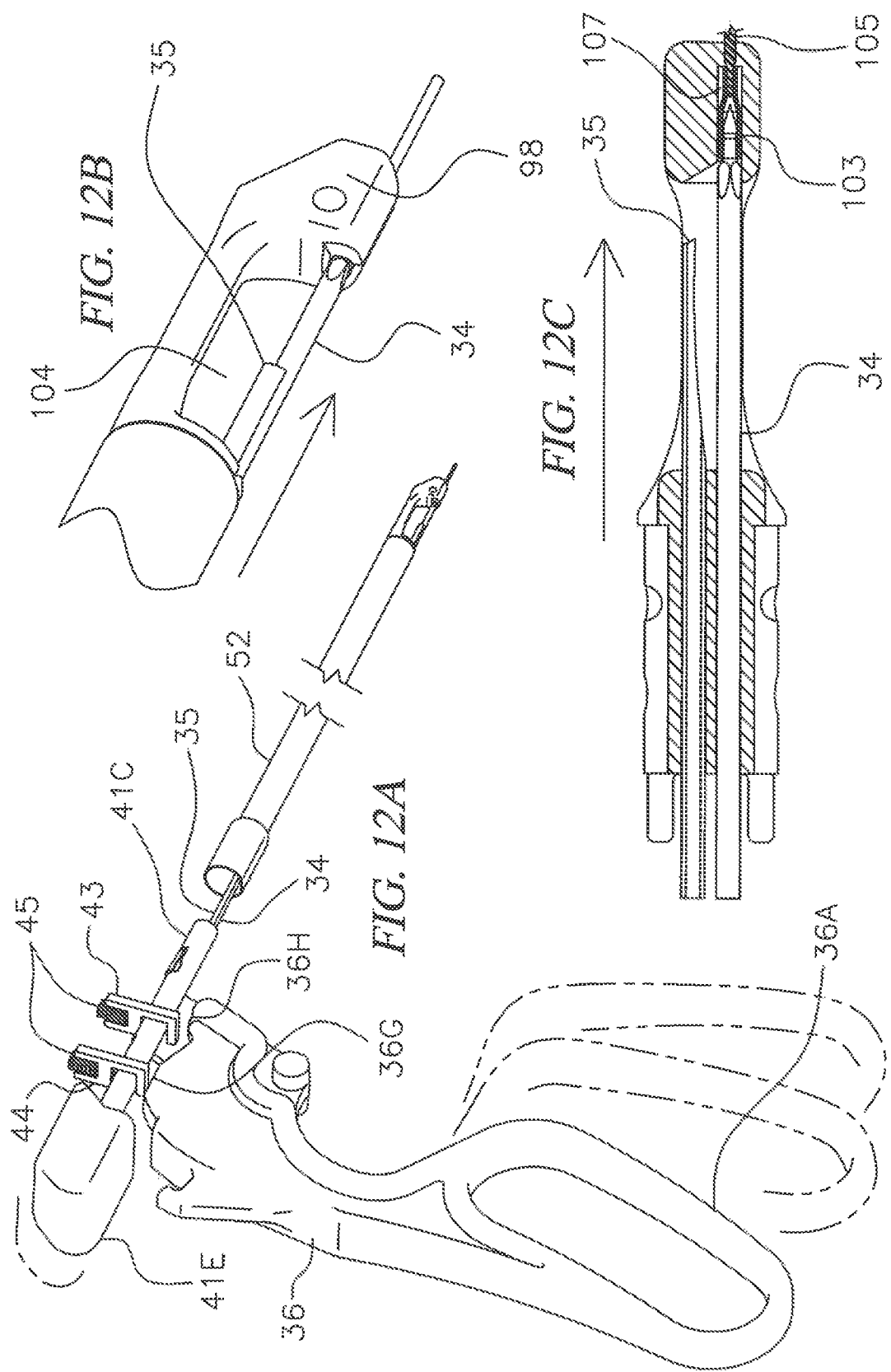

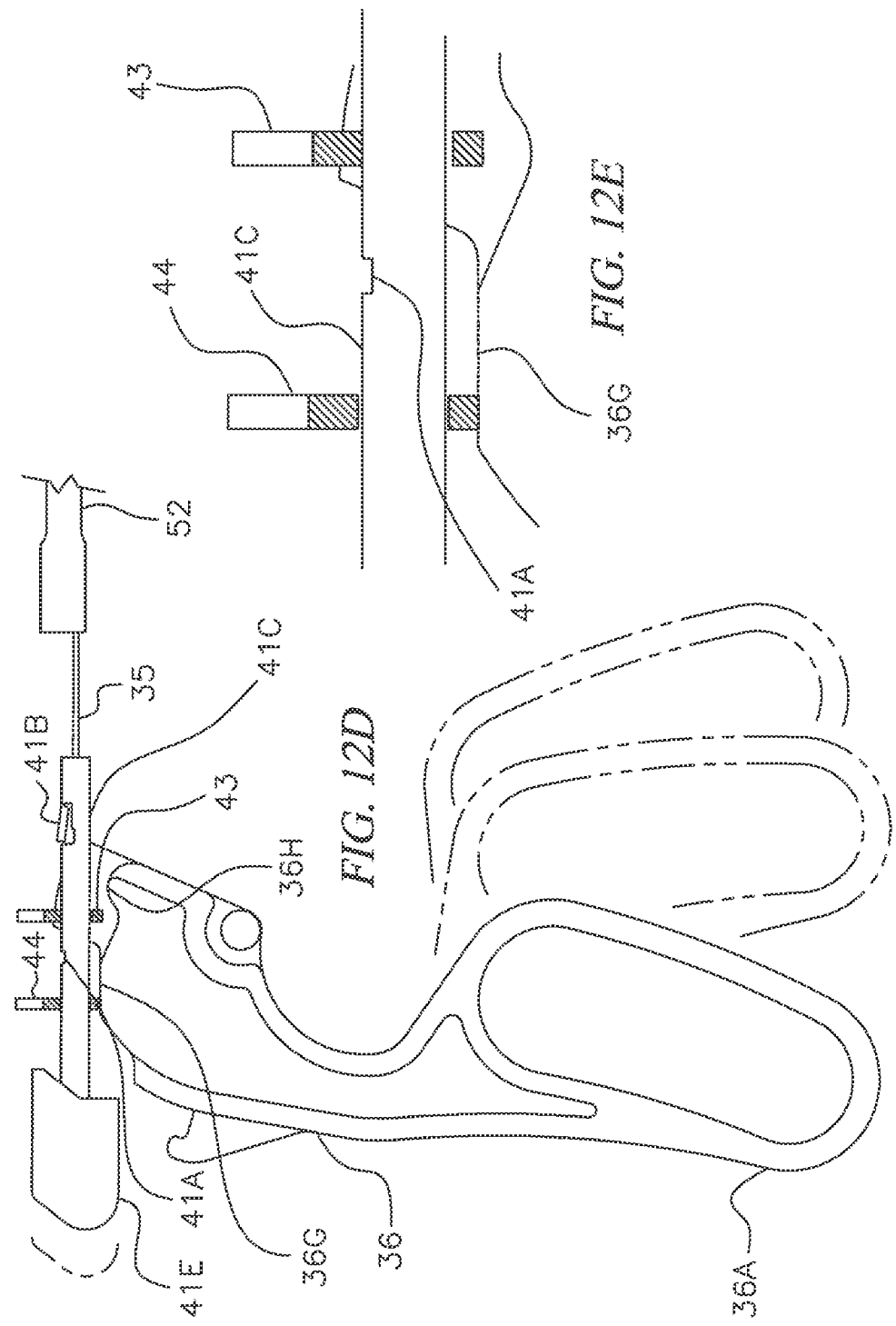

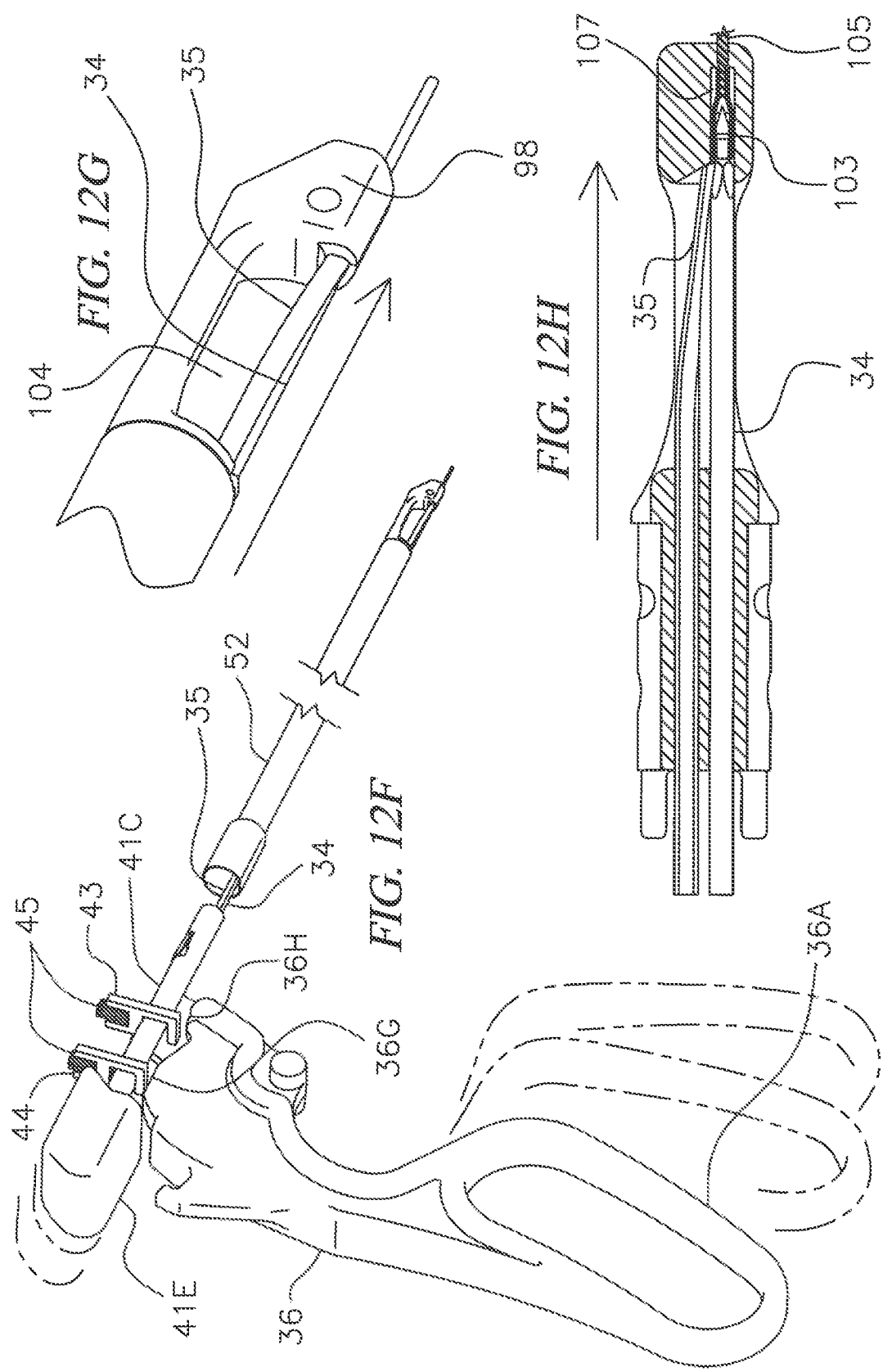

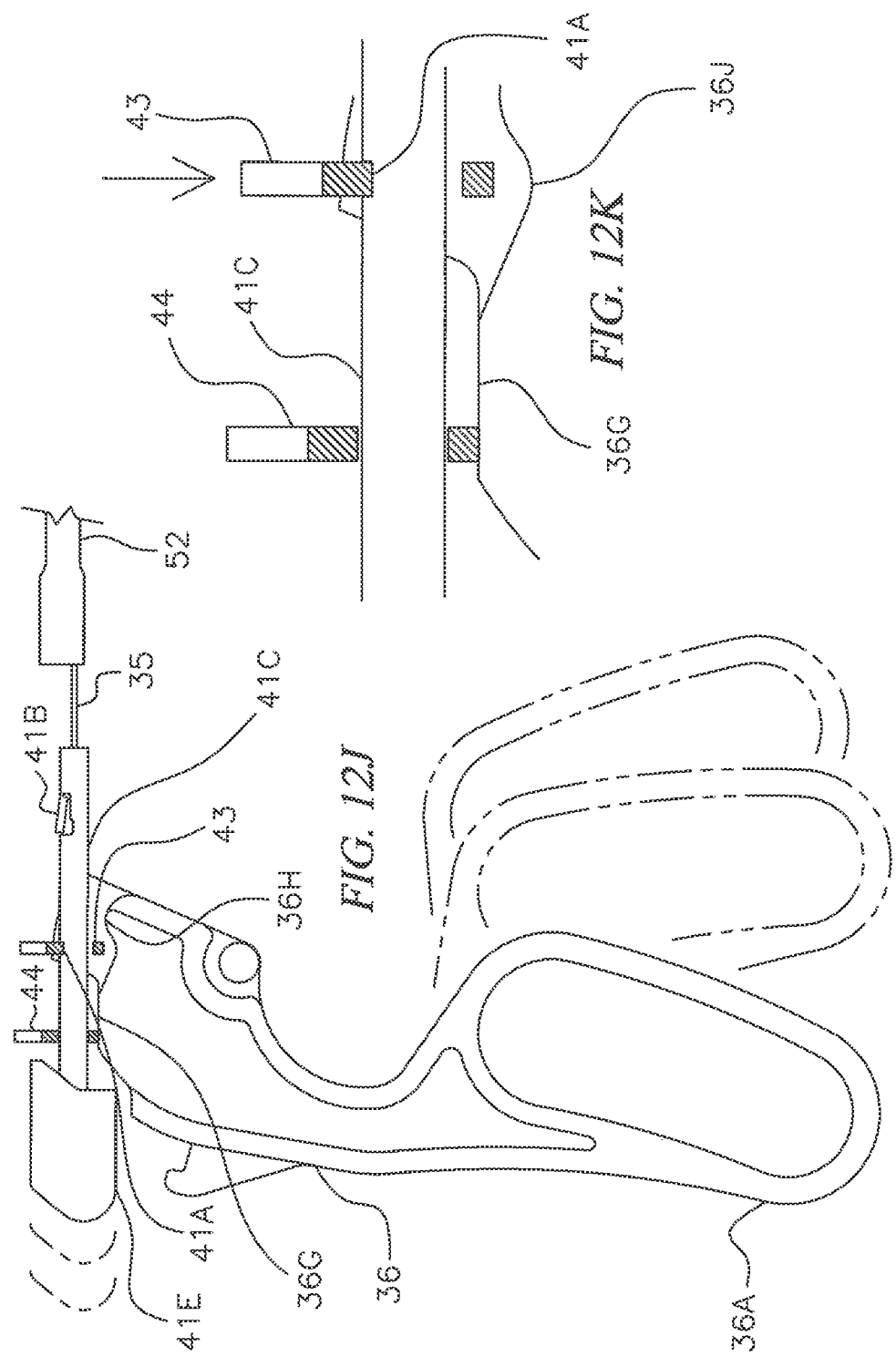

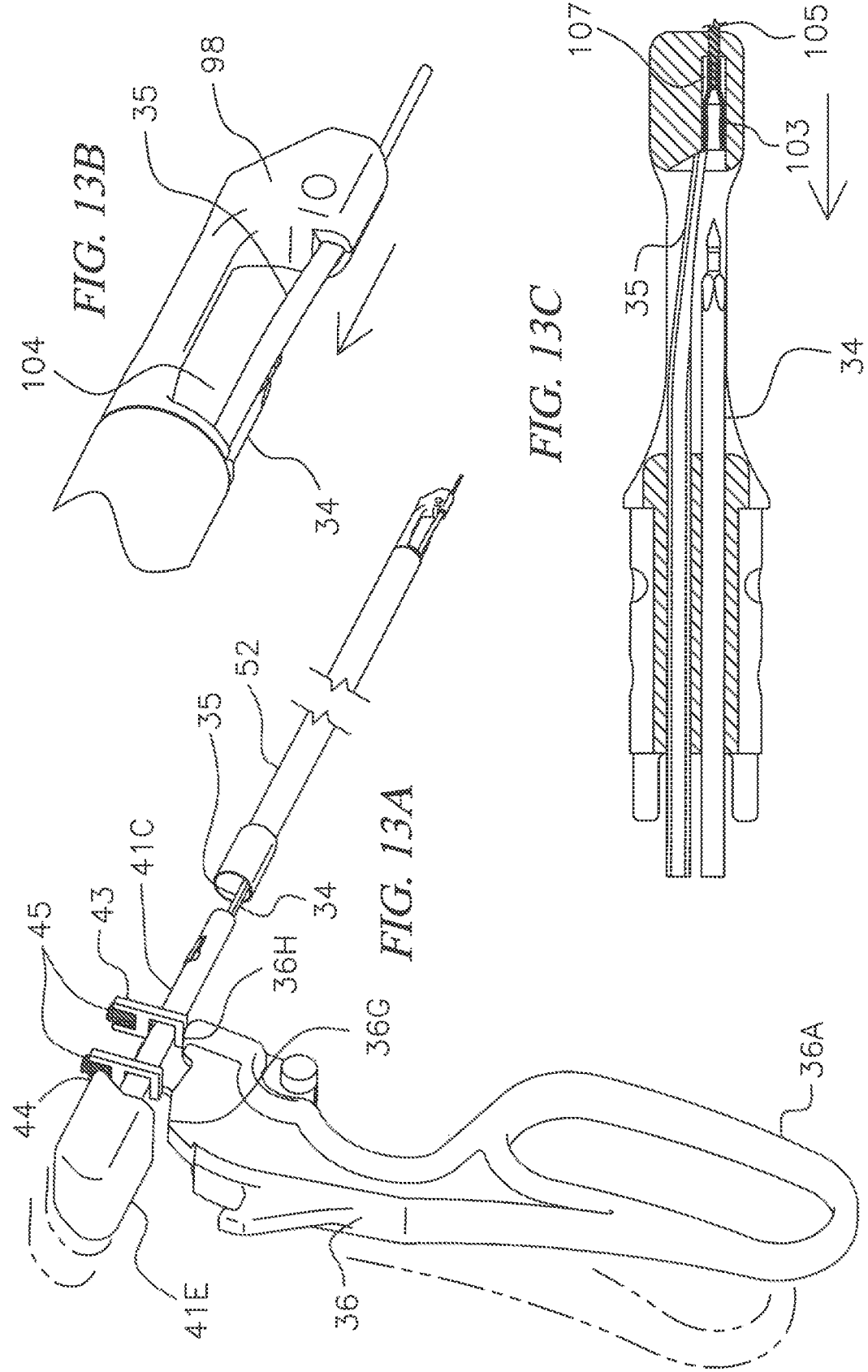

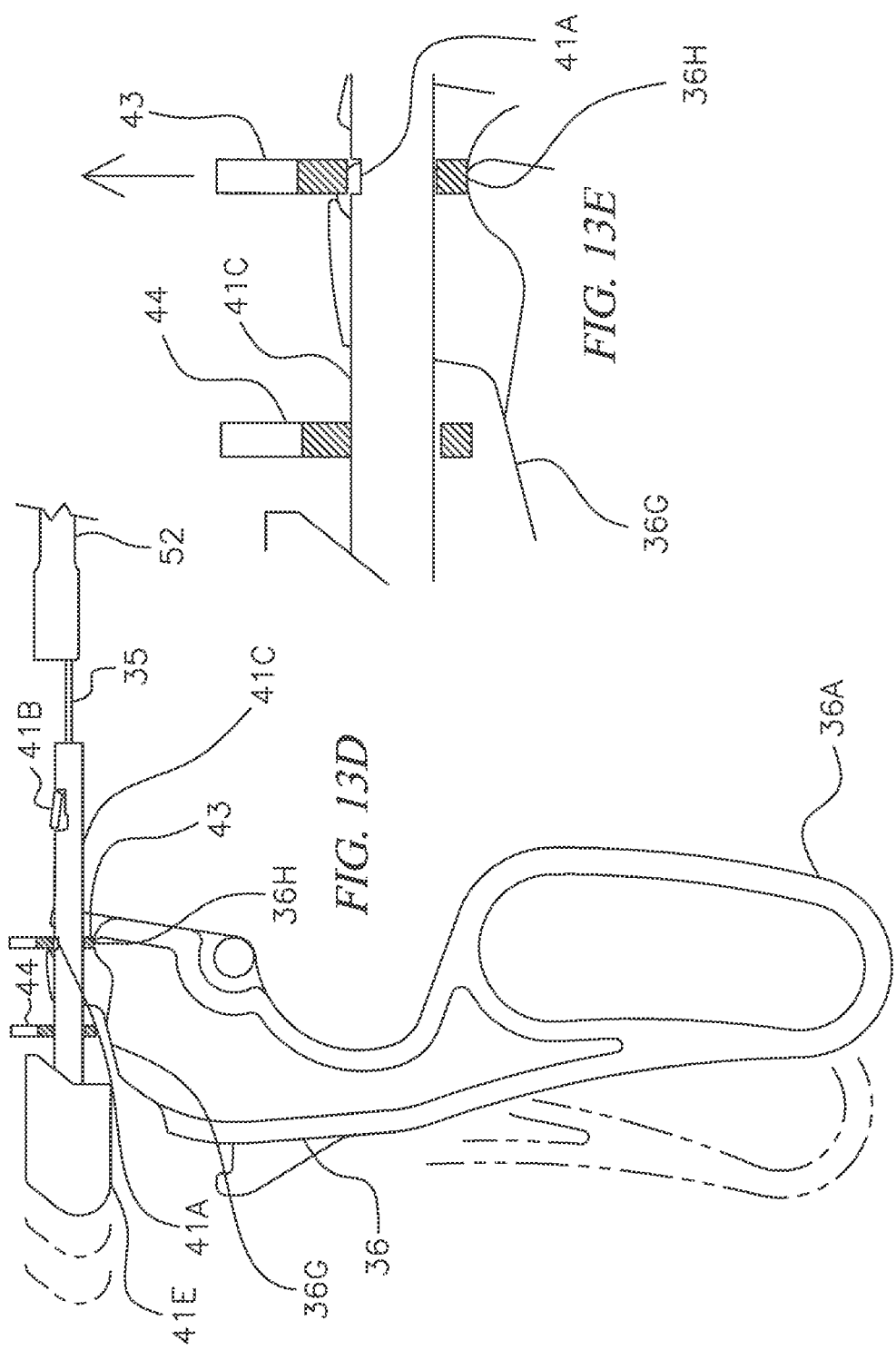

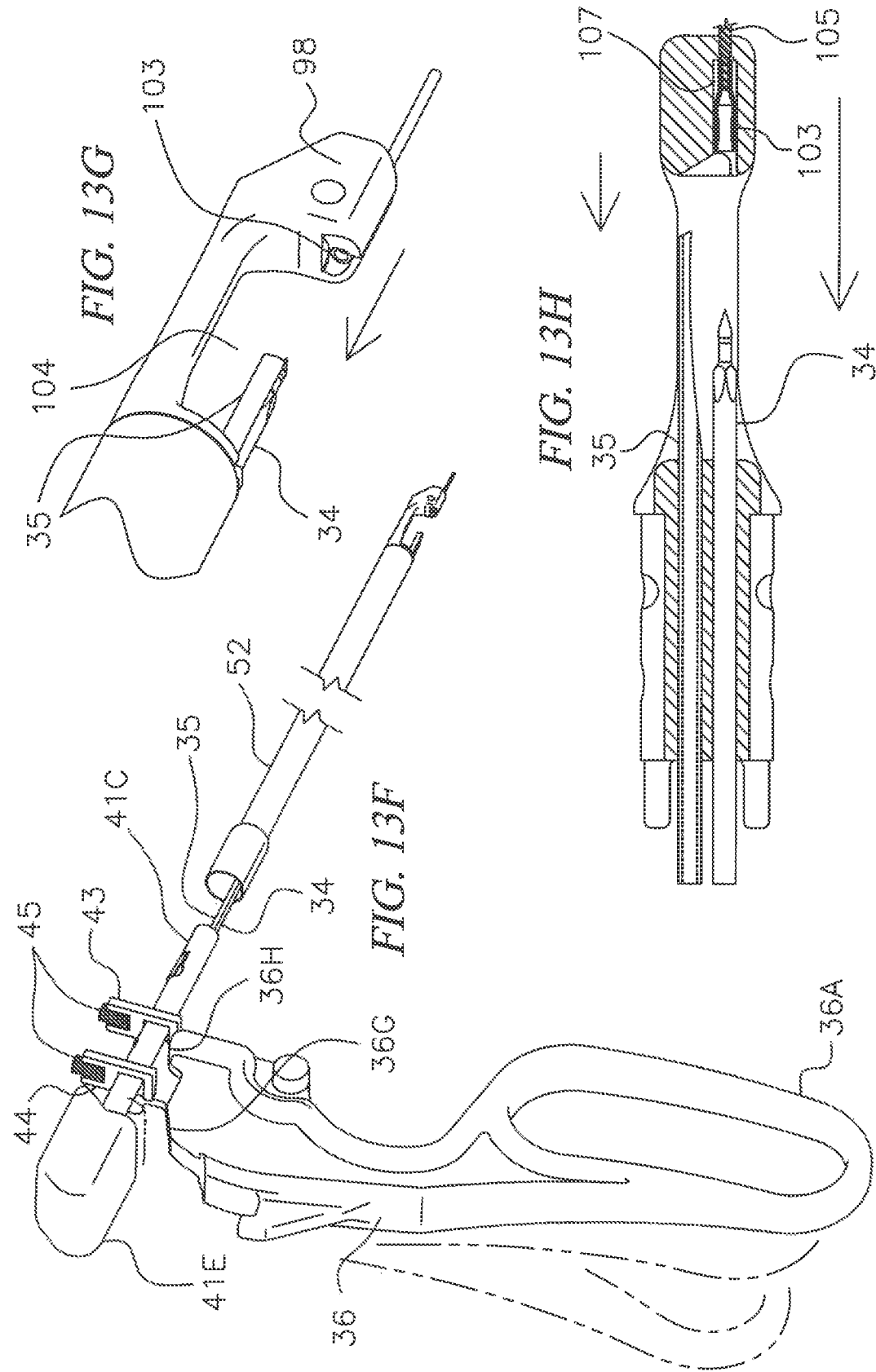

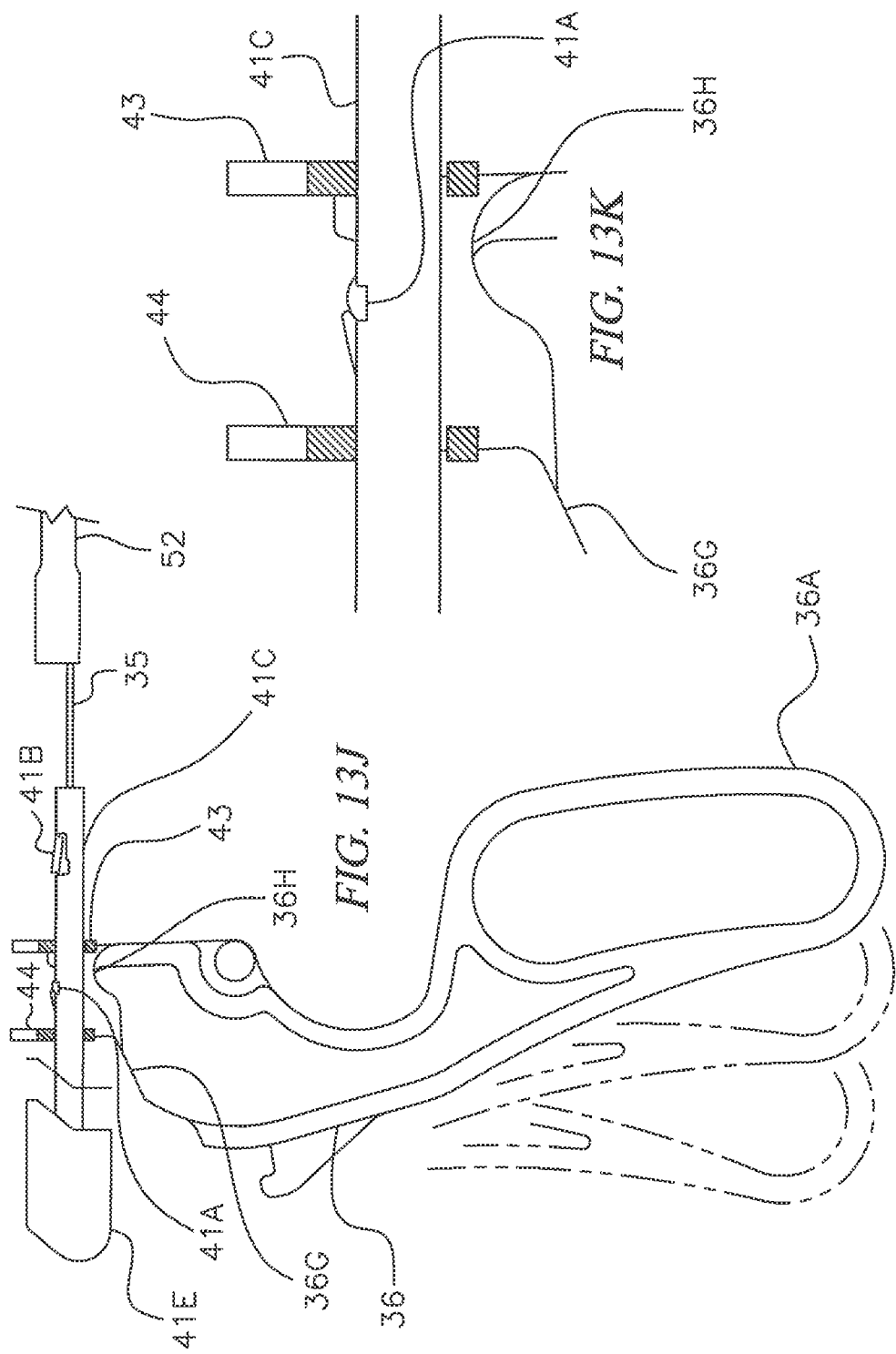

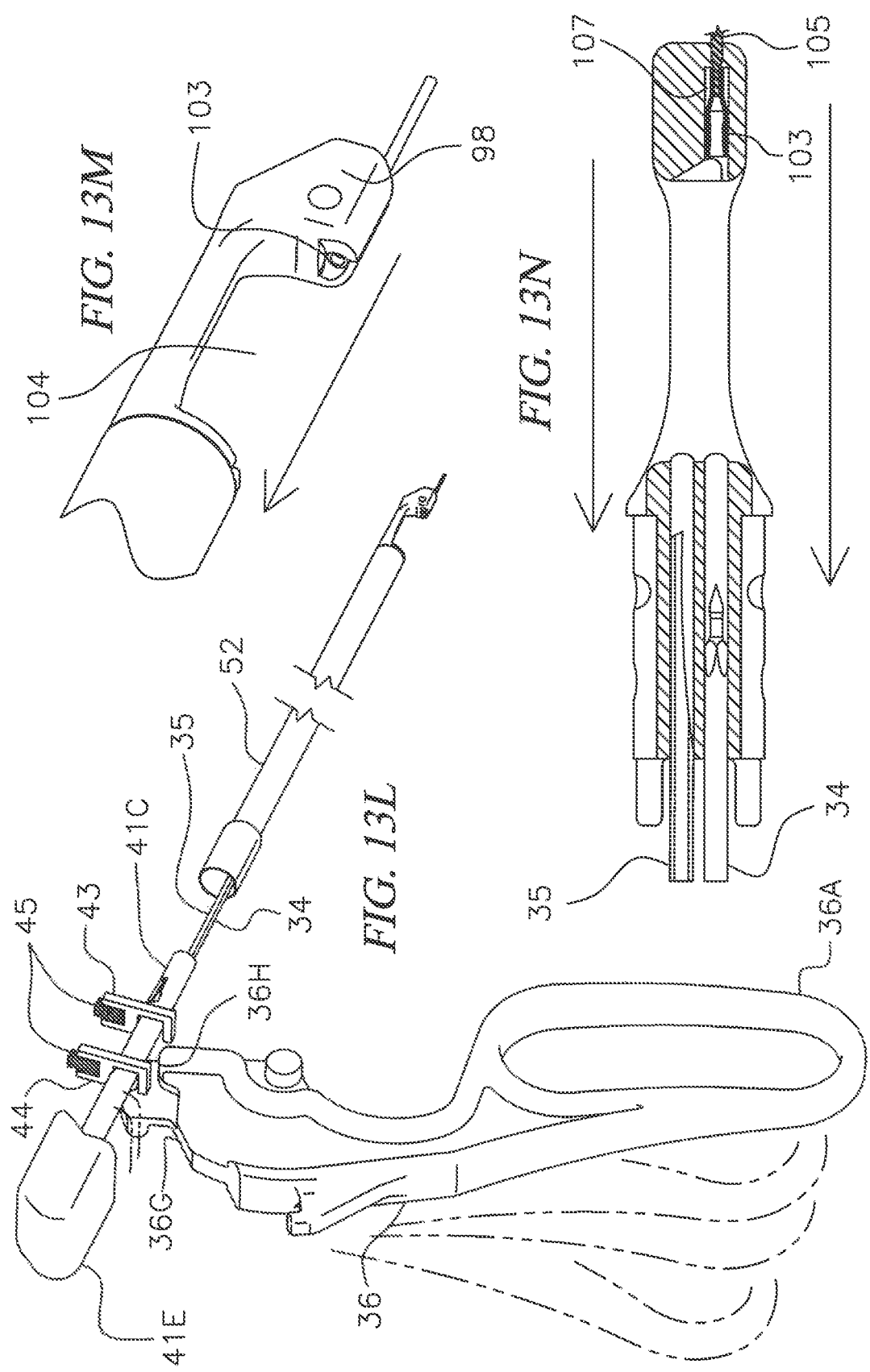

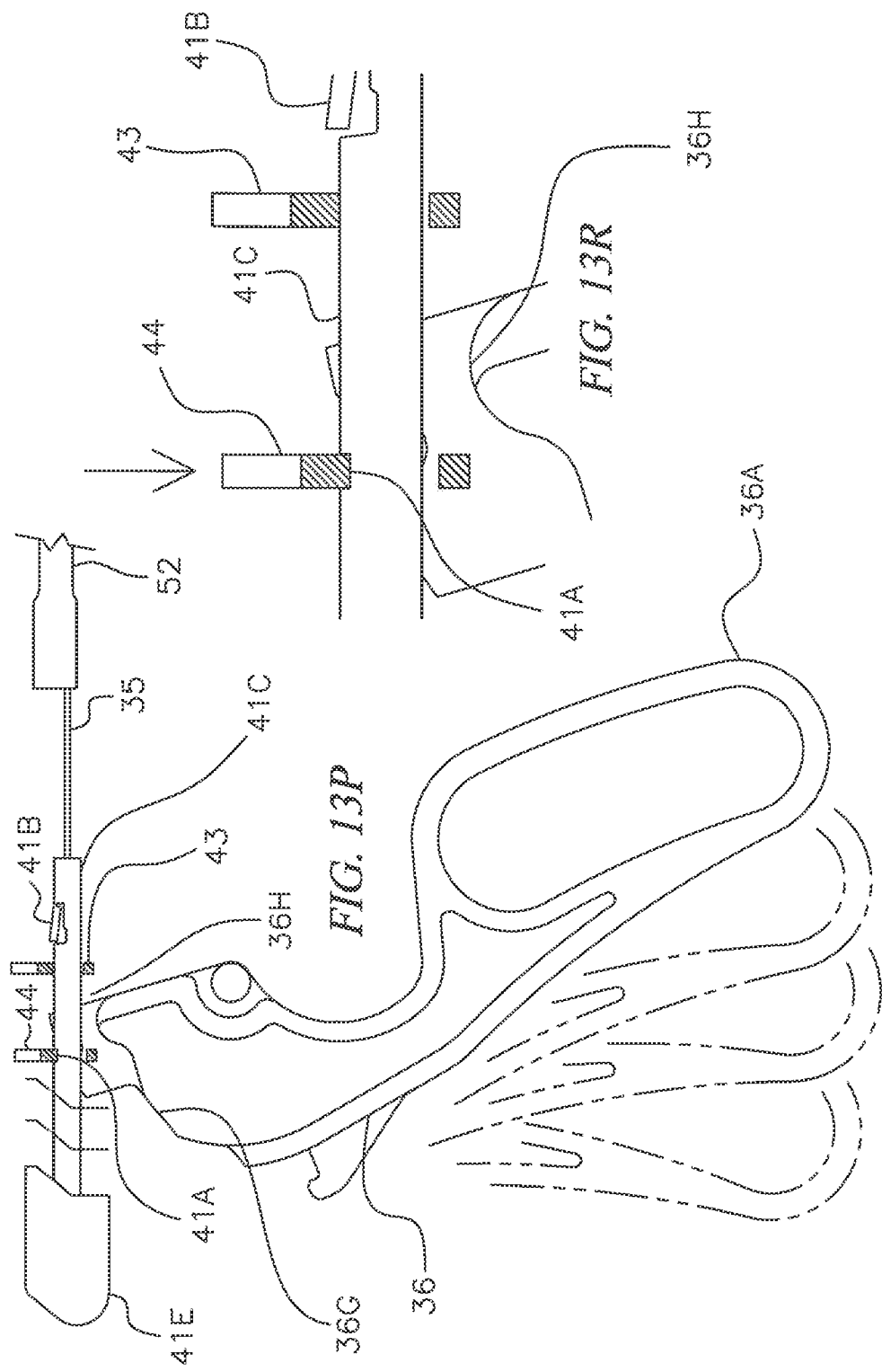

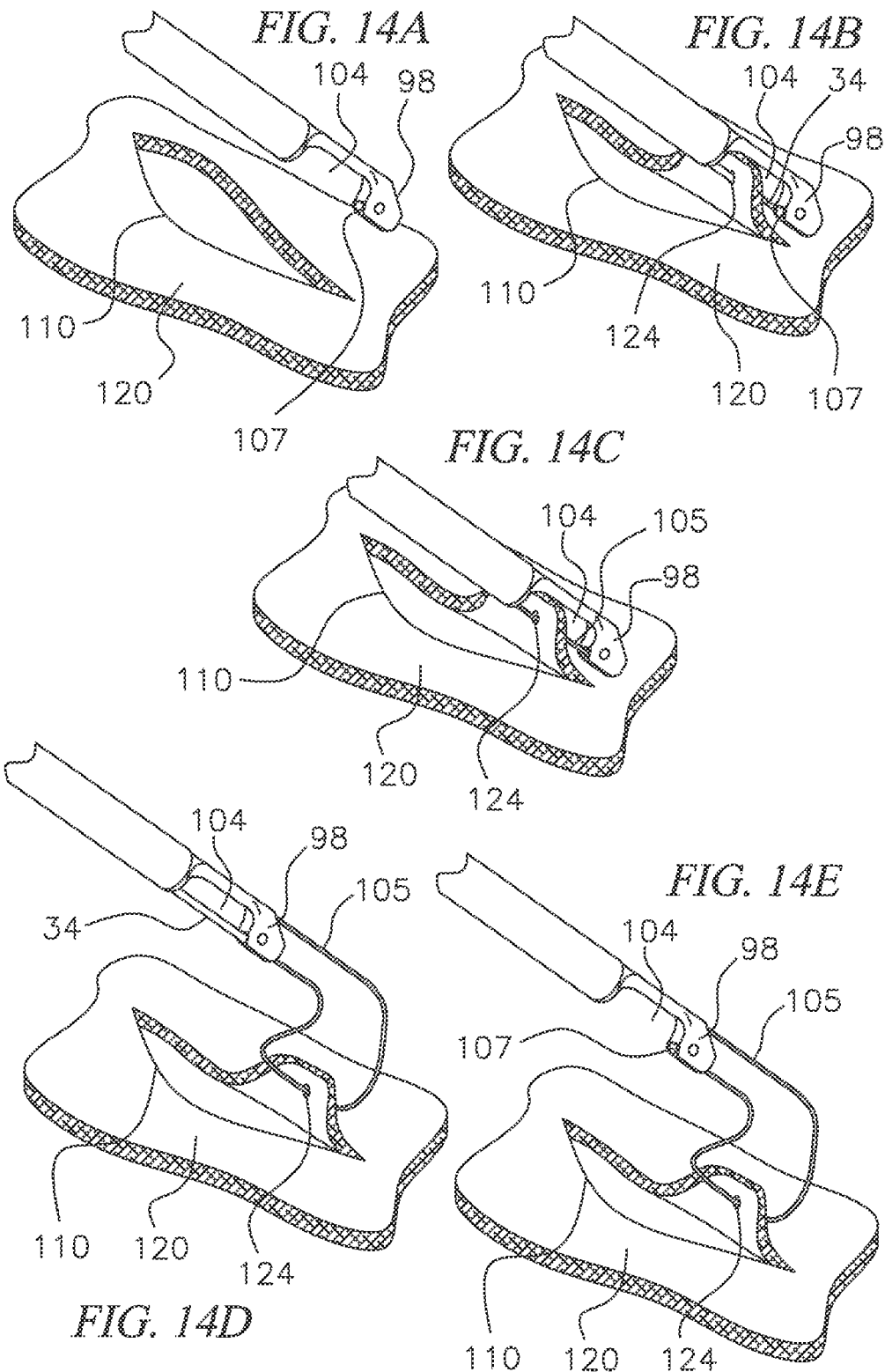

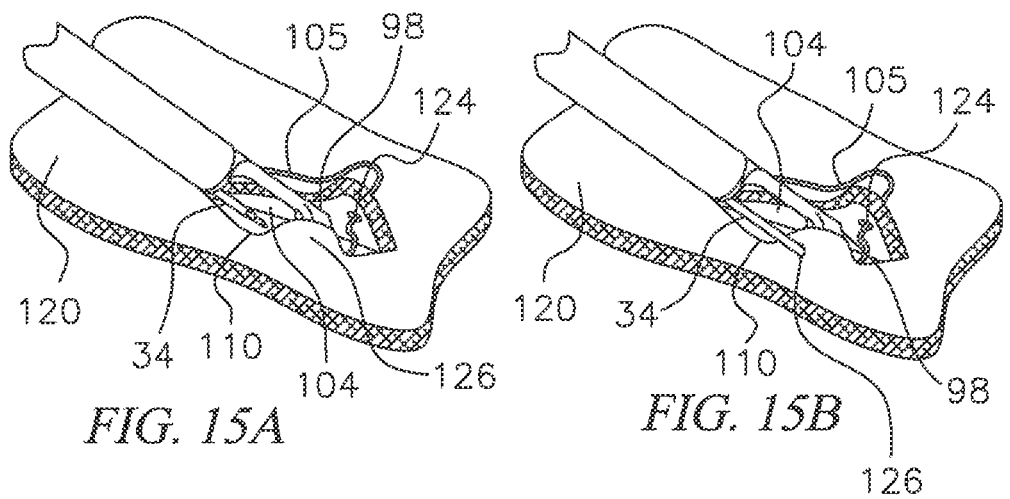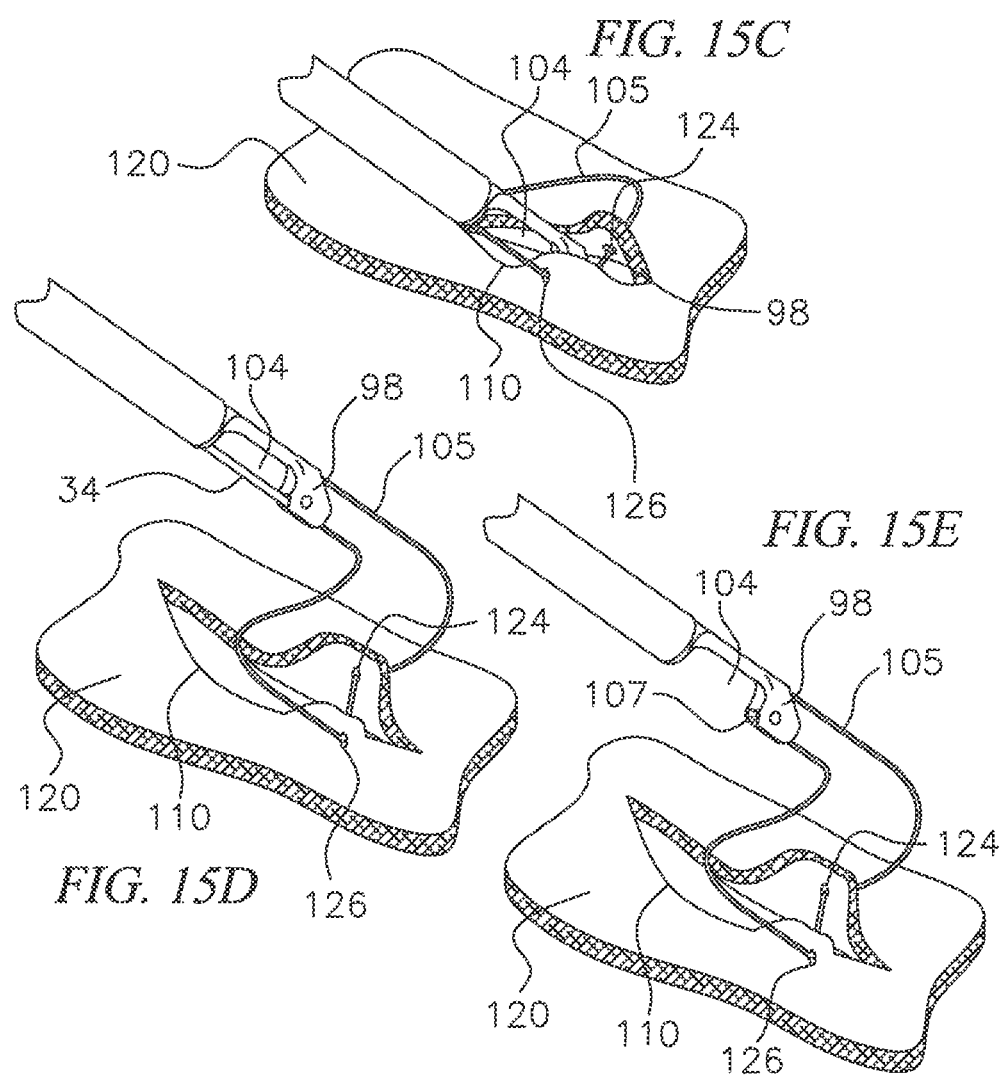
FIG. 15A  FIG. 15B  FIG. 15C  FIG. 15D  FIG. 15E

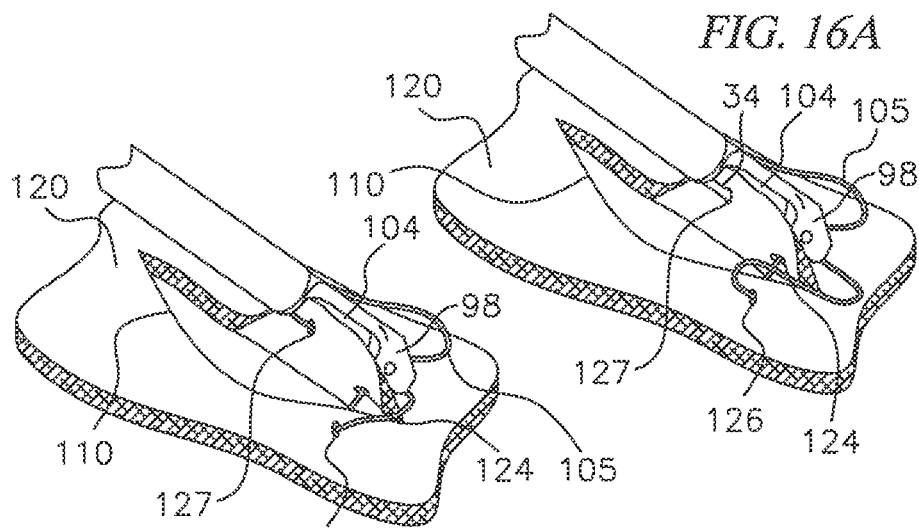
FIG. 16A
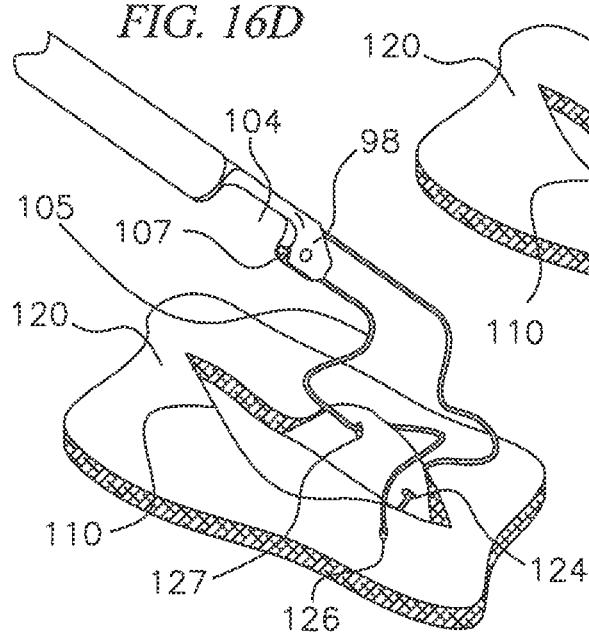
FIG. 16B
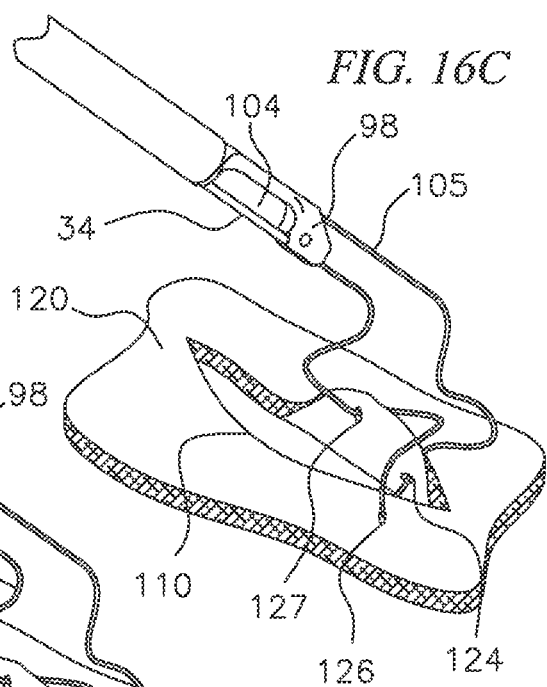
FIG. 16C
FIG. 16D

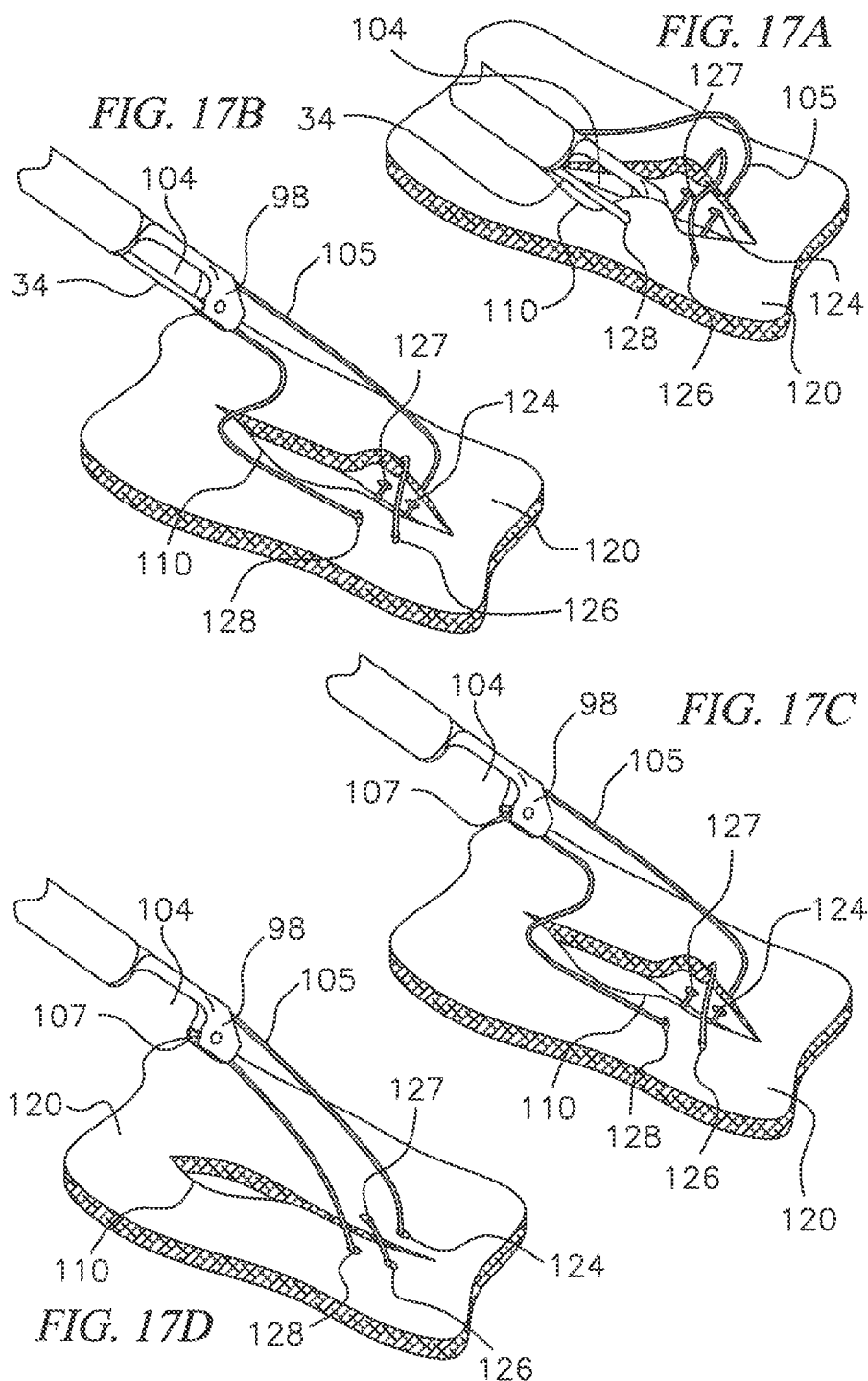

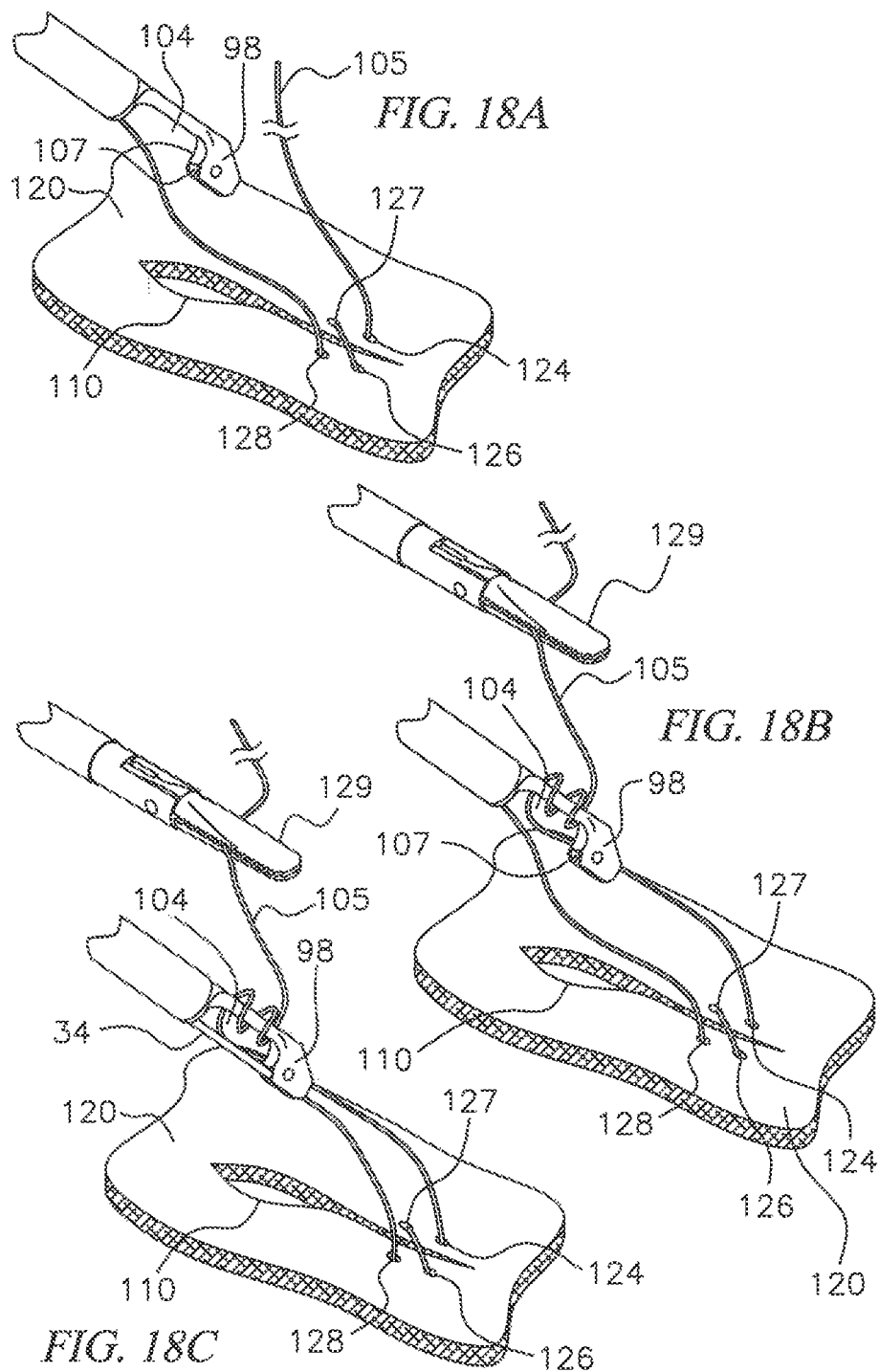

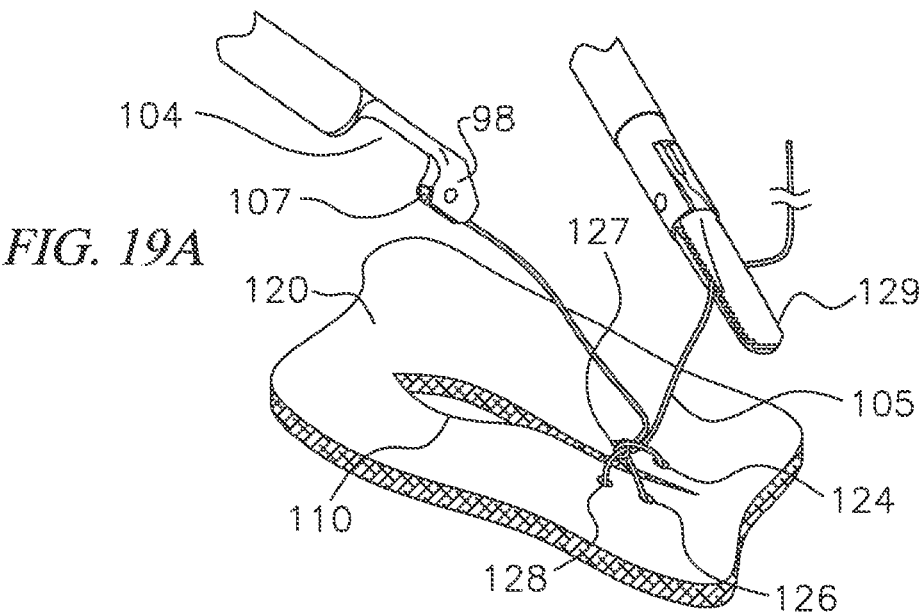

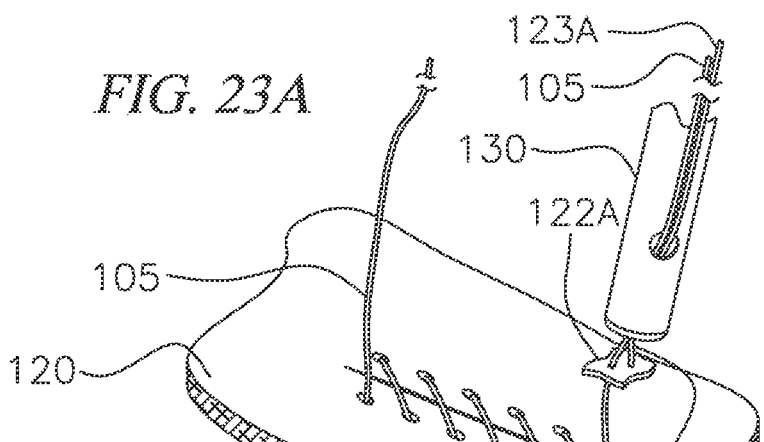
FIG. 23A
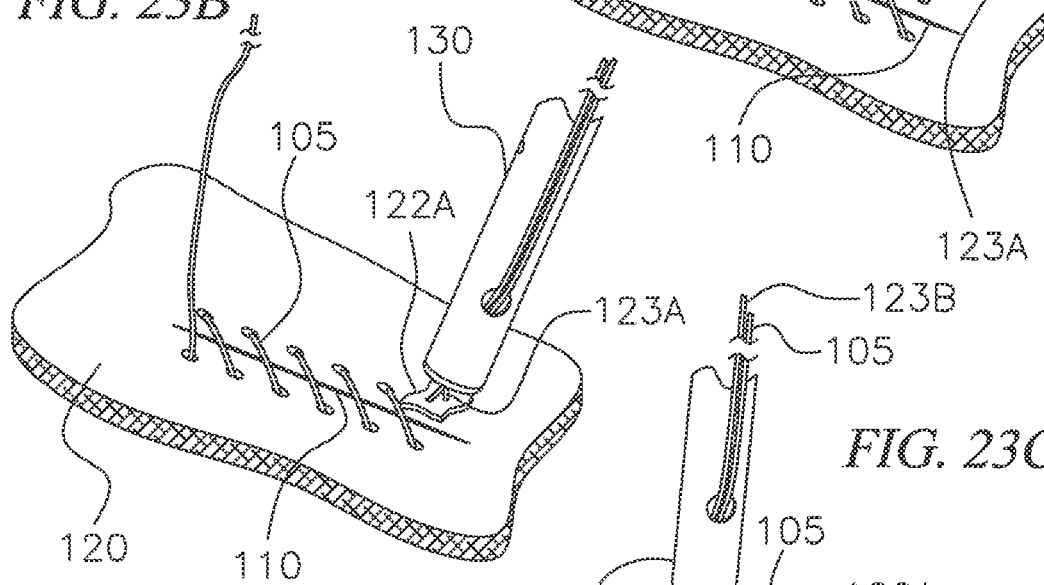
FIG. 23B
FIG. 23C
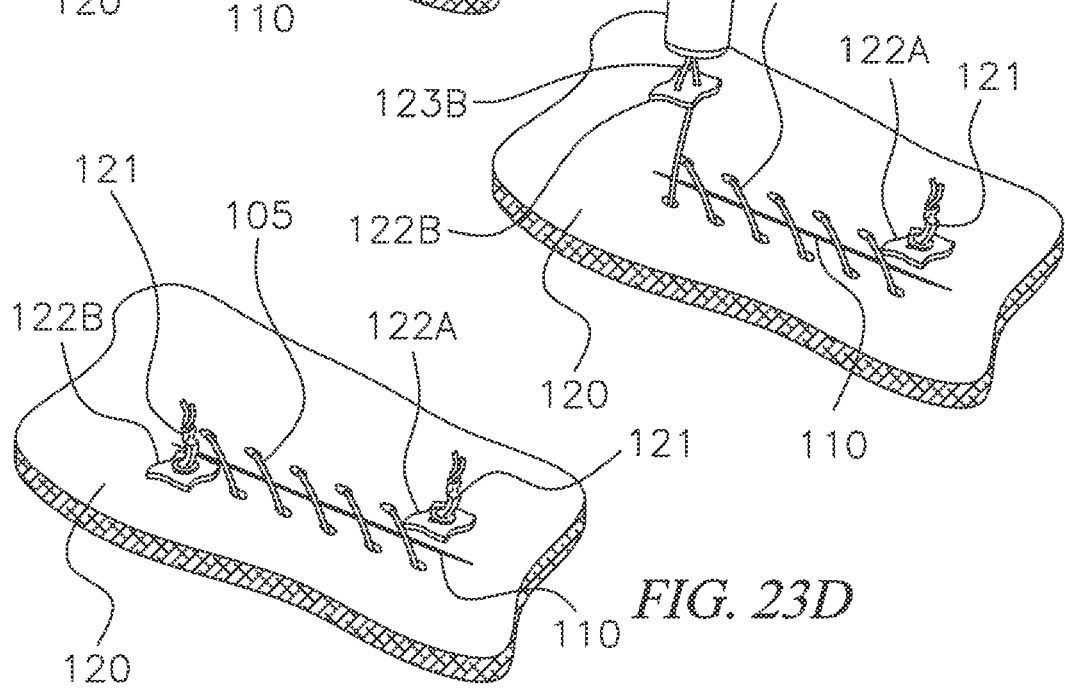
FIG. 23D

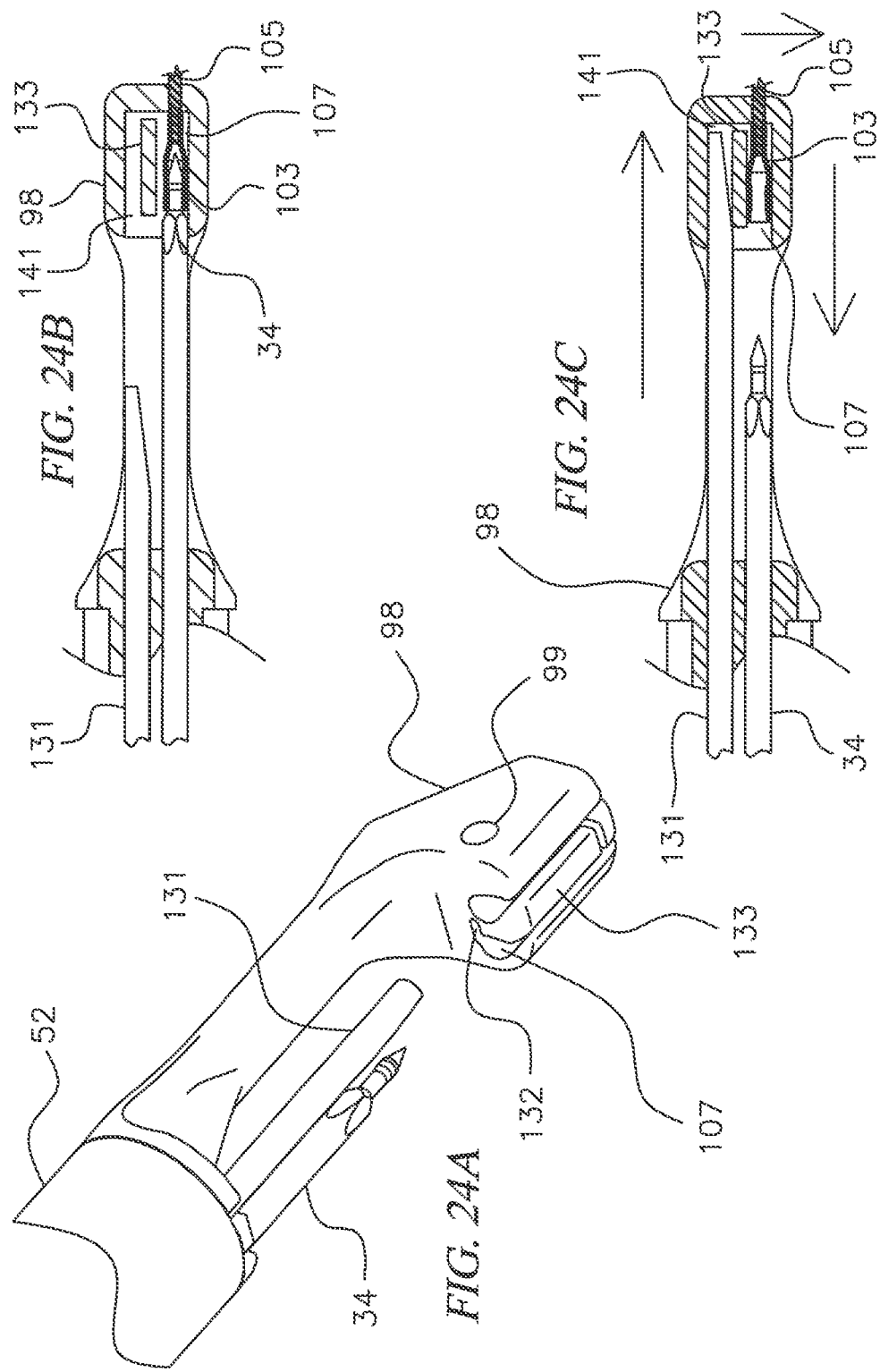

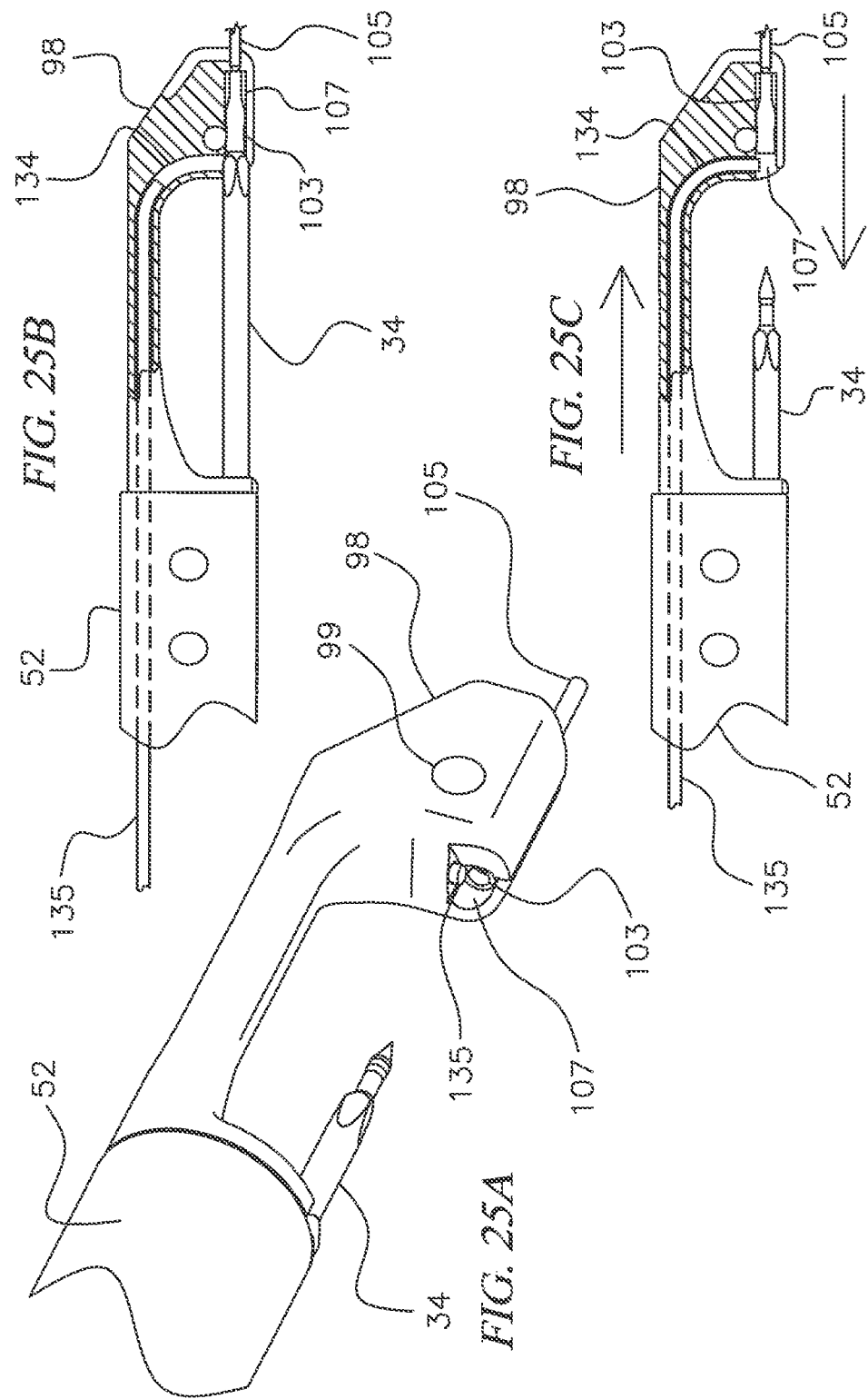

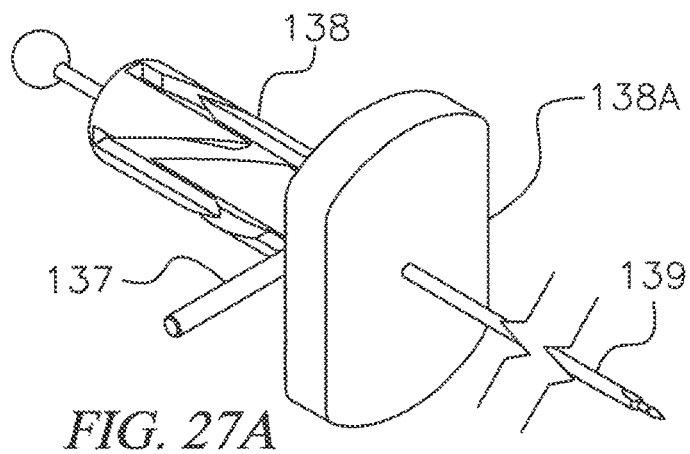
*FIG. 27A*
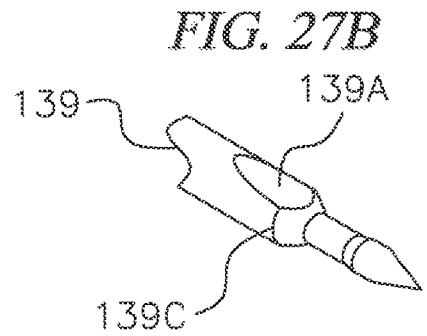
*FIG. 27B*
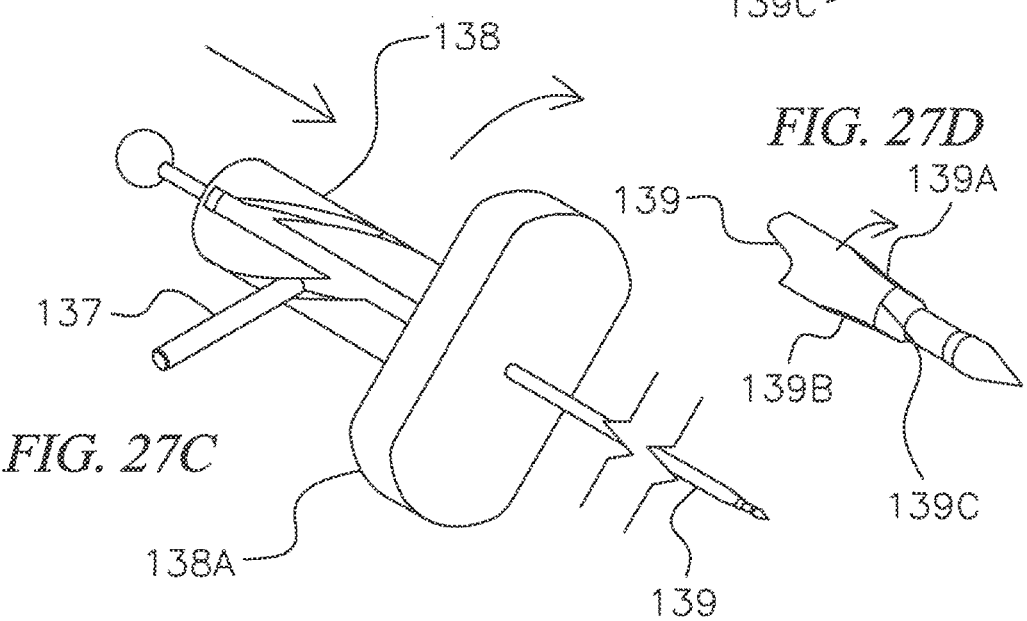
*FIG. 27C*
*FIG. 27D*
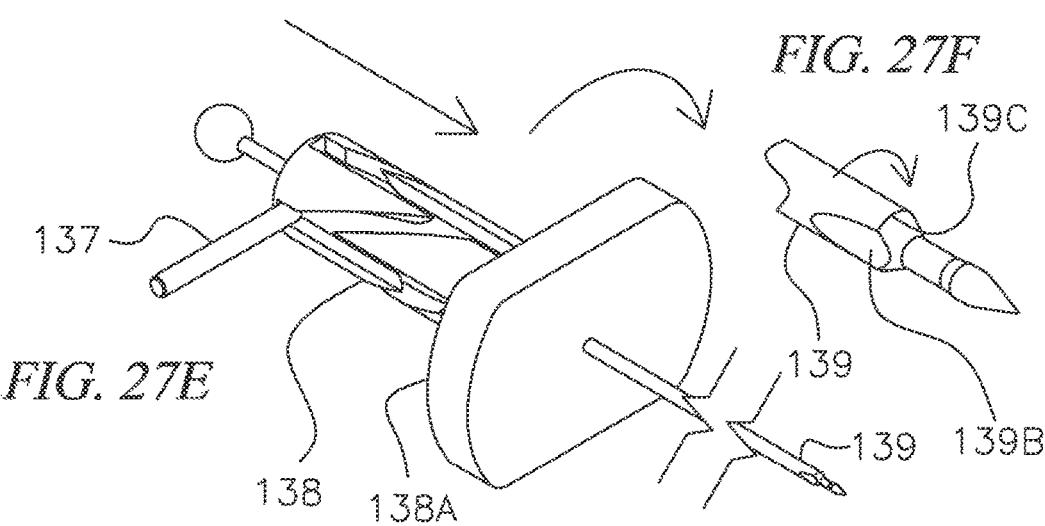
*FIG. 27E*
*FIG. 27F*

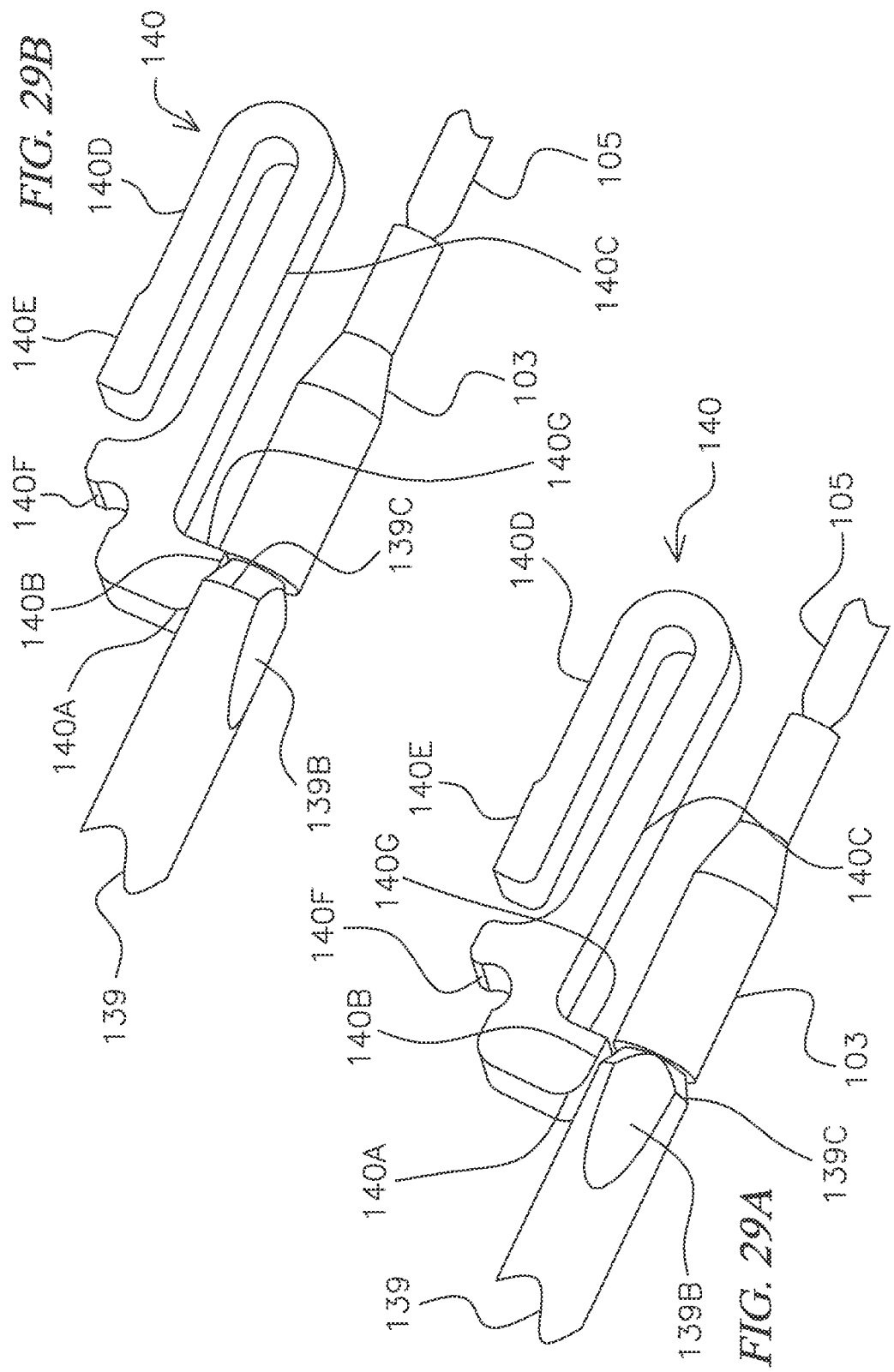

MINIMALLY INVASIVE SURGICAL SUTURING DEVICE WITH IMPROVED VISUALIZATION

CROSS-REFERENCE TO RELATED APPLICATIONS

This patent application claims priority to U.S. provisional patent application Ser. No. 62/092,222, entitled "MINIMALLY INVASIVE SURGICAL TOOLS AND METHODS THEREOF", and filed on Dec. 15, 2014.

FIELD

The claimed invention relates to surgical suturing devices, and more specifically to surgical suturing devices suitable for use in minimally invasive surgical procedures, such as, but not limited to minimally invasive cardiac surgeries.

BACKGROUND

Invasive therapeutic interventions typically provide for the removal of problematic tissue structures from the body followed by a need to reconstruct the involved tissues. Many alternatives are available for reconstructive interventions. Bandages can often close external wounds. The use of sutures placed within wound edges to draw tissues together to permit enhanced healing has become commonplace in modern medicine. Metallic or plastic staples and clips also can be used to appose tissue for healing.

To minimize the invasiveness of therapeutic procedures, efforts to create smaller access wounds that minimize iatrogenic tissue disruption have led to better patient outcomes. For example, a minimally invasive surgical procedure, like an aortic valve replacement performed through a minithoracotomy and aortotomy can facilitate less peri-operative pain, more rapid return of normal functions, and earlier return to home and work. The placement of sutures during such minimally invasive surgery can be slow, tedious and often hard to visualize. Existing specialized instruments for minimally invasive surgery have recognized limitations. Therefore, it would be desirable to have minimally invasive surgical suturing device with improved visualization.

SUMMARY

A suturing device is disclosed. The suturing device has a guide tip. The guide tip has first and second framing arms that define a viewing port from a first orientation. The guide tip also has proximal and distal ends of the guide tip which, with the first and second framing arms, define a tissue bite area from a second orientation. The suturing device also has a ferrule holder located in the distal end of the guide tip and centered relative to the first orientation. The suturing device further has a needle movable within the guide tip along a path through the tissue bite area and centrally viewable in the viewing port relative to the first orientation.

Another suturing device is disclosed. The suturing device has a shaft having a proximal and a distal end, wherein the shaft comprises a bend such that the shaft has a first longitudinal axis on one side of the bend and a second longitudinal axis on a second side of the bend. The suturing device also has a guide tip coupled to the distal end of the shaft. The guide tip has first and second framing arms that define a viewing port such that the first longitudinal axis and the second longitudinal axis lie in a plane which is substantially centered in the viewing port. The guide tip also has proximal and distal ends of the guide tip which, with the first and second framing arms, define a tissue bite area which is visible through the viewing port. The suturing device further has a ferrule holder located in the distal end of the guide tip. The suturing device also has a needle movable within the guide tip along a path through the tissue bite area and centrally viewable in the viewing port.

A further suturing device is disclosed. The suturing device has a guide tip defining a viewing port and a tissue bite area. The suturing device also has a needle movable within the guide tip along a path through the tissue bite area and centrally viewable in the viewing port.

BRIEF DESCRIPTION OF THE DRAWINGS

FIGS. 4A-4C are perspective views of the thumb slide holder of FIG. 3 showing this component from the top left, top right and bottom right perspectives, respectively.

FIG. 5A is a partially exploded perspective view of the thumb slide mechanism of FIG. 3 highlighting the thumb button and the retaining lock features.

FIG. 5B is a perspective view of an assembled thumb slide mechanism of FIG. 3 showing the thumb button in its fully out position.

FIG. 6A is a left perspective view of the thumb slide mechanism of FIG. 3 with its balled needle fully back and its accompanying lever fully out.

FIG. 6B is a left perspective view of the thumb slide mechanism of FIG. 3 with its balled needle fully forward and its accompanying lever fully retracted.

FIG. 7A is a right perspective view of the thumb slide mechanism of FIG. 3 with its thumb button and ferrule stripper fully back and its accompanying lever fully out.

FIG. 7B is a right perspective view of the thumb slide mechanism of FIG. 3 with its thumb button and ferrule stripper fully forward and its accompanying lever fully retracted.

FIG. 8A is an exploded perspective view of the distal tip of the instrument of FIG. 1 showing the distal tube, jaw, needle, ferrule stripper and ferrule retainer.

FIG. 8B is a perspective view of the underside of the distal tip of FIG. 1 showing the ferrule stripper alignment ramp and the ferrule holding compartment.

FIG. 9D is a side view of the proximal components of FIG. 9A showing the lever and thumb button fully out.

FIG. 9E is a right perspective view of the drive mechanism of the instrument of FIG. 3 with its thumb slide holder removed, the lever partially retracted and the thumb button fully out.

FIG. 9F is a right perspective view of the distal tip of the components of FIG. 9E with the needle partially advanced and the ferrule in its compartment.

FIG. 9G is the partial cross-sectional view of the distal tip of the components of FIG. 9E showing the ferrule in its compartment, the needle partially advanced and the ferrule stripper fully back.

FIG. 9H is a side view of the proximal components of FIG. 9E showing the lever partially retracted and the thumb button fully out.

FIG. 9J is a right perspective view of the drive mechanism of the instrument of FIG. 3 with the thumb slide holder removed, the lever fully retracted and the thumb button fully out.

FIG. 9K is a right perspective view of the distal tip of the components of FIG. 9J showing the needle fully advanced and engaging the ferrule in its compartment.

FIG. 9L is a partial cross-sectional view of the distal tip of the components of FIG. 9J with the needle engaging the ferrule in its compartment and the ferrule stripper fully back.

FIG. 10A is a right perspective view of the drive mechanism of the instrument of FIG. 3 with the thumb slide holder removed, with the thumb button fully out, the lever partially forward and the needle attached to the ferrule and suture partially back.

FIG. 10B is a right perspective view of the distal tip of the components of FIG. 10A showing the needle attached to the ferrule with suture partially retracted.

FIG. 10C is a partial cross-sectional view of the distal tip of the components of FIG. 10A showing the needle attached to the ferrule and suture partially retracted and the ferrule stripper fully back.

FIG. 10D is a side view of the proximal components of FIG. 10A showing the lever partially back and the thumb button fully out.

FIG. 10E is a right perspective view of the drive mechanism of the instrument of FIG. 3 with the thumb slide holder removed, the lever fully out and the thumb button fully out.

FIG. 10F is a right perspective view of the distal tip of the components of FIG. 10E showing the needle attached to the ferrule and suture fully retracted and the ferrule stripper fully back.

FIG. 10G is a perspective side view of the distal tip of the components of FIG. 10E showing the needle attached to the ferrule and suture fully retracted and the ferrule stripper fully back.

FIG. 10H is a side view of the proximal components of FIG. 10E showing the lever fully out and the thumb button fully out.

FIG. 11A is a right perspective view of the drive mechanism of the instrument of FIG. 3 with the thumb slide holder removed, the lever partially retracted, the needle with its ferrule and suture partially advanced and the thumb button fully out.

FIG. 11B is a right perspective view of the distal tip of the components of FIG. 11A showing the needle attached to the ferrule and the suture partially advanced.

FIG. 11C is a partial cross-sectional view of the distal tip of the components of FIG. 11A showing the needle attached to the ferrule and the suture partially advanced and the ferrule stripper fully back.

FIG. 11D is a side view of the proximal components of FIG. 11A showing the lever partially retracted and the thumb button fully out.

FIG. 11E is a right perspective view of the drive mechanism of the instrument of FIG. 3 with the thumb slide holder removed and the lever fully retracted and the thumb button fully out.

FIG. 11F is a right perspective view of the distal tip of the components of FIG. 11E with the needle fully advanced along with its attached ferrule and suture.

FIG. 11G is a partial cross-sectional view of the distal tip of the components of FIG. 11E showing the needle along with its attached ferrule and suture fully advanced into the ferrule compartment.

FIG. 11H is a side view of the proximal components of FIG. 11E showing the lever fully retracted and the thumb button fully out.

FIG. 11J is a close-up side view of the lock features of the components of FIG. 11H showing the flat engagement surface of the actuating member raising the proximal spring lock to disengage it from the timing tube.

FIG. 12A is a right partial view of the drive mechanism of the instrument of FIG. 3 with the thumb slide holder removed, the lever fully retracted, the needle with its attached ferrule and suture fully advanced and the thumb button partially advanced.

FIG. 12B is a right perspective view of the distal tip of the components of FIG. 12A showing the needle with its ferrule and suture fully advanced into the ferrule compartment and the ferrule stripper partially advanced.

FIG. 12C is a partial cross-sectional view of the distal tip of the components of FIG. 12A showing the needle attached to the ferrule and suture fully advanced and the ferrule stripper partially advanced.

FIG. 12D is a side view of the proximal components of FIG. 12A showing the lever fully retracted and the thumb button partially forward.

FIG. 12E is a close-up side view of the lock features of the components of FIG. 12D showing the flat engagement surface of the actuating member raising the proximal spring lock and the timing tube partially forward.

FIG. 12F is a right perspective view of the drive mechanism of the instrument of FIG. 3 with the thumb slide holder removed, the lever fully retracted, the needle with its attached ferrule and suture fully advanced, and the thumb button and ferrule stripper fully forward.

FIG. 12G is a right perspective view of the distal end of the components of FIG. 12F showing the needle with its ferrule and suture fully advanced and the ferrule stripper fully advanced and engaging the ferrule.

FIG. 12H is a partial cross-sectional view of the distal tip of the components of FIG. 12F showing the needle attached to the ferrule and the suture and the ferrule stripper fully advanced engaging the ferrule.

FIG. 12J is the side view of the proximal components of FIG. 12F showing both the lever and the thumb button fully forward.

FIG. 12K is a close-up side view of the lock features of FIG. 12J showing the flat engagement surface of the actuating member raising the proximal spring lock, the timing tube fully forward and engaging the released distal spring lock.

FIG. 13A is a right perspective view of the drive mechanism of the instrument of FIG. 3 with the thumb slide holder removed, the lever partially released, the needle partially retracted, the ferrule stripper engaging the ferrule in its ferrule compartment and the thumb button fully forward.

FIG. 13B is a right perspective view of the distal tip of the components of FIG. 13A showing the needle partially retracted and the ferrule stripper fully forward.

FIG. 13C is a partial cross-sectional view of the distal tip of the components of FIG. 13A showing the needle partially retracted and the ferrule stripper fully forward engaging the ferrule in its compartment.

FIG. 13D is a side view of the proximal components of FIG. 13A showing the lever partially out and the thumb button fully forward.

FIG. 13E is a close-up side view of the lock features of FIG. 13D showing the convex engagement surface of the actuating member raising the distal spring lock and the thumb button released but still fully forward.

FIG. 13F is a right perspective view of the drive mechanism of the instrument of FIG. 3 with the thumb slide holder removed, the lever, needle, thumb button and ferrule stripper partially back.

FIG. 13G is a right perspective view of the distal tip of the components of FIG. 13F with the needle and ferrule stripper partially retracted and the ferrule back into its compartment.

FIG. 13H is a partial cross-sectional view of the distal tip of the components of FIG. 13F showing the needle and the ferrule stripper partially back and the ferrule and suture in the ferrule compartment.

FIG. 13J is a side view of the proximal components of FIG. 13F showing the lever and the thumb button partially back.

FIG. 13K is a close-up side view of the lock features of FIG. 13F showing the engagement surfaces of the actuating member not raising either of the spring locks.

FIG. 13L is a right perspective view of the drive mechanism of the instrument of FIG. 3 with the thumb slide holder removed, the lever, needle, thumb button and ferrule stripper fully back and the ferrule and suture reloaded into the ferrule compartment.

FIG. 13M is a perspective view of the distal tip of the components of FIG. 13L showing the needle and ferrule stripper fully retracted and the ferrule and suture in the ferrule compartment.

FIG. 13N is a partial cross-sectional view of the distal tip of the components of FIG. 13L showing the needle and ferrule stripper fully back and the ferrule and suture in the ferrule compartment.

FIG. 13P is a side view of the proximal components of FIG. 13L showing the lever and the thumb button fully back.

FIG. 13R is a close-up side view of the lock features of FIG. 13L showing the proximal spring clip engaging the timing tube.

FIGS. 14A-14E show an example of the suturing procedure using the tissue suturing instrument of FIG. 1 for placement of suture at the first site of the wound closure.

FIGS. 15A-15E show an example of the suturing procedure using the tissue suturing instrument of FIG. 1 for placement of suture at the second site of the wound closure.

FIGS. 16A-16D show an example of the suturing procedure using the tissue suturing instrument of FIG. 1 for placement of suture at the third site of the wound closure.

FIGS. 17A-17D show an example of the suturing procedure using the tissue suturing instrument of FIG. 1 for placement of suture at the fourth site of the wound closure.

FIGS. 18A-18E show an example of the use of the instrument of FIG. 1 to enable suture loop construction to initiate the tying of a suture knot.

FIGS. 19A-19F show an example of the instrument of FIG. 1 to construct further suture loops used to secure a suture knot.

FIGS. 23A-23D illustrate a running suturing procedure created using the tissue suturing instrument of FIG. 1 being secured by bolsters and a crimped sleeve member.

FIG. 24A is a perspective view of the distal tip of the second example of the tissue suturing instrument of FIG. 1 in which a stripper wedge causes a flexible member to grasp the ferrule.

FIG. 24B is a partial cross-sectional view of the distal tip of the second example of the tissue suturing instrument of FIG. 1 showing the needle engaging the ferrule and partial deployment of the stripper wedge.

FIG. 24C is a partial cross-sectional view of the distal tip of the second example of the tissue suturing instrument of FIG. 1 showing the stripper wedge engaging the flexing member which grasps the ferrule and allows the needle to retract leaving the ferrule in its ferrule compartment.

FIG. 25A is a perspective view of the distal tip of the third example of the tissue suturing instrument of FIG. 1 in which a stripper rod passes through the distal tip and engages the proximal face of the ferrule to enable stripping.

FIG. 25B is a broken-out section of the distal tip of the third example of the tissue suturing instrument of FIG. 1 in which a stripper rod rests in its internal chamber as the needle engages the ferrule in its ferrule pocket.

FIG. 25C is a broken-out section of the distal tip of the third example of the tissue suturing instrument of FIG. 1 in which the stripper rod protrudes from its internal chamber to engage the proximal face of the ferrule as the needle disengages the ferrule and retracts.

FIG. 27A is a close-up isometric view of the cam and follower mechanism of the fourth example of the tissue suturing instrument of FIG. 1 illustrating the needle fully retracted.

FIG. 27B is a close-up perspective view of the tip of faceted needle of the fourth example of the tissue suturing instrument of FIG. 1 shown in its ferrule engaging configuration.

FIG. 27C is a close-up isometric view of the cam and follower mechanism of the fourth example of the tissue suturing instrument of FIG. 1 illustrating the needle partially advanced and the follower mechanism actuating the cam and rotating the needle.

FIG. 27D is a close-up perspective view of the tip of faceted needle shown partially rotated as it is advancing.

FIG. 27E is a close-up isometric view of the cam and follower mechanism of the fourth example of the tissue suturing instrument of FIG. 1 illustrating the needle fully advanced.

FIG. 27F is a close-up perspective view of the tip of faceted needle of the fourth example of the tissue suturing instrument of FIG. 1 shown fully advanced and rotated to its ferrule stripping configuration.

1 showing a partially advanced faceted needle, the ferrule in its ferrule compartment and a ferrule latch adjacent to the ferrule pocket.

Figure 1:
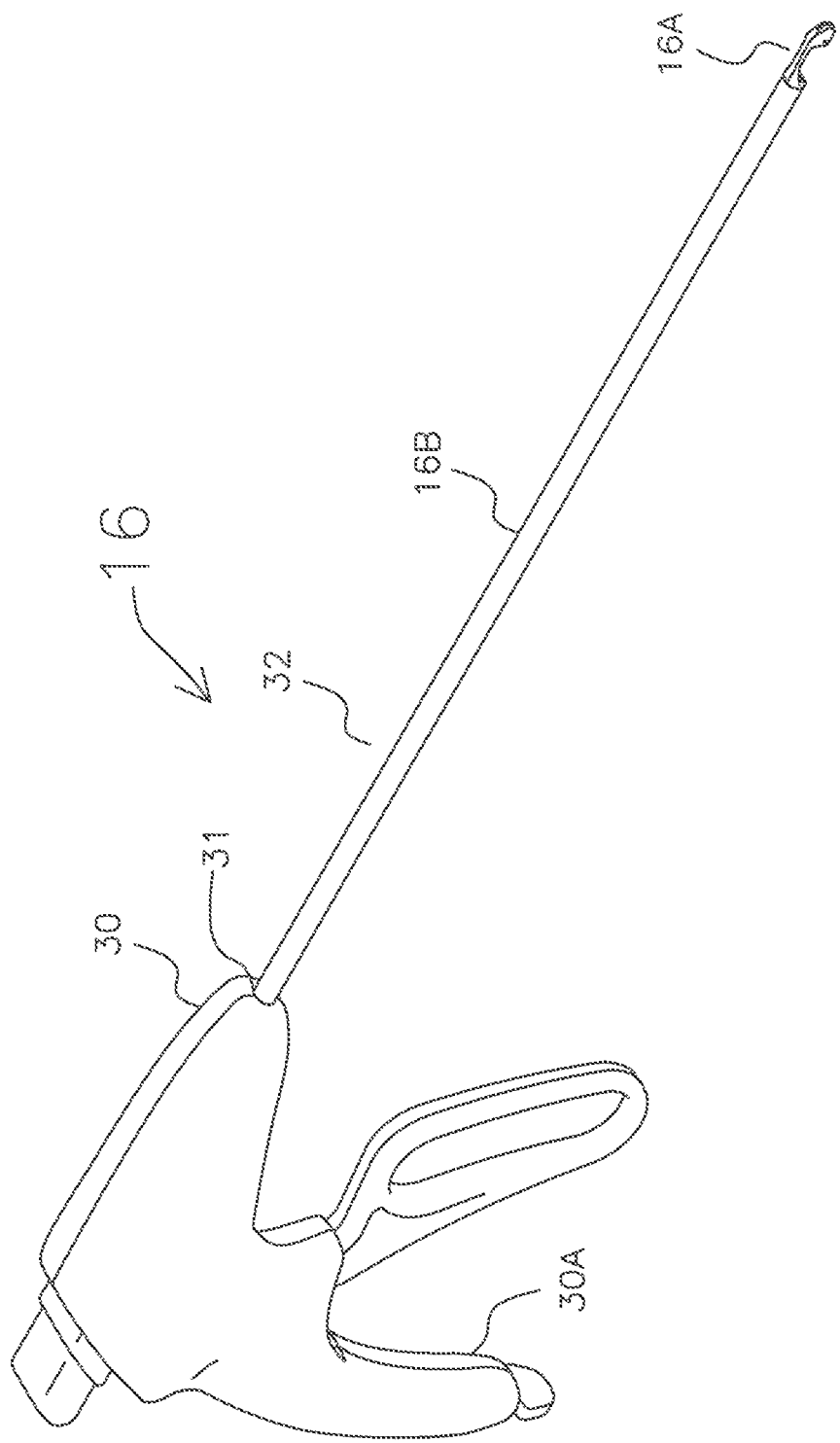
FIG. 1 is a perspective view of a tissue suturing instrument.

FIG. 29A is a close-up perspective view of the stripping mechanism of the fourth example of the tissue suturing instrument of FIG. 1 showing the ferrule latch disengaged and allowing the faceted needle to retrieve the ferrule.

FIG. 29B is a close-up perspective view of the stripping mechanism of the fourth example of the tissue suturing instrument of FIG. 1 showing the ferrule latch engaged and enabling the stripping of the faceted needle from the ferrule.

Figure 30A:
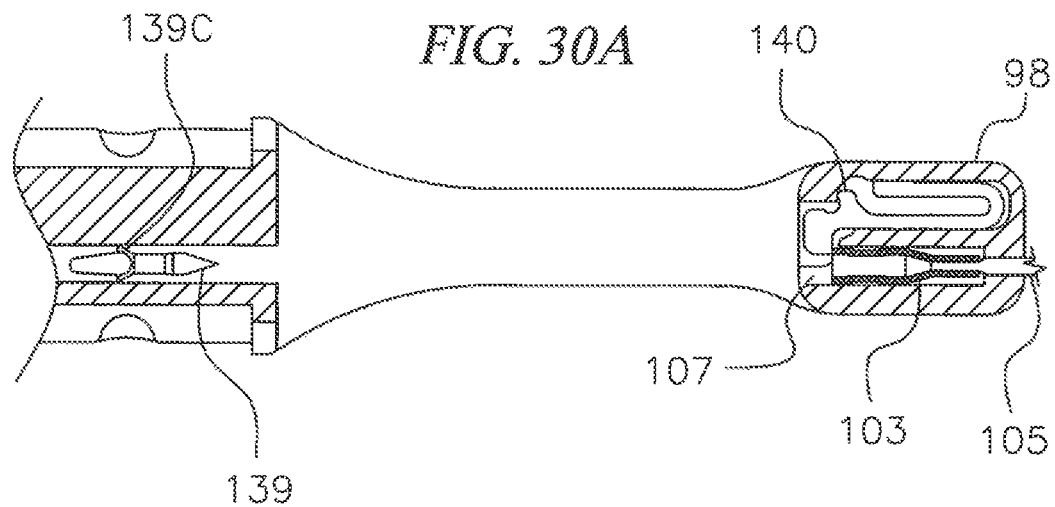

FIG. 30A is a partial cross-sectional view of the distal tip of the fourth example of the tissue suturing instrument of FIG. 1 showing the faceted needle fully retracted and the ferrule in its ferrule compartment.

Figure 30B:
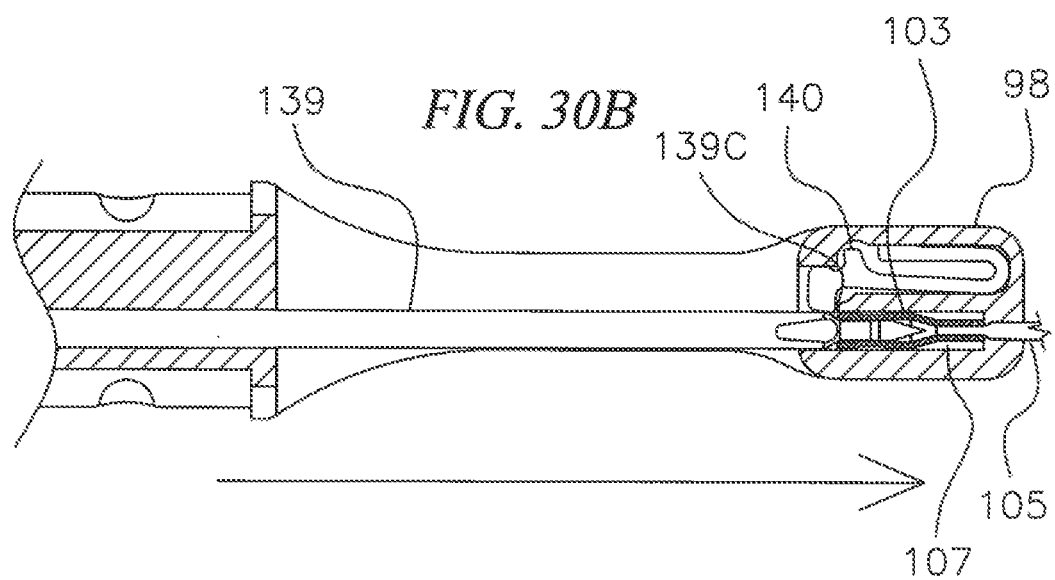

FIG. 30B is a partial cross-sectional view of the distal tip of the fourth example of the tissue suturing instrument of FIG. 1 showing the faceted needle fully extended, disengaging the ferrule latch, and connecting with the ferrule in its ferrule compartment.

Figure 30C:
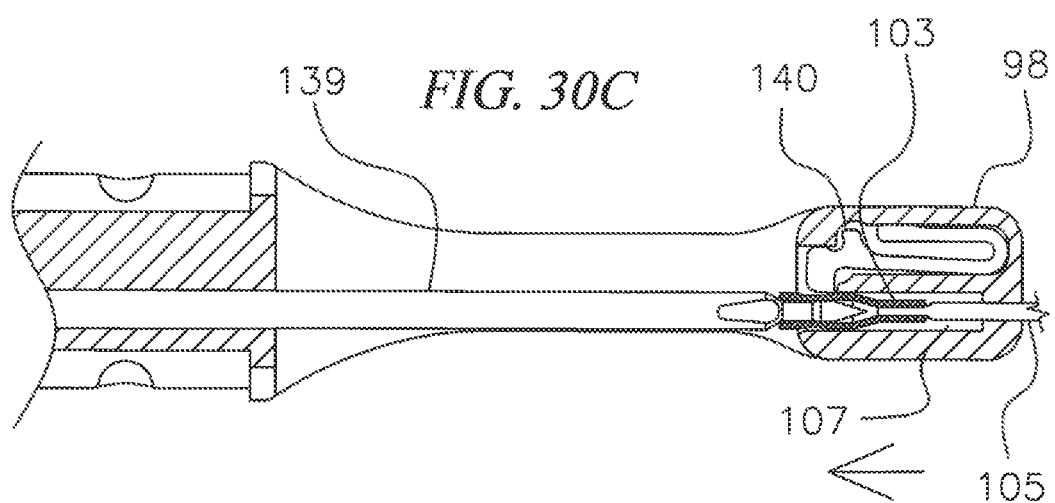

FIG. 30C is a partial cross-sectional view of the distal tip of the fourth example of the tissue suturing instrument of FIG. 1 showing the faceted needle beginning to retract with its attached ferrule and suture.

Figure 30D:
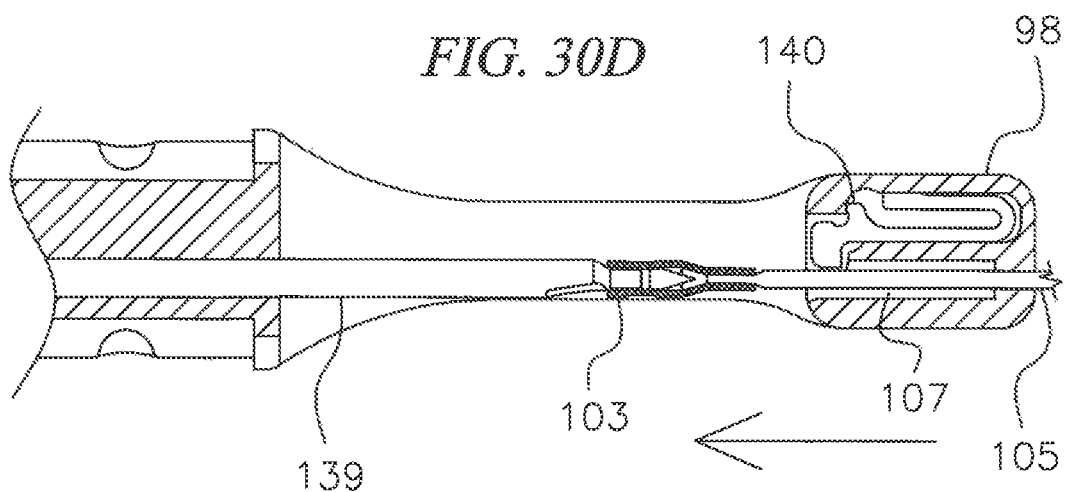

FIG. 30D is a partial cross-sectional view of the distal tip of the fourth example of the tissue suturing instrument of FIG. 1 showing the faceted needle retracting with its attached ferrule and suture and the ferrule latch returning to its normal state.

Figure 30E:
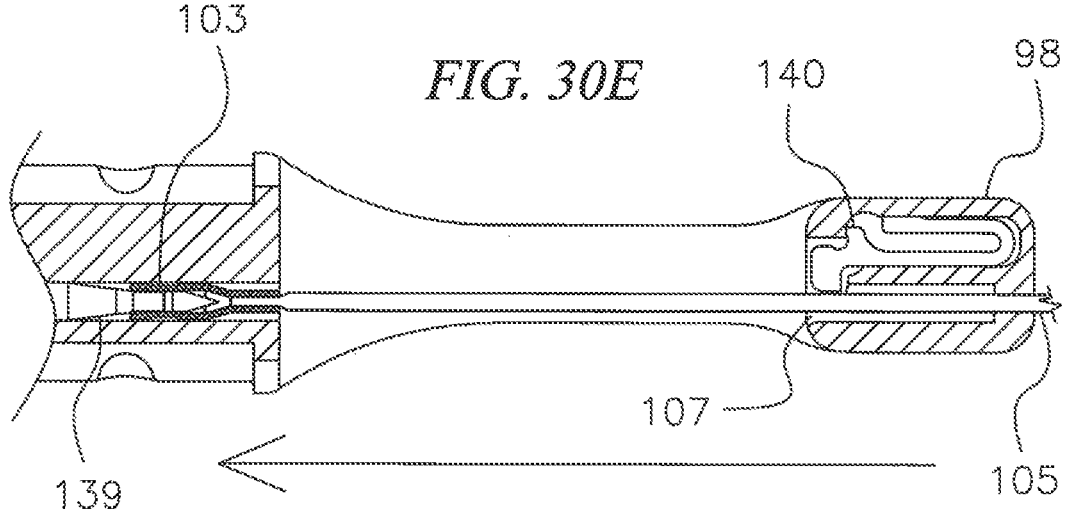

FIG. 30E is a partial cross-sectional view of the distal tip of the fourth example of the tissue suturing instrument of FIG. 1 showing the faceted needle fully retracted with its attached ferrule and suture.

Figure 30F:
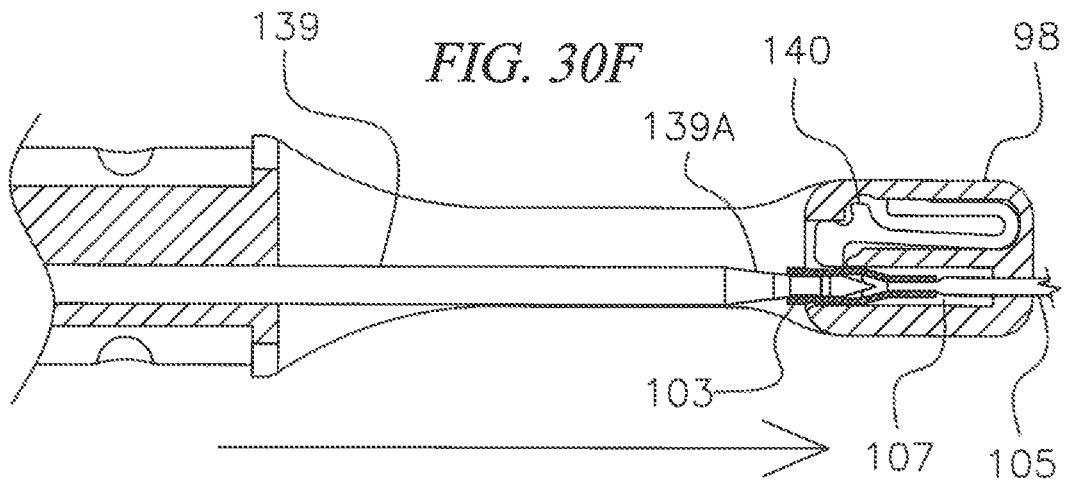

FIG. 30F is a partial cross-sectional view of the distal tip of the fourth example of the tissue suturing instrument of FIG. 1 showing the faceted needle extending and returning the ferrule and its suture to the ferrule compartment.

Figure 30G:
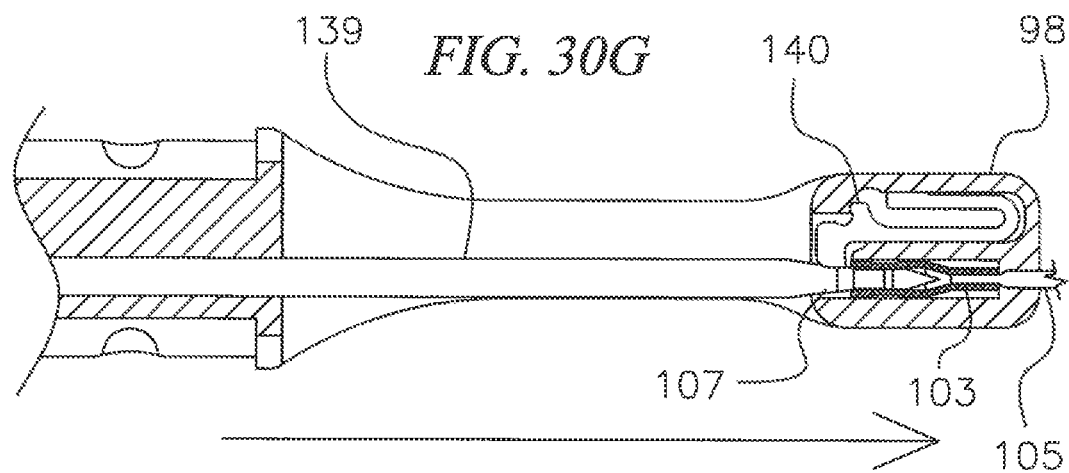

FIG. 30G is a partial cross-sectional view of the distal tip of the fourth example of the tissue suturing instrument of FIG. 1 showing the faceted needle fully extended, the ferrule and its suture returned to the ferrule compartment and the ferrule latch engaged with the proximal face of the ferrule.

Figure 30H:
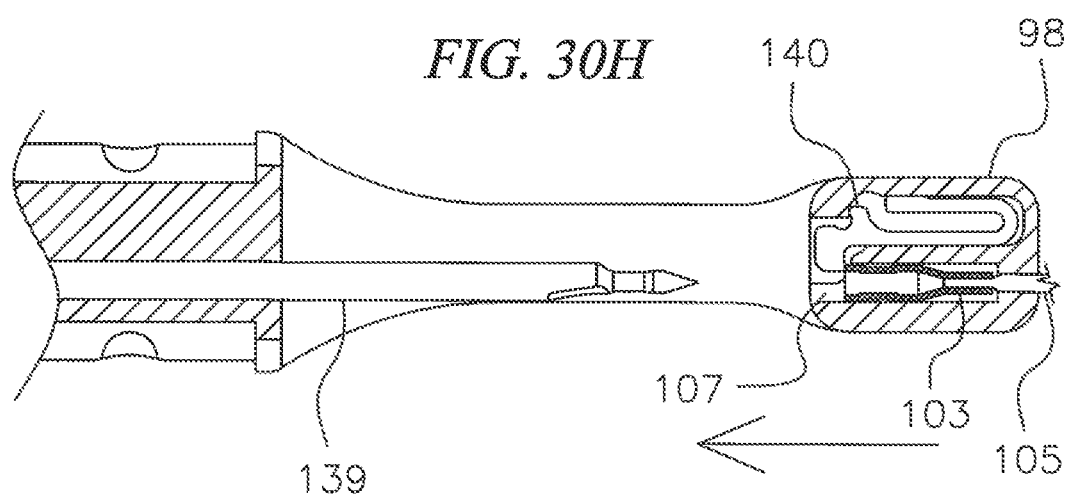
Figure 30I:
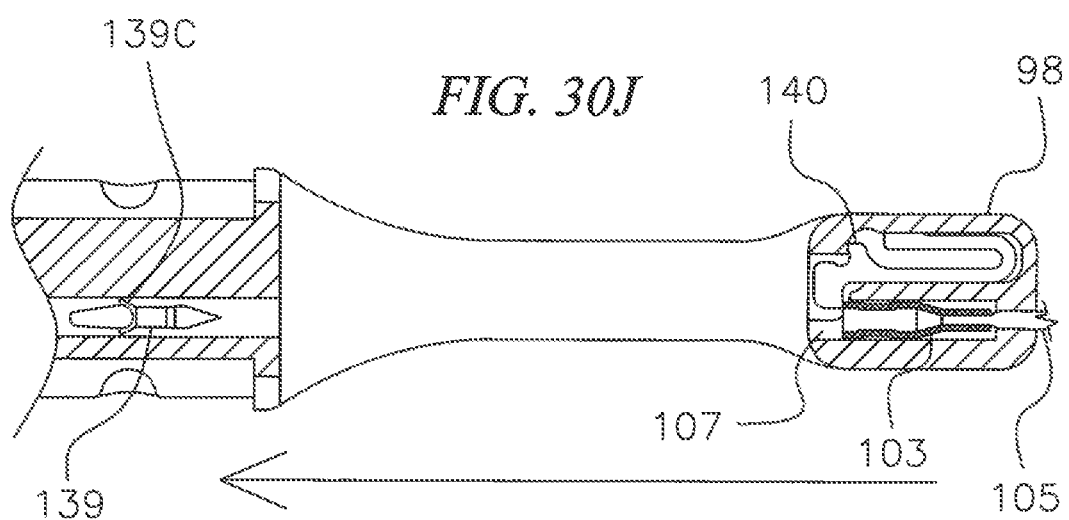

FIG. 30H is a partial cross-sectional view of the distal tip of the fourth example of the tissue suturing instrument of FIG. 1 showing the faceted needle retracting and the ferrule latch retaining the ferrule in its ferrule compartment.

FIG. 30J is a partial cross-sectional view of the distal tip of the fourth example of the tissue suturing instrument of FIG. 1 showing the faceted needle fully retracted and awaiting the next cycle of firing of the instrument.

Figure 31:
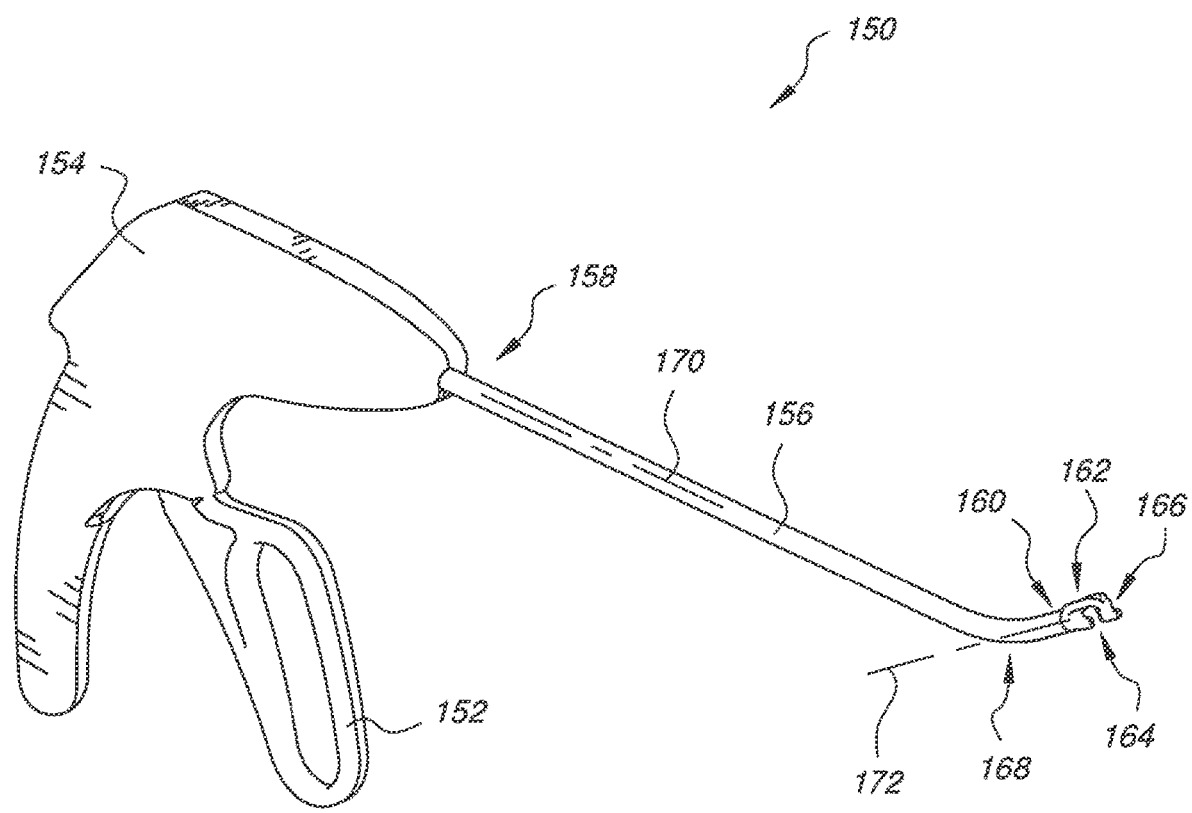

FIG. 31 illustrates a perspective view of one embodiment of an improved surgical suturing device.

Figure 32A:
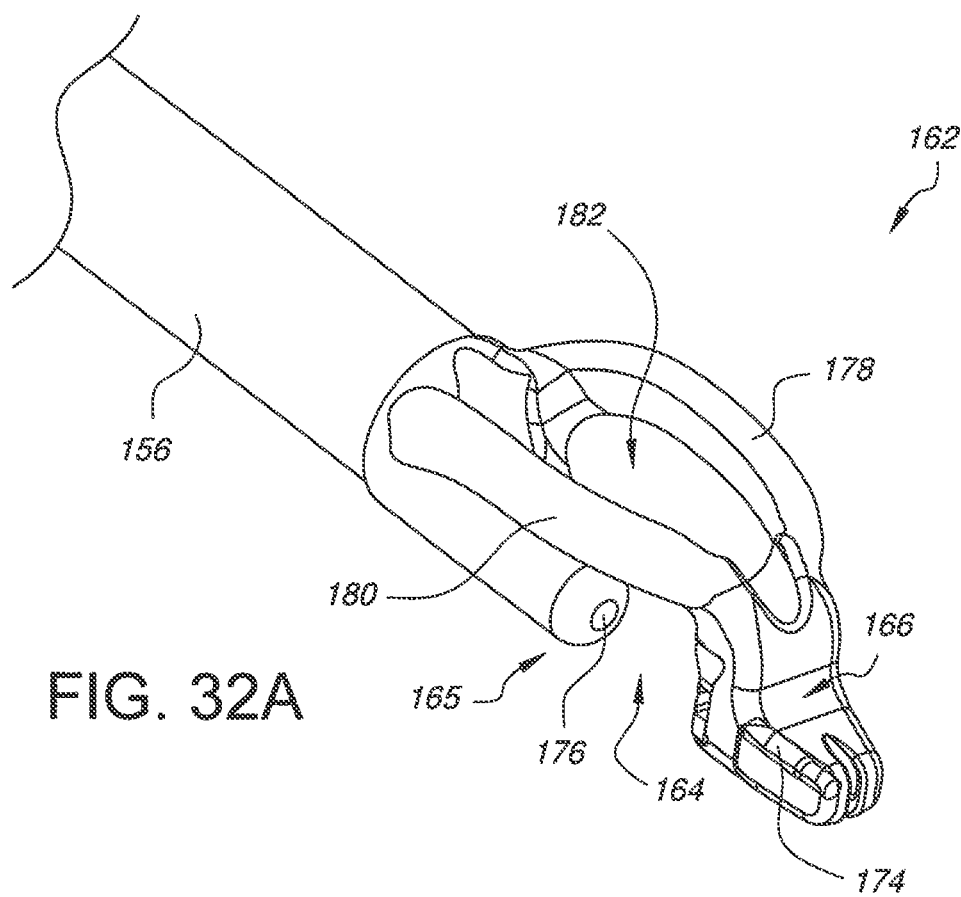
Figure 32B:
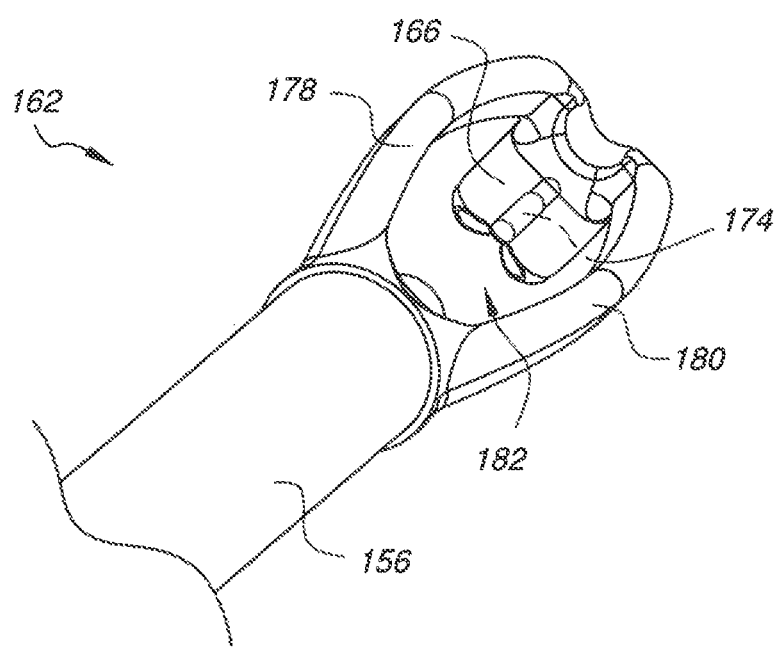

FIGS. 32A and 32B are enlarged perspective views of the guide tip of the surgical suturing device of FIG. 31 shown from differing perspectives.

Figure 33A:
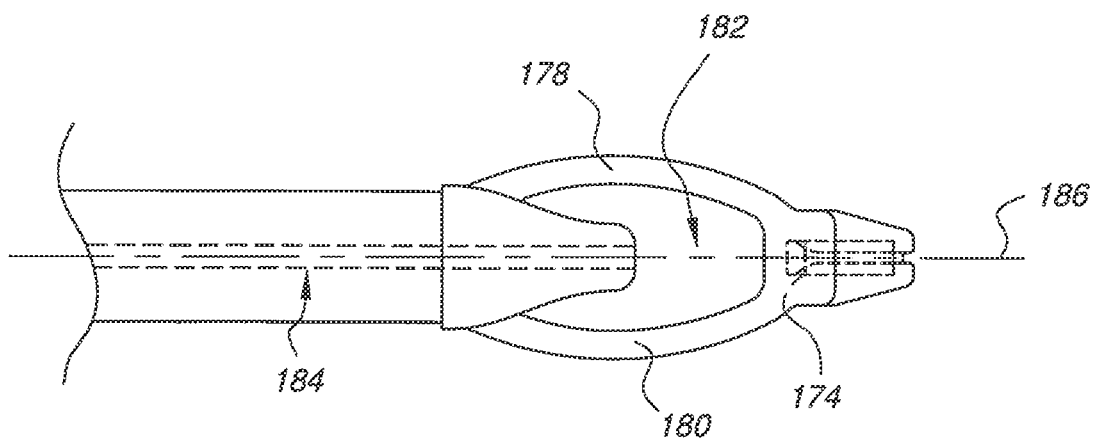
Figure 33B:
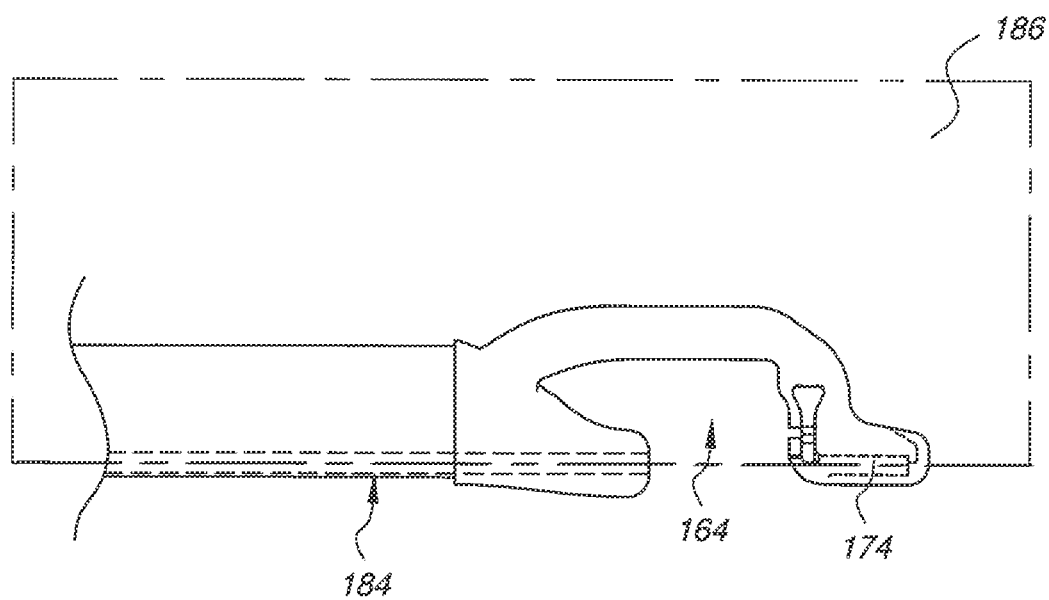

FIGS. 33A and 33B are top and side views, respectively, of the guide tip of the surgical suturing device of FIG. 31.

Figure 34:
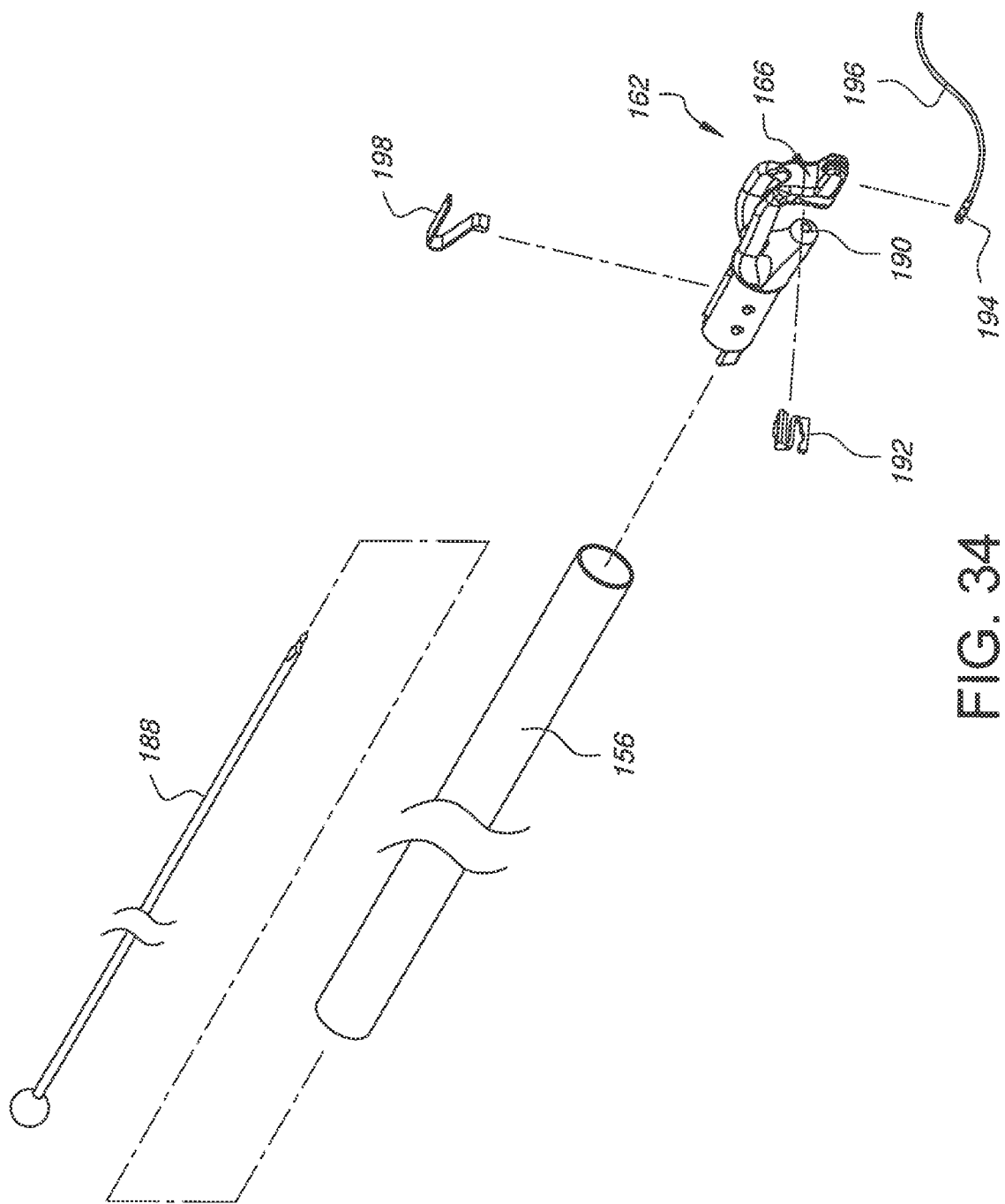

FIG. 34 is an exploded view of a distal portion of the device of FIG. 32A.

FIGS. 35A-35H schematically illustrate one possible usage of the embodied device of FIG. 32A.

It will be appreciated that for purposes of clarity and where deemed appropriate, reference numerals have been repeated in the figures to indicate corresponding features, and that the various elements in the drawings have not necessarily been drawn to scale in order to better show the features.

DETAILED DESCRIPTION

Figure 2:
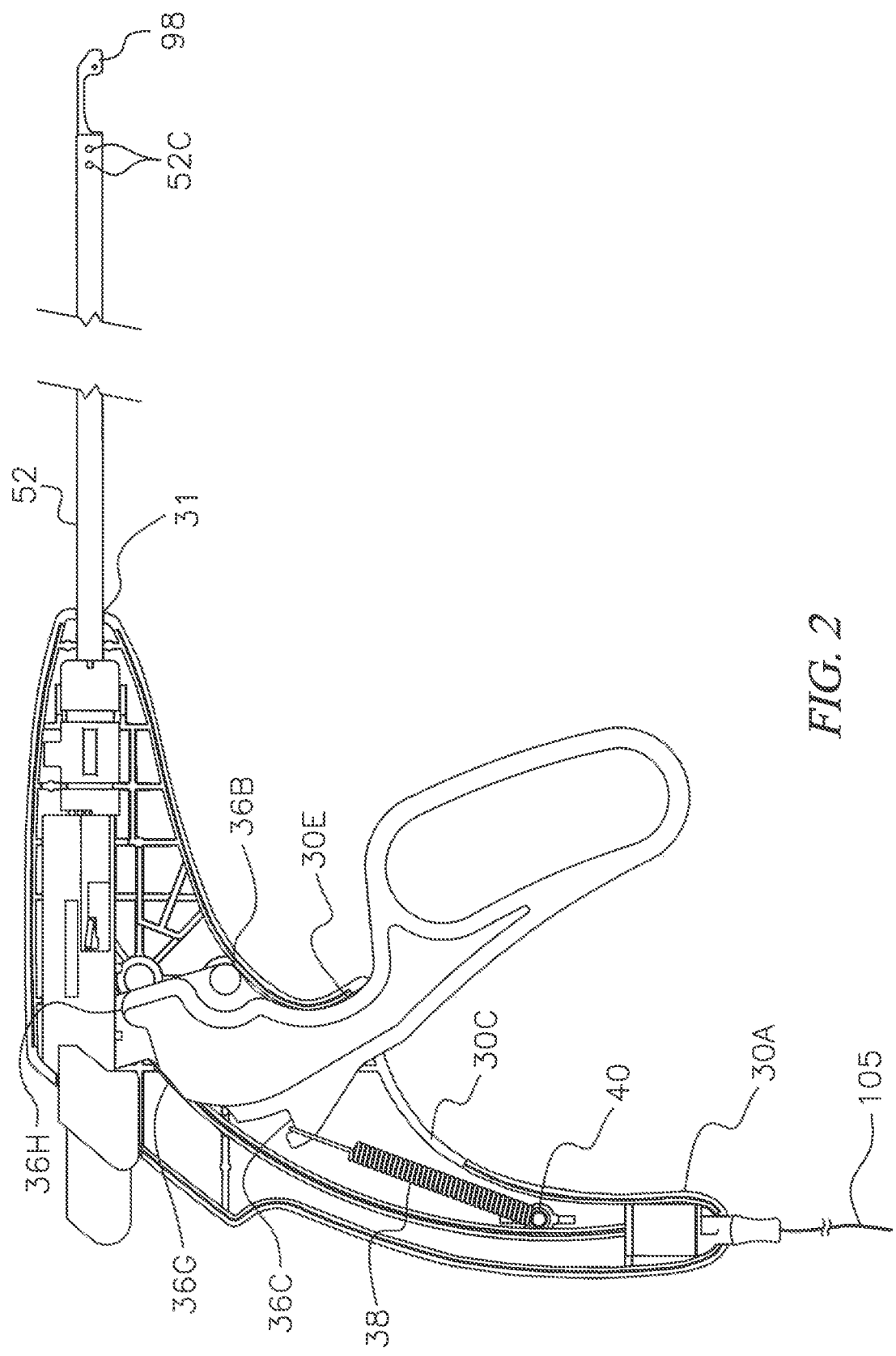
FIG. 2 is a partial side view of the tissue suturing instrument of FIG. 1 in which the right cover of the housing of the instrument is removed.
Figure 3:
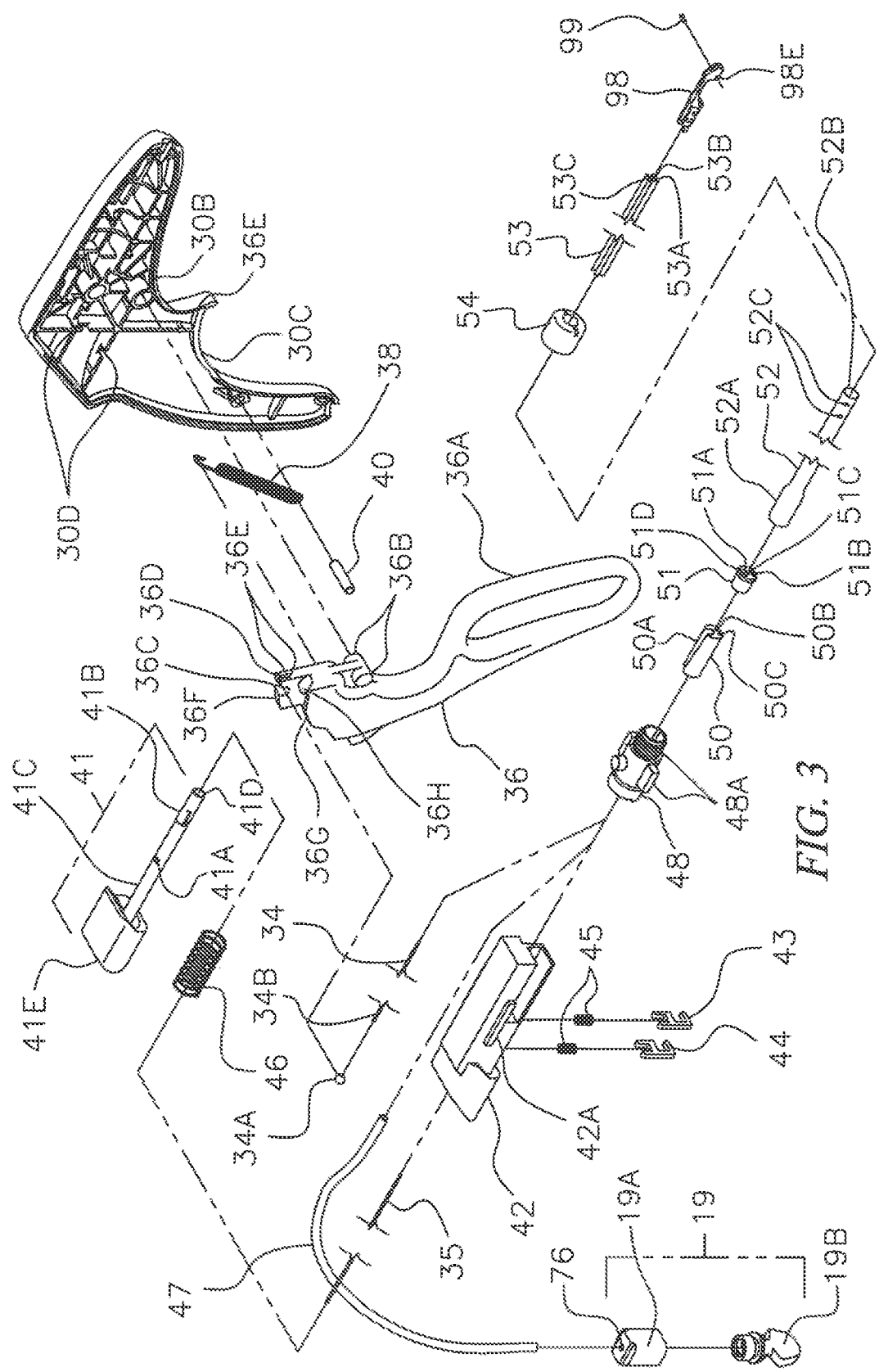
FIG. 3 is an exploded perspective view of the tissue suturing instrument of FIG. 1 in which the right cover of the housing is removed.

One example of a suturing instrument 16, is represented in FIGS. 1-13R. FIGS. 1-3, show the suturing instrument 16, which represents the SEW-RIGHT® SR•5® device manufactured by LSI SOLUTIONS, Inc. of Victor, N.Y., that has been modified to provide a means for selectably stripping its ferrule 103 from the needle 34 at its tissue engaging end 16a. The tissue engaging end 16a and needle 34 thereto may be similar to that shown in U.S. Pat. Nos. 5,431,666, 5,766,183, European Patent No. EP 0669101, filed Feb. 23, 1995 and granted Oct. 14, 1998, or U.S. patent application Publication No. US 2002/0107530 A1, filed Feb. 2, 2001, which are herein incorporated by reference.

The housing 30 has a body shaped like a pistol having a handle portion 30a, and may be made of a two-piece construction of molded plastic. A needle 34 extends from housing 30 through the shaft 16b into the tissue engaging end 16a. Needle 34 has a non-tissue engaging end 34b in the housing 30 having a spherical member 34a, such as a ball or bearing, respectively, attached thereto. The needle 34 and spherical member 34a may be made of metal, such as surgical stainless steel. The spherical member 34a may have a bore into which the non-tissue engaging end 34b of the needle 34 extends and joins thereto, such as by welding or brazing.

The suturing instrument 16 includes an actuating member 36 representing a lever 36a having two pins 36b extending into holes 30b in the sides of housing 30 upon which the actuating member 36 is pivotally mounted in the housing 30. Actuating member 36 has a portion which extends through a lever opening 30c (FIG. 2) in housing 30 to enable pivotal movement about pins 36b. An extension spring 38 is provided which hooks at one end in a notch 36c of actuating member 36 and is wound at the other end around a pin 40 located in holes 30f in the sides of housing 30, such that the actuating member 36 is spring biased to retain actuating member 36 normally in a forward position, fully out, as shown for example in FIG. 2. The body of housing 30 has a front pivot stop 30e (FIG. 3) providing a stop that limits the pivotal movement of the actuating member 36. A notch 36c is provided in the actuating member 36 which is shaped to receive the non-engaging end of needle 34, i.e., spherical member 34a, to be driven forward by an operator pulling actuating member 36 to pivot actuating member 36 towards handle portion 30a. The groove 36d (FIG. 3) is provided by two fingers 36e into which the needle 34 near the spherical member 34a may lie.

As shown in FIGS. 4B and 4C, a thumb slide holder 42 is fixed in housing 30 by two flanges 42a above actuating member 36. As best shown in FIG. 4A, the thumb slide holder 42 has a chamber 42b with a groove 42d formed by fingers 42e which allow the needle 34 to be received in chamber 42b to restrict movement of the needle 34 when held therein. The lower surface 42f of thumb slide holder 42 is curved and faces correspondingly curved upper surface 36f of actuating member 36, such that the actuating member 36 is slidable along lower surface 42f responsive to the operator pulling the actuating member 36.

The adapter 48 has a bore extending there through in which a needle spreader 50 is located. Needle spreader 50 has two channels 50b and 50c into which needle 34 and ferrule stripper 35 are respectively located to increase the distance between the needle 34 and the ferrule stripper 35 as they extend toward thumb slide holder 42, such that the needle 34 and ferrule stripper 35 are properly aligned.

A suture routing tube 47 is provided for suture thread in housing 30. Suture routing tube 47 has one end received in a valve assembly 19, at the bottom of handle portion 30a of housing 30 and then extends through the suture routing tube notch 30d (FIG. 3) along the interior of the left side of housing 30, and a groove 50a along needle spreader 50 (FIG. 3). The other end of the suture routing tube 47 is then mounted in suture routing tube hole 51a through gasket 51. Gasket member 51 further has two holes 51b and 51c through which needle 34 and ferrule stripper 35, respectively extend. The gasket 51 may be made of medical grade rubber, such as Santoprene.

A longitudinal guide member 53 is provided multiple tracks along its length, including two tracks 53a and 53b for needle 34 and ferrule stripper 35, respectively, and a suture track 53c for suture 105 extending from opening 51a of gasket 51. The guide member 53 may be made of extruded flexible material, such as Tecoflex®. A D-tube 52 is provided which is D-shaped at one end 52a is registered into a corresponding shaped opening in adapter 48, and a threaded nut 54 having an opening which extends over D-tube 52, screws onto the end of the adapter 48 to secure D-tube 52 to housing 30. With the gasket 51 loaded first into D-tube 52, guide member 53 extends from the gasket 51 through the D-tube 52. In this manner, tracks 53a, 53b, and 53c each form a channel with the interior surface of D-tube 52. D-tube 52 may be made of stainless steel, or other rigid material, and has for example, D-tube 52 has an outside diameter of 0.203 inches. (Note for other applications, such as flexible endoscopy, this tube could be flexible.) Inside D-tube 52, gasket 51 has a ring 51d, which frictionally engages the interior surface of D-tube 52. Hole 51a of the gasket 51 is of a diameter such that the suture tube 47 tightly fits therein and provides a seal around suture tube 47. The suture tube 47 may be held in place in hole 51a by friction, but adhesive may also be used. Holes 51b and 51c are of a larger diameter than the needle 34, except for a small section of holes 51b and 51c where the diameter reduces to form flaps of gasket material which seal around needle 34 and ferrule stripper 35, respectively. This enables movement of the needle 34 and ferrule stripper 35 tube back and forth while maintaining a seal about the needle 34 and ferrule stripper 35. One feature of the gasket 51 is that it enables sealing the shaft 16b as well.

The guide member 53 is received into the D-tube 52, such that guide member 53 abuts gasket 51 and engages distal tip 98. Distal tip 98 is attached to the D-tube 52 by mechanical fastening by forming small dents 52c in the metal of the D-tube 52 with a press into recessed four pockets 98b (FIG. 3), i.e., two on each side of the distal tip 98.

An optional valve assembly 19 can be provided at the bottom of handle portion 30a, as shown in FIG. 3, having a valve seat 19a and a valve controller 19b. Valve seat 19a is composed of medical grade rubber, such as Santoprene®, and has a through hole extending into an interior chamber. A valve controller 19b composed of molded plastic, or other rigid material, has a circular section through an opening and a surface forming a cam that can be turned to select a valve fully open to intermediate partially open to a fully closed position. The suture routing tube 47 is received in hole 76 of valve seat 19a, as shown in FIG. 3, such that suture 105 material from the tube can pass through openings of the valve seat 19a and then through the valve controller 19b.

Referring to FIGS. 2 and 3, the tissue engaging end 16a of the suturing instrument 16 is shown having the distal tip 98 which is mounted in a D-tube 52, such that the front section 98a of the distal tip 98 extends from D-tube 52.

Referring to FIGS. 4A 4C, the thumb slide holder 42 is shown. The thumb slide holder 42 may be made of a one-piece construction of molded plastic. The thumb slide holder 42 is fixed in the housing 30 above the actuating member 36 by two opposing flanges 42a, as best shown in FIG. 4B.

As best represented in FIG. 4A, the thumb slide holder 42 has a chamber 42b through which the positive stop 41 b of the timing tube 41c is located. One groove 42d formed by two fingers 42e allows the needle 34 (FIG. 3) to pass through the thumb slide holder 42 through the groove 36d formed by the two fingers 36e of the actuating member 36 and enables the spherical member 34a to rest in the notch 36c of the actuating member 36. The lower curved surface 42f extends over the curved upper surface 36f of the actuating member 36 to further retain the needle 34 and spherical member 34a in the notch 36c throughout the entire range of motion of the actuating member 36.

The housing 42g of the thumb slide holder 42 is fashioned to accommodate and guide the thumb button 41e (FIG. 3). The thumb button stop 42k serves as a motion-limiting surface to prevent the thumb button 41e from traveling farther than intended. The thumb slide holder 42 has a bore 42c for the timing tube 41c (FIG. 3) is located. Contained within the housing 42g is a raised region 42h to enable alignment of the return spring 46 (FIG. 3) and resting surface 42j which seats and retains the return spring 46.

FIG. 4C shows a perspective view of the thumb slide holder 42 and timing tube stop 42l which provides a positive engagement surface for the positive stop 41b to limit the advance of the timing tube 41c. The thumb slide holder 42 may further have a channel 42p forward of the groove 42d to provide clearance for suture routing-tube 47 (FIG. 3). The body of the thumb slide holder 42 has lock spring bores 42n and spring lock channels 42m to provide for the assembly, alignment, and retaining of the lock springs 45 and distal spring lock 43 and proximal spring lock 44, respectively and best represented in FIGS. 5A and 5B.

FIG. 5A shows the push button assembly 41 interfacing with other components. The timing tube 41c is shown with the thumb button 41e attached thereto. Housed inside the thumb button 41e is the return spring 46 which serves as a return mechanism for the assembly. The ferrule stripper 35 is received into the distal opening 41 d and coupled to the timing tube 41c via an insert molding or adhesive process. The lock springs 45 are inserted into the thumb slide holder 42 and followed with the proximal spring lock 44 and the distal spring lock 43. With the proximal spring lock 44 and the distal spring lock 43 inserted in the thumb slide holder 42 and compressed, the push button assembly 41 with attached ferrule stripper 35 is inserted into the thumb slide holder 42 such that the positive stop 41b passes into the chamber 42b and the proximal spring lock engages in the spring lock engagement slot 41a. The ferrule stripper 35 continues through the adapter 48.

FIG. 5B shows a perspective view of the underside of assembled push button assembly 41, thumb slide holder 42, adapter 48, nut 54, and D-tube 52 and highlights the relative location of the proximal spring lock 44 and distal spring lock 43.

Referring to FIGS. 6A and 6B, the operation of the actuating member 36 and the needle 34 is described. As the actuating member 36 is engaged, rotating about the pins 36b, the needle 34 and the attached spherical member 34a are advanced as the spherical member 34a is in contact with the notch 36c of the actuating member 36.

FIGS. 7A and 7B illustrate the operation of the push button assembly 41 and the ferrule stripper 35. The actuating member 36 is engaged, rotating about the pins 36*b* until the flat engagement surface 36*g* comes into contact with and forces the proximal spring lock 44 out of the spring lock engagement slot 41*a* (FIG. 5A) allowing the forward motion of the push button assembly 41 and the coupled ferrule stripper 35. This forward motion is limited primarily by the engagement of distal spring lock 43 with spring lock engagement slot 41*a* (FIG. 5A). Advancement of timing tube 41*c* is also limited by engaging the adapter 48.

FIG. 8A shows the assembly of the distal tip 98 and the ferrule retainer 99 with the D-tube 52, the needle 34, and the ferrule stripper 35. The distal tip 98 has a tissue bite area 104 in a c-shaped tissue bite area 104 having two openings 98*c* at one side of the gap through which each needle 34 and ferrule stripper 35 may extend The needle 34 and the ferrule stripper 35 are received into the needle/stripper openings of the distal tip 98 and the distal tip 98 is then coupled to the D-tube 52 which may be achieved by mechanical fastening forming small dents in the metal of the D-tube 52 with a press into four recessed pockets 98*b*, i.e., two on each side of the distal tip 98. The ferrule retainer 99 is inserted into the ferrule retainer hole 98*e* until the ring 99*a* seats into the opening created where the ferrule retainer hole 98*e* intersects the ferrule pocket 107 as best shown in FIG. 8B. The suture 105 attached to the ferrule 103 enters the ferrule compartment 107 through the open slot located on the side of the ferrule chamber opposite from the ferrule retainer 99.

FIGS. 9A-13R represent highlights of twelve sequential steps overviewing the loading, reloading and locking operations through one complete cycle of use of instrument 16. For example, the first three steps presented in FIGS. 9A-9M, illustrate the needle 34 first advancing into the ferrule 103.

Figures 9A, 9B, 9C:
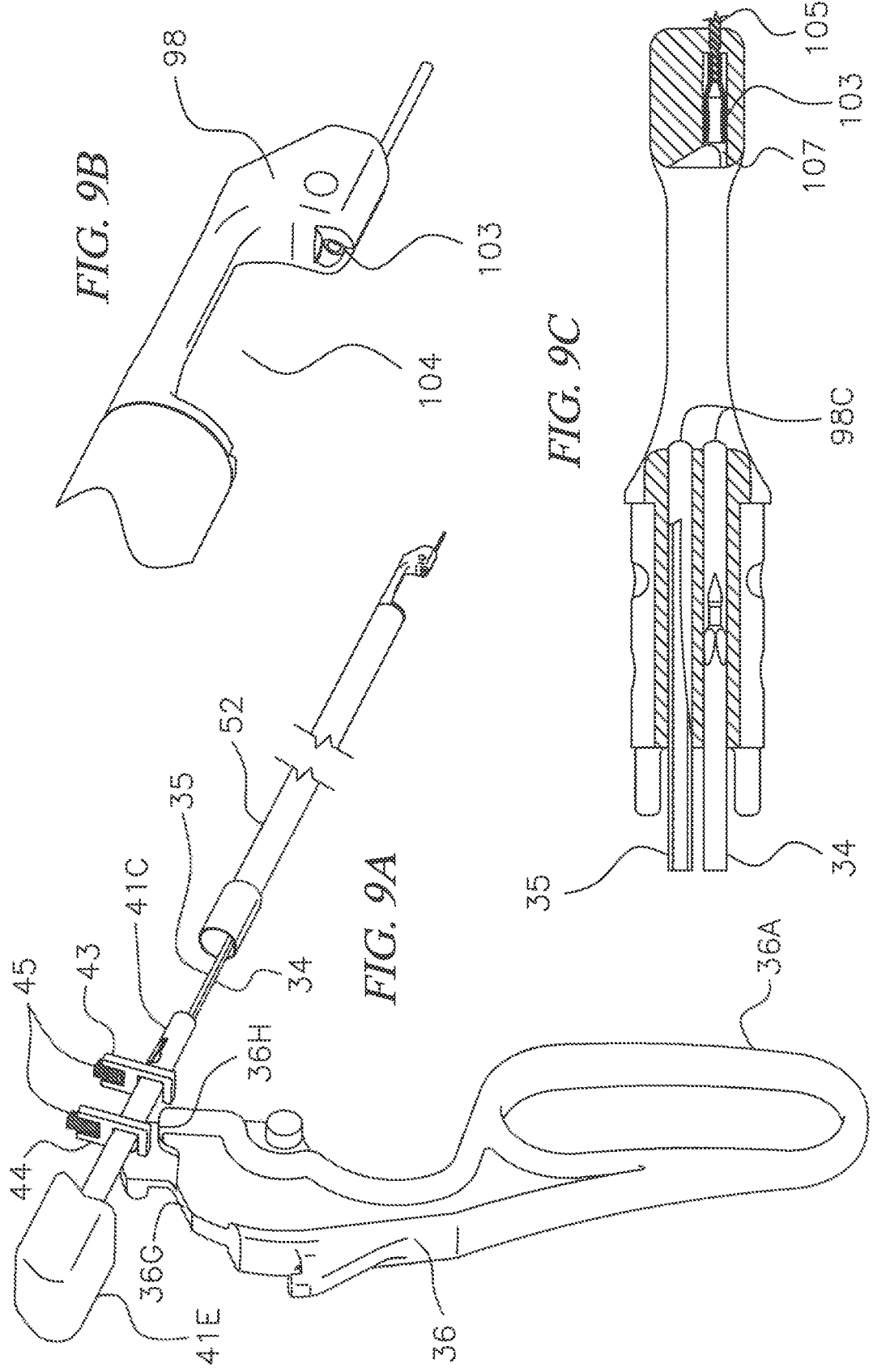
FIG. 9A is a right perspective view of the drive mechanism of the instrument of FIG. 3 with the thumb slide holder removed and both the thumb button and the lever are fully out.
FIG. 9B is a right perspective view of the distal tip of the components of FIG. 9A showing the ferrule in its compartment.
FIG. 9C is a partial cross-sectional view of the distal tip of the components of FIG. 9A with the ferrule in its compartment and the needle and ferrule stripper fully back.

FIGS. 9A-9D show the instrument loaded and ready for use, the first step. FIG. 9A shows a right perspective view of the drive mechanism of the instrument of FIG. 3 with the thumb slide holder 42 removed and both the thumb button 41*e* and the lever 36*a* are fully out; the proximal spring lock 44 engages the timing tube 41*c*. FIG. 9B is a right perspective view of the distal tip 98 of the components of FIG. 9A showing the ferrule 103 in its ferrule compartment 107 and the tissue bite area 104. FIG. 9C is a partial cross-sectional view of the distal tip 98 of the components of FIG. 9A with the ferrule 103 in its ferrule compartment 107, and the needle 34 and ferrule stripper 35 fully back. FIG. 9D is a side view of the proximal components of FIG. 9A showing the lever 36*a* and thumb button 41 fully out. Proximal spring lock 44 is shown engaging spring lock engagement slot 41*a* of timing tube 41*c*.

FIGS. 9E-9H show partial advancement of the needle 34 as part of the second step. FIG. 9E is a right perspective view of the drive mechanism of the instrument of FIG. 3 with its thumb slide holder 42 removed, the lever 36*a* partially retracted and the thumb button 41*e* fully out. FIG. 9F is a right perspective view of the distal tip 98 of the components of FIG. 9E with the needle 34 partially advanced and the ferrule 103 in its ferrule compartment 107. FIG. 9G is the partial cross-sectional view of the distal tip 98 of the components of FIG. 9E showing the ferrule 103 in its ferrule compartment 107, the needle 34 partially advanced and the stripper 35 fully back. FIG. 9H is a side view of the proximal components of FIG. 9E showing the lever 36*a* partially retracted and the thumb button 41*e* fully out.

Figure 9M:
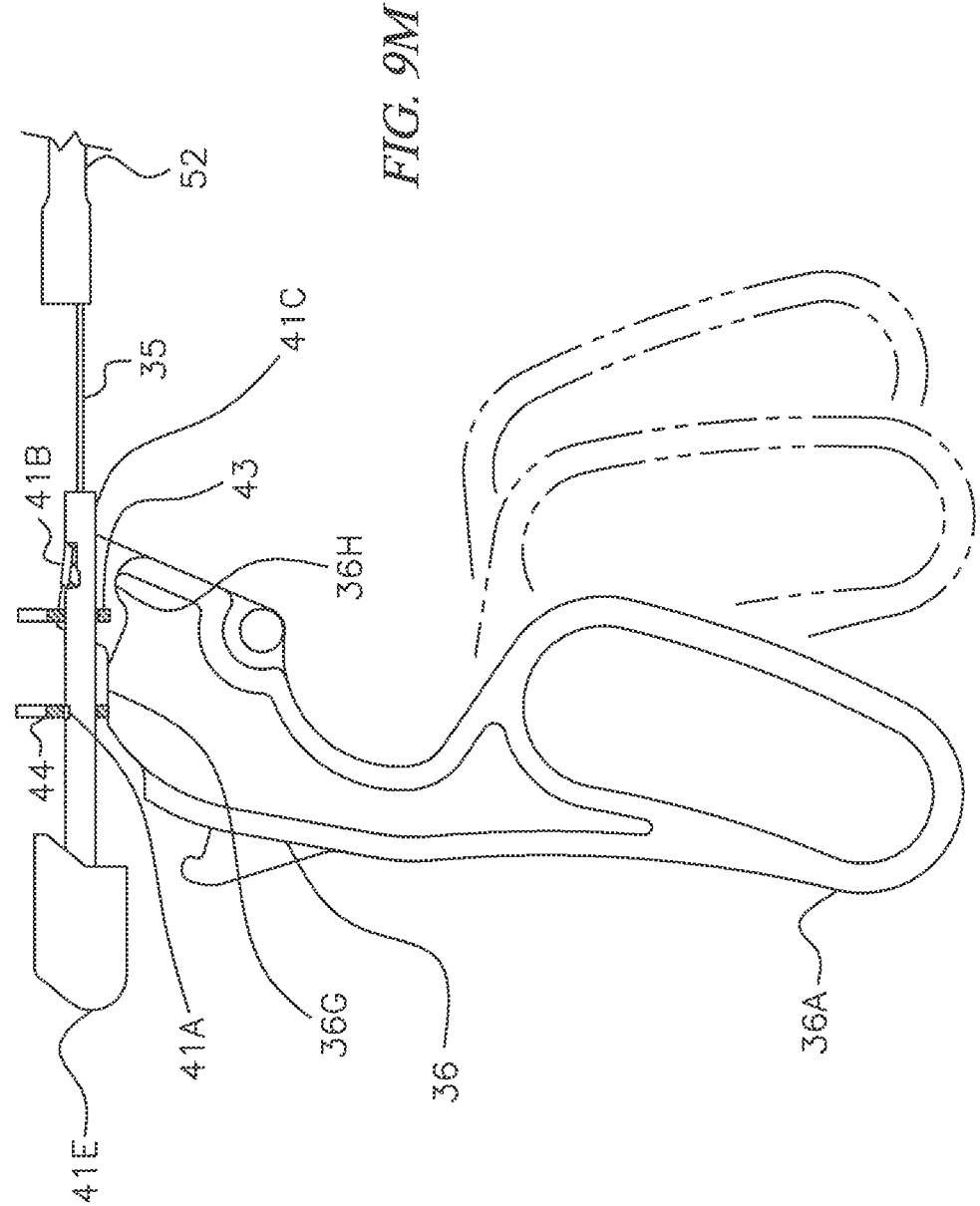
FIG. 9M is a side view of the proximal components of FIG. 9J showing the lever fully retracted and the thumb button fully out.

FIGS. 9J-9M show the needle 34 fully advanced and engaged inside of the ferrule 103 as part of the third step. FIG. 9J is a right perspective view of the drive mechanism of the instrument of FIG. 3 with the thumb slide holder 42 removed, the lever 36*a* fully retracted and the thumb button 41*e* fully out. FIG. 9K is a right perspective view of the distal tip 98 of the components of FIG. 9J showing the needle 34 fully advanced to engage the ferrule 103 in its ferrule compartment 107; best shown in FIG. 9L. FIG. 9L is a partial cross-sectional view of the distal tip 98 of the components of FIG. 9J with the needle 34 engaging the ferrule 103 in its ferrule compartment 107 and the ferrule stripper 35 fully back. FIG. 9M is a side view of the proximal components of FIG. 9J showing the lever 36*a* fully retracted and the thumb button 41*e* fully out. Note that the flat engagement surface 36*g* is shown raising the proximal spring lock 44 out of the spring lock engagement slot 41*a*.

The next two steps presented in FIGS. 10A-10H, illustrate the needle 34, now attached to the ferrule 103 and its suture 105, being retracted fully back. FIGS. 10A-10D show the needle 34 pulling its ferrule 103 back through tissue bite area 104. FIG. 10A is a right perspective view of the drive mechanism of the instrument of FIG. 3 with the thumb slide holder 42 removed, with the thumb button 41*e* fully out, the lever 36*a* partially forward and the needle 34 attached to the ferrule 103 and suture 105 partially back. FIG. 10B is a right perspective view of the distal tip 98 of the components of FIG. 10A showing the needle 34 attached to the ferrule 103 with suture 105 partially retracted. FIG. 10C is a partial cross-sectional view of the distal tip 98 of the components of FIG. 10A showing the needle 34 attached to the ferrule 103 and suture 105 partially retracted and the ferrule stripper 35 fully back. FIG. 10D is a side view of the proximal components of FIG. 10A showing the lever 36*a* partially back and the thumb button 41*e* fully out;

FIGS. 10E-10H show this instrument 16 with the ferrule 103 and its suture 105 attached to the fully retracted needle 34. FIG. 10E is a right perspective view of the drive mechanism of the instrument of FIG. 3 with the thumb slide holder 42 removed, the lever 36*a* fully out and the thumb button 41*e* fully out. FIG. 10F is a right perspective view of the distal tip 98 of the components of FIG. 10E showing the suture 105 fully retracted and the ferrule stripper 35 fully back. FIG. 10G is a perspective side view of the distal tip 98 of the components of FIG. 10E showing the needle 34 attached to the ferrule 103 and suture 105 fully retracted and the ferrule stripper 35 fully back. FIG. 10H is a side view of the proximal components of FIG. 10E showing the lever 36*a* fully out and the thumb button 41*e* fully out.

FIGS. 11A-11J show the next two steps representing reinsertion of the ferrule 103 into it ferrule compartment 107. FIGS. 11A 11E show the partial advancement of the needle 34 with its attached ferrule 103 and suture 105. FIG. 11A is a right perspective view of the drive mechanism of the instrument of FIG. 3 with the thumb slide holder 42 removed, the lever 36*a* partially retracted, the needle 34 with its ferrule 103 and suture 105 partially advanced and the thumb button 41*e* fully out. FIG. 11B is a right perspective view of the distal tip 98 of the components of FIG. 11A showing the needle 34 attached to the ferrule 103 and the suture 105 partially advanced. FIG. 11C is a partial cross-sectional view of the distal tip 98 of the components of FIG. 11A showing the needle 34 attached to the ferrule 103 and the suture 105 partially advanced and the ferrule stripper 35 fully back. FIG. 11D is a side view of the proximal components of FIG. 11A showing the lever 36*a* partially retracted and the thumb button 41*e* fully out.

FIGS. 11E-11J show the needle 34 fully advanced attached to the ferrule 103 and its suture 105. Note that at this step of the operation, FIG. 11J is provided to show an enlarged view of the distal spring lock 43 and proximal spring lock 44. FIG. 11E is a right perspective view of the drive mechanism of the instrument of FIG. 3 with the thumb slide holder 42 removed and the lever 36*a* fully retracted and the thumb button 41*e* fully out. FIG. 11F is a right perspective view of the distal tip 98 of the components of FIG. 11E with the needle 34 fully advanced into the ferrule 103. FIG. 11G is a partial cross-sectional view of the distal tip 98 of the components of FIG. 11E showing the needle 34 along with its attached ferrule 103 and suture 105 fully advanced into its ferrule compartment 107. FIG. 11H is a side view of the proximal components of FIG. 11E showing the lever 36*a* fully retracted and the thumb button 41*e* fully out. FIG. 11J is a close-up side view of the lock features of the components of FIG. 11H showing the flat engagement surface 36*g* of the actuating member 36 raising the proximal spring lock 44 to disengage it from the spring lock engagement slot 41*a* of the timing tube 41*c*.

FIGS. 12A-12K illustrate the next two steps to complete advancement of the ferrule stripper 35. FIGS. 12A-12E show the advancing of the push button assembly 41 to partially advance towards stripping the ferrule 103 from the fully advanced needle 34. FIG. 12A is a right partial view of the drive mechanism of the instrument of FIG. 3 with the thumb slide holder 42 removed, the lever 36*a* fully retracted, the needle 34 with its attached ferrule 103 and suture fully advanced and the thumb button 41*e* partially advancing the ferrule stripper 35. FIG. 12B is a right perspective view of the distal tip 98 of the components of FIG. 12A showing the needle 34 with its ferrule 103 and suture 105 fully advanced into its ferrule compartment 107 and the ferrule stripper 35 partially advanced. FIG. 12C is a partial cross-sectional view of the distal tip 98 of the components of FIG. 12A showing the needle 34 attached to the ferrule 103 and suture 105 fully advanced and the ferrule stripper 35 partially advanced.

FIG. 12D is a side view of the proximal components of FIG. 12A showing the lever 36*a* fully retracted and the thumb button 41*e* and its attached timing tube 41*c* partially forward. FIG. 12E is a close-up side view of the lock features of the components of FIG. 12D showing the flat engagement surface 36*g* raising the proximal spring lock 44 out of the spring lock engagement slot 41*a* and the timing tube 41*c* partially forward.

FIGS. 12F-12K show the full advancement of both the needle 34 and ferrule stripper 35. FIG. 12F is a right perspective view of the drive mechanism of the instrument of FIG. 3 with the thumb slide holder 42 removed, the lever 36*a* fully retracted, the needle 34 with its attached ferrule 103 and suture 105 fully advanced, and the thumb button 41*e* advancing its ferrule stripper 35 fully forward. FIG. 12G is a right perspective view of the distal end of the components of FIG. 12F showing the needle 34 with its ferrule 103 and suture 105 fully advanced and the ferrule stripper 35 fully advanced and engaging the proximal edge of the ferrule 103, as best shown in FIG. 12H. FIG. 12H is a partial cross-sectional view of the distal tip 98 of the components of FIG. 12F showing the needle 34 attached to the ferrule 103 and the suture 105 and the ferrule stripper 35 fully advanced and flexed onto the needle 34 to engage the proximal edge of the ferrule 103. FIG. 12J is the side view of the proximal components of FIG. 12F showing both the lever 36*a* and the thumb button 41*e* fully forward. FIG. 12K is a close-up side view of the lock features of FIG. 12J showing the actuating member 36 raising the proximal spring lock 44, allowing the distal spring lock 43 to engage the spring lock engagement slot 41*a* in the timing tube 41*c*.

Note a relief 36*j* in the top of the actuating member 36 allows the distal spring lock 43 to travel downward and engage the spring lock engagement slot 41*a*.

The last three steps, FIGS. 13A-13R, illustrate the complete retraction of both the needle 34 and ferrule stripper 35. FIGS. 13A-13E show the lever 36*a* partially forward to retract the needle 34 to strip the ferrule. 103 by engaging ferrule 103 with the fully advanced ferrule stripper 35. FIG. 13A is a right perspective view of the drive mechanism of the instrument of FIG. 3 with the thumb slide holder 42 removed, the lever 36*a* partially released, the needle 34 partially retracted, the ferrule stripper 35 engaging the ferrule 103 in its ferrule compartment 107 and the thumb button 41*e* fully forward.

FIG. 13B is a right perspective view of the distal tip 98 of the components of FIG. 13A showing the needle 34 partially retracted from its ferrule 103 (not visible in this view) and the ferrule stripper 35 fully forward. FIG. 13C is a partial cross-sectional view of the distal tip 98 of the components of FIG. 13A showing the needle 34 partially retracted and the ferrule stripper 35 fully forward engaging the ferrule 103 in its ferrule compartment 107. FIG. 13D is a side view of the proximal components of FIG. 13A showing the lever 36*a* partially out and the thumb button 41*e* fully forward. FIG. 13E is a close-up side view of the lock features of FIG. 13D showing the convex engagement surface 36*h* of the actuating member 36 (FIG. 13D) raising the distal spring lock 43 to disengage the spring lock engagement slot 41*a* of the timing tube 41*c*.

FIGS. 13F-13K show both the needle 34 and ferrule stripper 35 partially returning with the ferrule 103 replaced back into its ferrule compartment 107. FIG. 13F is a right perspective view of the drive mechanism of the instrument of FIG. 3 with the thumb slide holder 42 removed, the lever 36*a*, needle 34, thumb button 41*e* and ferrule stripper 35 partially back. FIG. 13G is a right perspective view of the distal tip 98 of the components of FIG. 13F with the needle 34 and ferrule stripper 35 partially retracted and the ferrule 103 back into its ferrule compartment 107. FIG. 13H is a partial cross-sectional view of the distal tip 98 of the components of FIG. 13F showing the needle 34 and the ferrule stripper 35 partially back and the ferrule 103 and suture 105 in the ferrule compartment 107. FIG. 13J is a side view of the proximal components of FIG. 13F showing the lever 36*a* and the thumb button 41*e* partially back. FIG. 13K is a close-up side view of the lock features of FIG. 13F showing the engaging surfaces 36*f* 36*h* of the actuating member 36 not raising the proximal spring lock 44 or the distal spring lock 43 with the spring lock engagement slot 41*a* released.

FIGS. 13L-13R show the instrument reloaded, ready for use and are identical to FIGS. 9A-9D, respectively, while FIG. 13R highlights re-engagement of the proximal spring lock 44 with the spring lock engagement slot 41*a*. FIG. 13L is a right perspective view of the drive mechanism of the instrument of FIG. 3 with the thumb slide holder 42 removed, the lever 36*a*, needle 34, thumb button 41*e* and ferrule stripper 35 fully back and the ferrule 103 and suture 107 reloaded into the ferrule compartment 107. FIG. 13M is a perspective view of the distal tip 98 of the components of FIG. 13L showing the needle 34 and ferrule stripper 35 fully retracted and the ferrule 103 and suture 107 in the ferrule compartment 107. FIG. 13N is a partial cross-sectional view of the distal tip 98 of the components of FIG. 13L showing the needle 34 and ferrule stripper 35 fully back and the ferrule 103 and suture 107 in the ferrule compartment. FIG. 13P is a side view of the proximal components of FIG. 13L showing the lever 36a and the thumb button 41e fully back. FIG. 13R is a close-up side view of the lock features of FIG. 13L showing the proximal spring lock 44 engaging the spring lock engagement slot 41a of the timing tube 41c.

Now referencing FIGS. 14A-17D, showing the multiple placement of sutures to form a wound closure. FIGS. 14A-14E illustrate the use of this instrument for the placement of the first suture of a wound closure and the readiment of the instrument for subsequent bites. FIG. 14A shows the distal tip 98 of the instrument 16 above a wound closure 110. Note the distal side of the wound closure 110 has crosshatching for purposes of this illustration. FIG. 14B shows the device 16 with the needle 34 passing through the first bite 124 of the distal side of the wound 110. FIG. 14C shows the needle 34 retracted back with its ferrule 103 and suture 105 pulled through the wound 110. FIG. 14D shows the needle 34 now advanced through to place the ferrule 103 back into its ferrule compartment 107. FIG. 14E shows the needle 34 back after having its ferrule 103 stripped. The instrument is now ready for another bite.

Now referencing FIGS. 15A-15E, the device 16 is again placed into the wound 110 this time with the proximal side of the wound 110 in the instrument's tissue bite area 104. The needle 34 will enter the tissue 120 as shown in FIG. 15A, traverse the tissue 120 and enter the ferrule compartment 107 as shown in FIG. 15B. FIG. 15C illustrates the needle 34, ferrule 103 and suture 107 pulled back leaving suture 105 through the first bite 126 on the proximal side of the wound closure 110. FIG. 15D shows the needle 34 advanced yet again. FIG. 15E shows the ferrule 103 back in its ferrule compartment 107.

FIG. 16A-16D shows the second suture placement on the distal side of the wound 110. FIG. 16A shows the needle 34 traversing the second site 127 on the distal wound 110 aspect. FIG. 16B shows the suture 105 through the second bite 127 on the distal side of the wound 110. FIG. 16C shows the needle 34, ferrule 103 and suture 105 advanced to the ferrule pocket. FIG. 16D shows the instrument again ready for the bite.

FIG. 17A-17D show the second bite 128 on the proximal side of the wound closure 110. FIG. 17A shows the needle 34 going through the second site 128 of the proximal side of the wound closure 110. FIG. 17B shows the needle 34, ferrule 103 and suture 105 advanced back into its ferrule compartment 107. FIG. 17C shows the instrument with the ferrule 103 reloaded and the needle 34 and ferrule stripper 35 retracted back. FIG. 17D illustrates the appearance of the wound closure 110. If the sutures 105 were to be tied at this time, this type of closure is commonly called a figure of eight suture closure. If the process were to continue with further placements of suture 105 running along the distal and proximal aspects of the wound closure, this type of closure is typically be called a running suture wound closure.

Figure 18D:
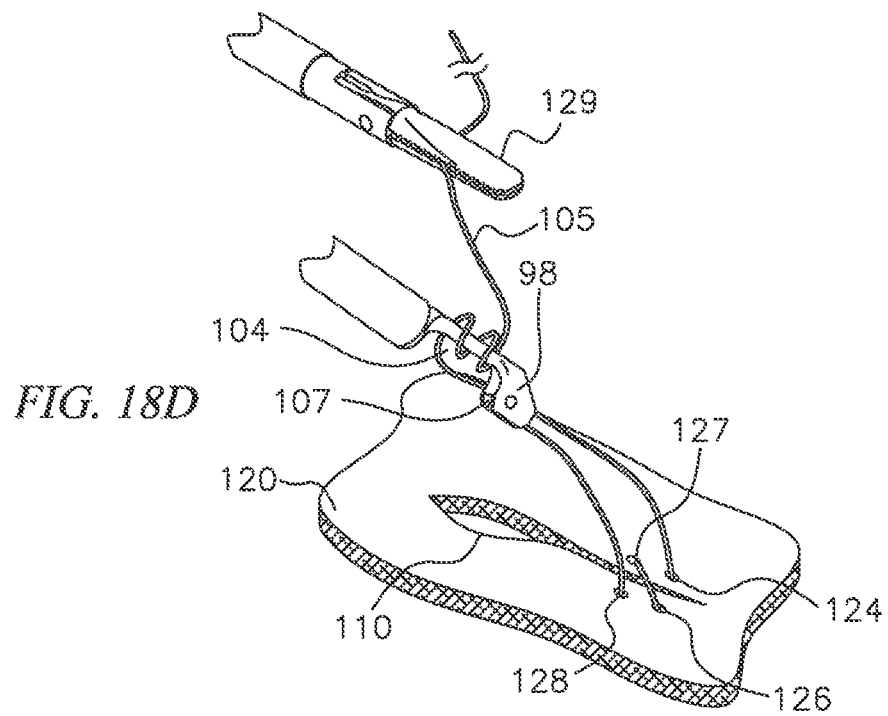
Figure 18E:
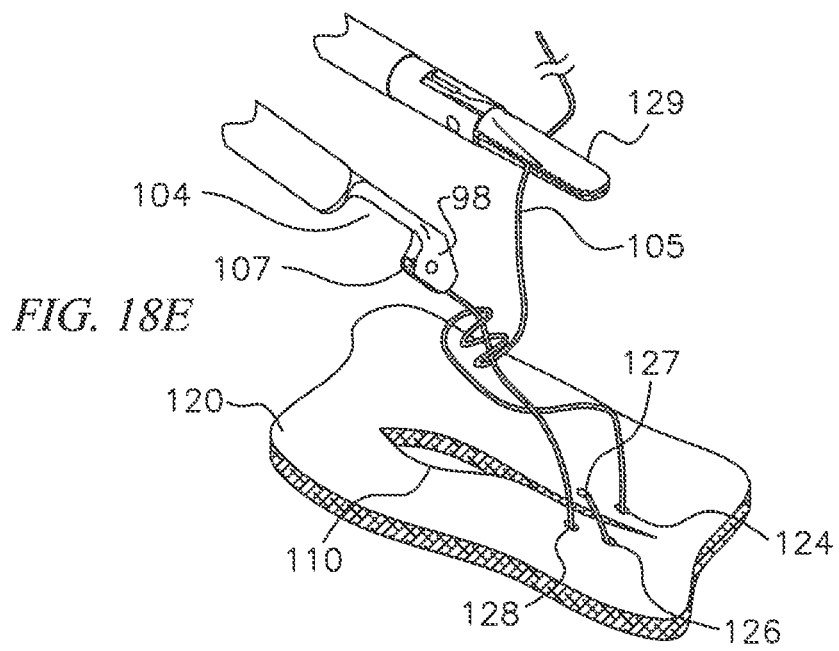
Figure 19C:
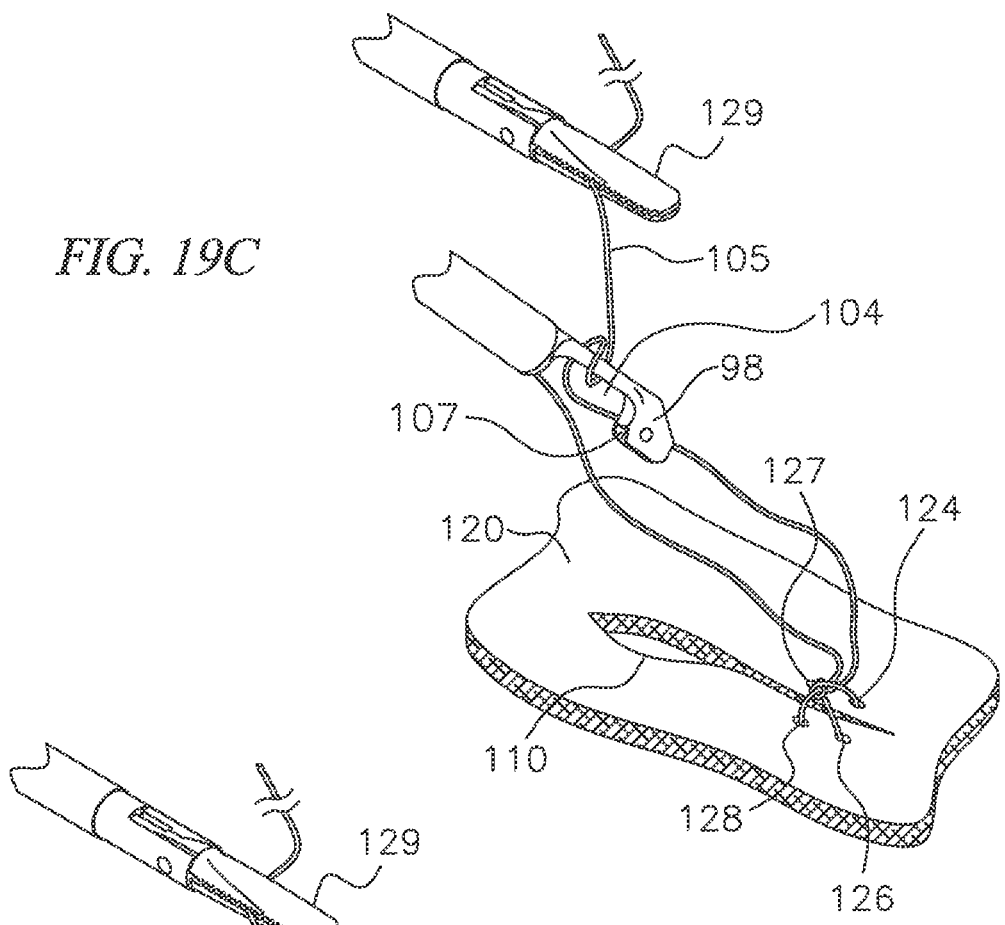
Figure 19D:
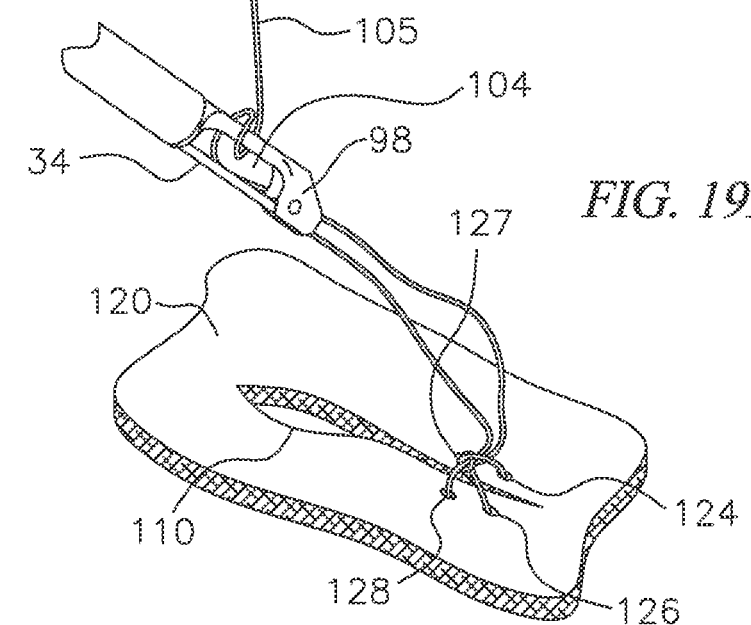
Figure 19E:
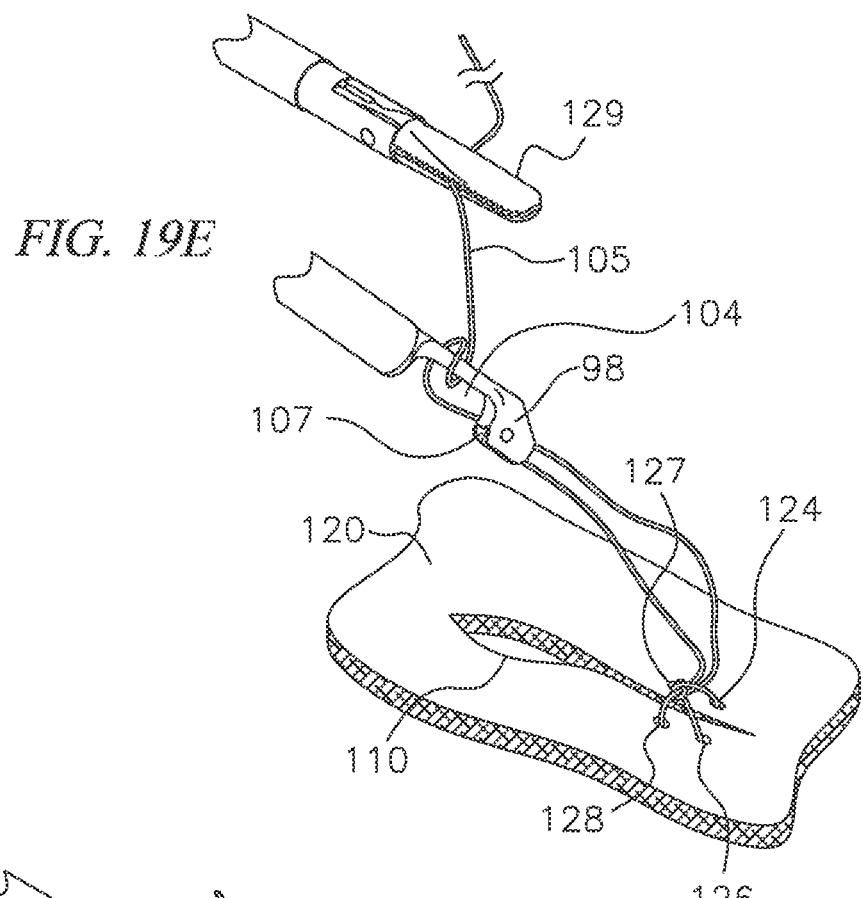
Figure 19F:
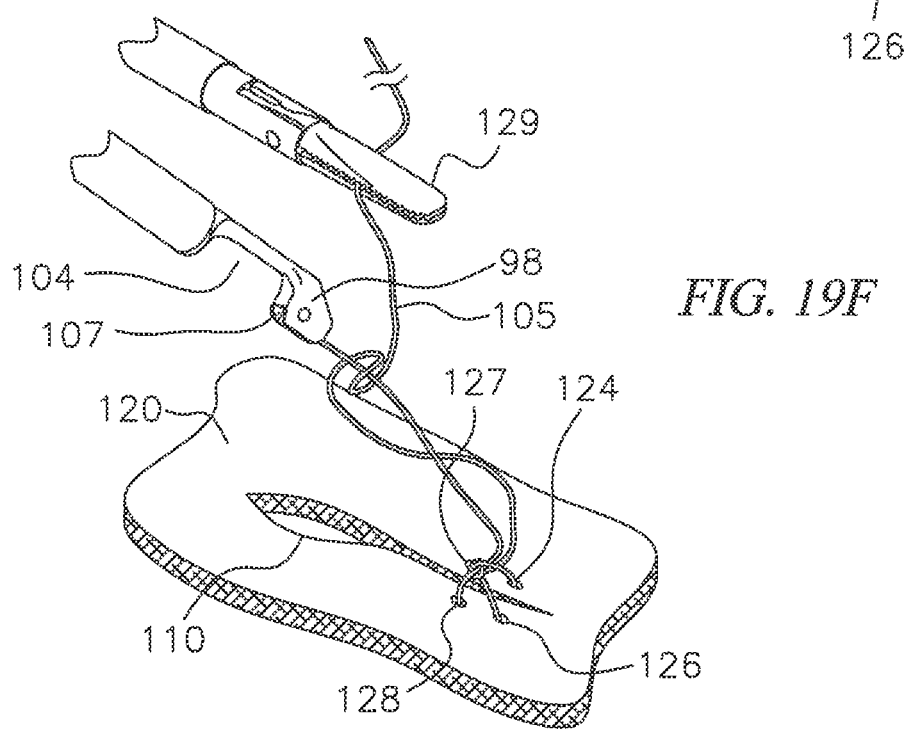
Figure 20:
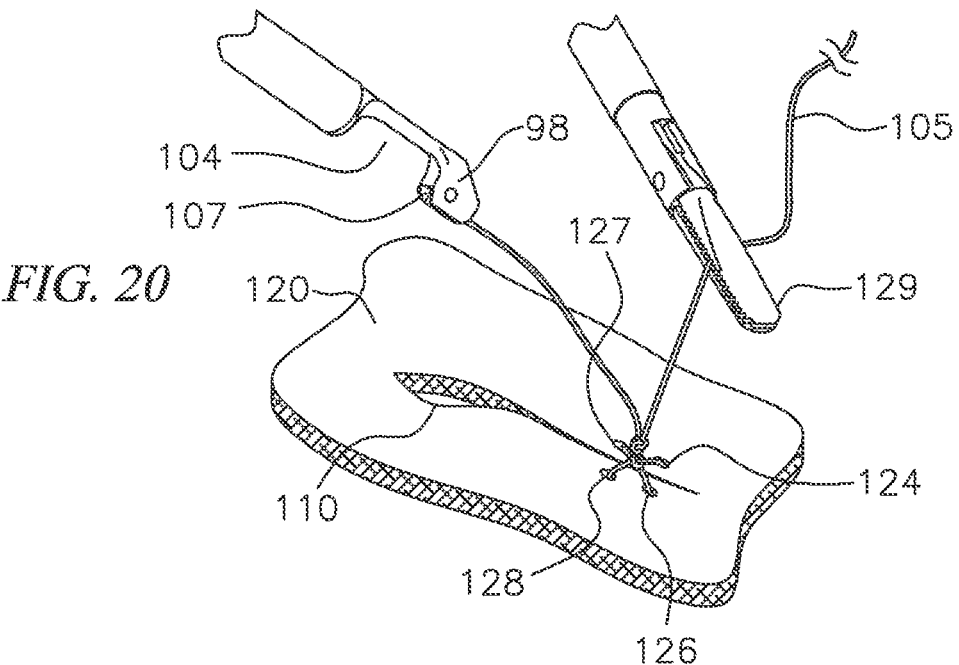
FIG. 20 shows the suturing instrument of FIG. 1 used with a surgical grasper, which pulls on the free end of the suture to deliver the suture knot to the wound closure site.
Figure 21:
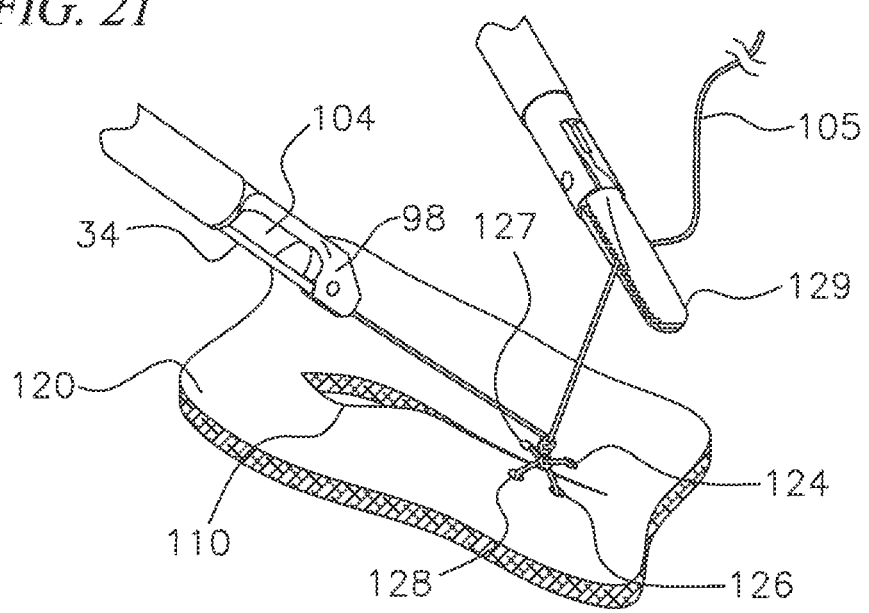
FIG. 21 shows both the suturing instrument of FIG. 1 and a surgical grasper pulling on either ends of the suture to lock the knot in place to secure the wound closure.

Now referencing FIGS. 18A-21, FIG. 18A shows the instrument 16 with the distal tail of the suture 105 exposed and the distal tip 98 of the instrument 16 ready for knot tying. FIGS. 18A 19B show the first throw of the knot tying process. FIGS. 19C-19F show the second throw of the knot tying process. FIGS. 21 and 22 show the cinching down of the knot. In FIG. 18B, a surgical grasper 129, is used to grab the free end of the suture 105 and to wrap the suture 105 around the tissue bite area 104 of the instrument 16. Note that to construct this knot, which we have named the "Super Surgeon's knot," the first wrapping of suture 105 around the tissue bite area 104 consists of two complete loops wrapped around the tissue bite area 104. FIG. 18C shows the advancement of the needle 34, ferrule 103 and suture 105 back into its ferrule compartment 107, best shown in FIG. 18A, after the double wrap has been placed around the tissue bite area 104 of the instrument 16. FIG. 18D shows the now stripped ferrule 103 in its ferrule compartment 107. FIG. 18E shows the knot forming double loops being slid down towards the wound closure site 110. FIG. 19A shows the grasper 129 further cinching the knot down to the wound closure site 110. FIG. 19B shows the suture 105 now fully retracted back on its needle 34 to further expose the tissue bite area 104 of the knot tying instrument 16. FIG. 19C shows a second wrapping of a single loop placed around the distal tip 98 of the instrument 16 to secure the knot. FIG. 19D shows the needle 34 again advanced to replace the ferrule 103 in its ferrule compartment 107 along with the suture 105. FIG. 19E shows the ferrule 103 in its ferrule compartment 107 with the needle 34 and ferrule stripper 35 now back. FIG. 19F shows the second throw, a single loop throw, of the Super Surgeon's knot being slid over the ferrule 103 and suture 105 down towards the wound closure 110. FIG. 20D illustrates that by pulling on the surgical grasper 129 on the free end of the suture 105, the suture loops are further slid towards and down onto the wound closure 110 to begin to pull (also called approximate or appose) the edges of the wound 110 together, but not fully locking the knot in place. FIG. 21 shows by pulling on the surgical grasper 129 holding the free end of the suture 105, and now by simultaneously pulling on instrument 16 holding the ferrule 103 end of the suture 105, both ends of the suture 105 are drawn tight, thereby locking the Super Surgeon's knot in place. The distinct advantage of the Super Surgeon's knot is that it permits the user to place the knot above the wound closure and appropriately appose the wound edge by pulling only on the free end of the suture, and then, once the correct tissue apposition is achieved, the user can pull on the ferrule end of the suture to lock the knot down. Locking down the Super Surgeon's knot alone provides adequate holding force, at least temporarily, to hold together many types of wound closures. For example, a Super Surgeon's knot made with 2-0 STRONGSORB® suture by LSI SOLUTIONS, Inc., achieves an average tissue holding strengths of approximately 0.5 kg knot holding force to temporarily secure and tissue edges together. Subsequent throws on top of the Super Surgeon's knot will add additional knot holding force up to the native strength of the suture (e.g., with 2-0 STRONGSORB®, up to 5 to 6 kg tensile pull).

Figure 22A:
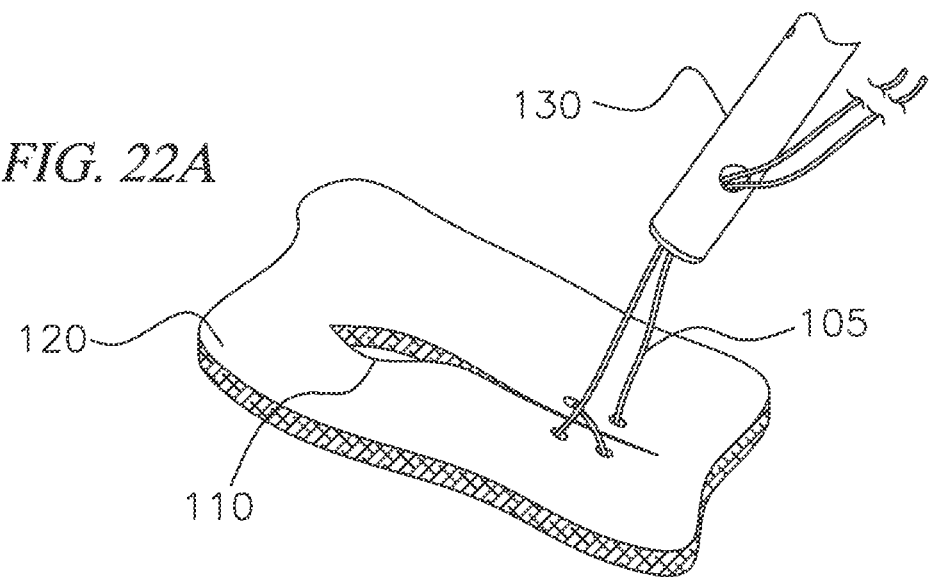
FIGS. 22A-22C show an alternate method of securing the ends of the suture used in the suturing procedure illustrated in FIGS. 14A-17D by crimping a sleeve member over the ends of the suture.
Figure 22B:
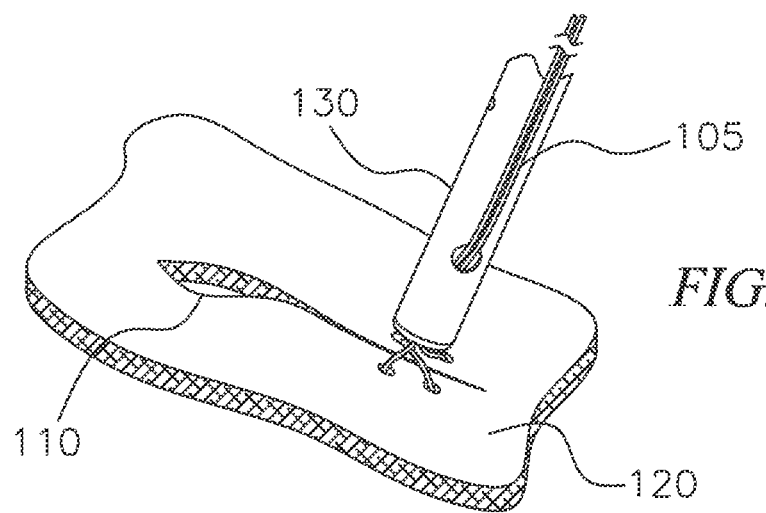
Figure 22C:
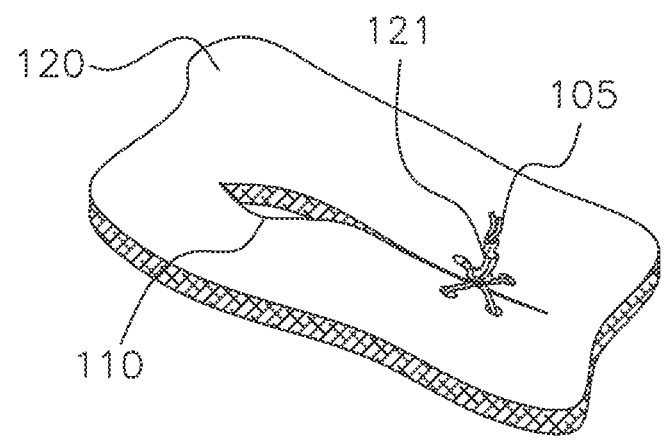

FIGS. 22A-22C illustrate an alternate method of securing the free ends of the suture 105 left by the instrument 16, used to close the wound 110 in the tissue 120. FIG. 22A represents an instrument 130, which crimps a sleeve member 121 to secure suture 105 together and is commercially available as a Ti-KNOT® Device manufactured by LSI SOLUTIONS, Inc., under at least the following U.S. Pat. Nos. 5,520,702; 5,643,289 and 5,669,917. The free ends of the suture 105 are passed through the instrument 130 and the instrument 130 is passed closer to the wound closure 110. FIG. 22B illustrates the instrument 130 being applied directly to the wound closure 110 and both free ends of the suture 105 drawn tight, removing any slack and drawing the opposing sides of the wound closure 110 closer together. FIG. 22C shows the sleeve member 121 crimped around the suture 105 at the wound closure 110. Note that the suture 105 has been trimmed.

After using instrument 16 to place suture 105 for running a wound closure 110, one or both ends of the suture 105 may remain unsecured. These free ends of the suture 105 can be attached to pledgets or bolsters 122a and 122b to prevent their ability to be pulled into or away from the wound site 110. A pledget is typically a pliable, non-reactive piece of material, such as polyester mesh, Gortex®, or the like, that is often used in conjunction with sutures or staples to augment wound closures. In this example, a bolster 122a is attached (e.g., by tying or sewing) to one end of an additional segment of suture 123a. By placing the free end of this bolstered suture 123a, along with one free end of the suture 105, the bolster 122a and its attached suture 123a can be passed down using suture 105 as a guide. Bolster 122a, suture 123a and one end of suture 105 can be secured at one end of the wound site 110 with a sleeve member 121. The bolster 122a can hold this end of the running suture 105 from being pulled into the wound 110. By repeating a similar bolstered suture 123b placement at the opposite end of the wound 110, the second bolster 122b and its suture 123b can hold the second suture 105 end from being pulled into the wound 110. Bolsters 122a and 122b secured at each end of the wound 110, prevent the suture 105 from being pulled out of the wound 110 from either direction.

FIGS. 24A-24C illustrate a second example. The main difference between this example and the first example, is that instead of stripping the ferrule 103 with the ferrule stripper 35 traversing the gap and engaging the ferrule 103, the member that directly contacts the ferrule 103 for ferrule stripping is incorporated in the distal tip 98. The thumb button 41e drive mechanism for this example can be the same as in the first example. FIG. 24A shows a perspective of the distal jaw, which looks similar to the first example, except instead of a slope to direct the stripper wedge 131 towards the ferrule, the stripper wedge 131 enters a chamber 141 and subsequently wedges member 133 against ferrule 103 to permit removal of the needle 34. FIG. 24B shows needle 34 engaging ferrule 103 in ferrule compartment 107 with the stripper wedge 131 traveling toward chamber 141. FIG. 24C shows the ferrule 103 held in its ferrule compartment 107 by stripper wedge 131 forcing over member 133. Needle 34 can now be extracted from ferrule 103. Stripper wedge 131 can be subsequently withdrawn leaving the ferrule 103 in it reloaded position.

FIGS. 25A-25C illustrate another example. In this example, unlike the prior two, the ferrule stripping element does not traverse the gap in the distal tip 98. Rather, in this example, the stripper wedge 131, which can be a semi-flexible material, such as memory metal, Nitinol, or the like, passes through a channel in the bridge that traverses behind the gap in the jaw. This ferrule stripping example can also be advanced towards the ferrule using a mechanism similar to the already described thumb slide mechanism 41 (FIG. 3). FIG. 25A shows needle 34 after being retracted back and stripped off ferrule 103 held in its ferrule compartment 107 by the flexible integrated stripper 135. FIG. 25B is a partial sectional view of needle 34 engaging ferrule 103 in its ferrule compartment 107. The flexible integrated stripper 135 is shown retracted into the bridge channel 134 to permit the needle 34 to pull the ferrule 103 out of its ferrule compartment 107. FIG. 25C illustrates a partially retracted needle after its ferrule 103 is stripped by the flexible integrated stripper 135.

FIGS. 26-30J describe a further example. Unlike the previous three examples, this fourth version does not require an additional manual mechanism, like the thumb slide mechanism, to enable ferrule stripping. Instead of pushing a button to activate a stripper, this instrument is more automated to enable stripping the ferrule 103 imply squeezing the lever 36a a second time.

Figure 26:
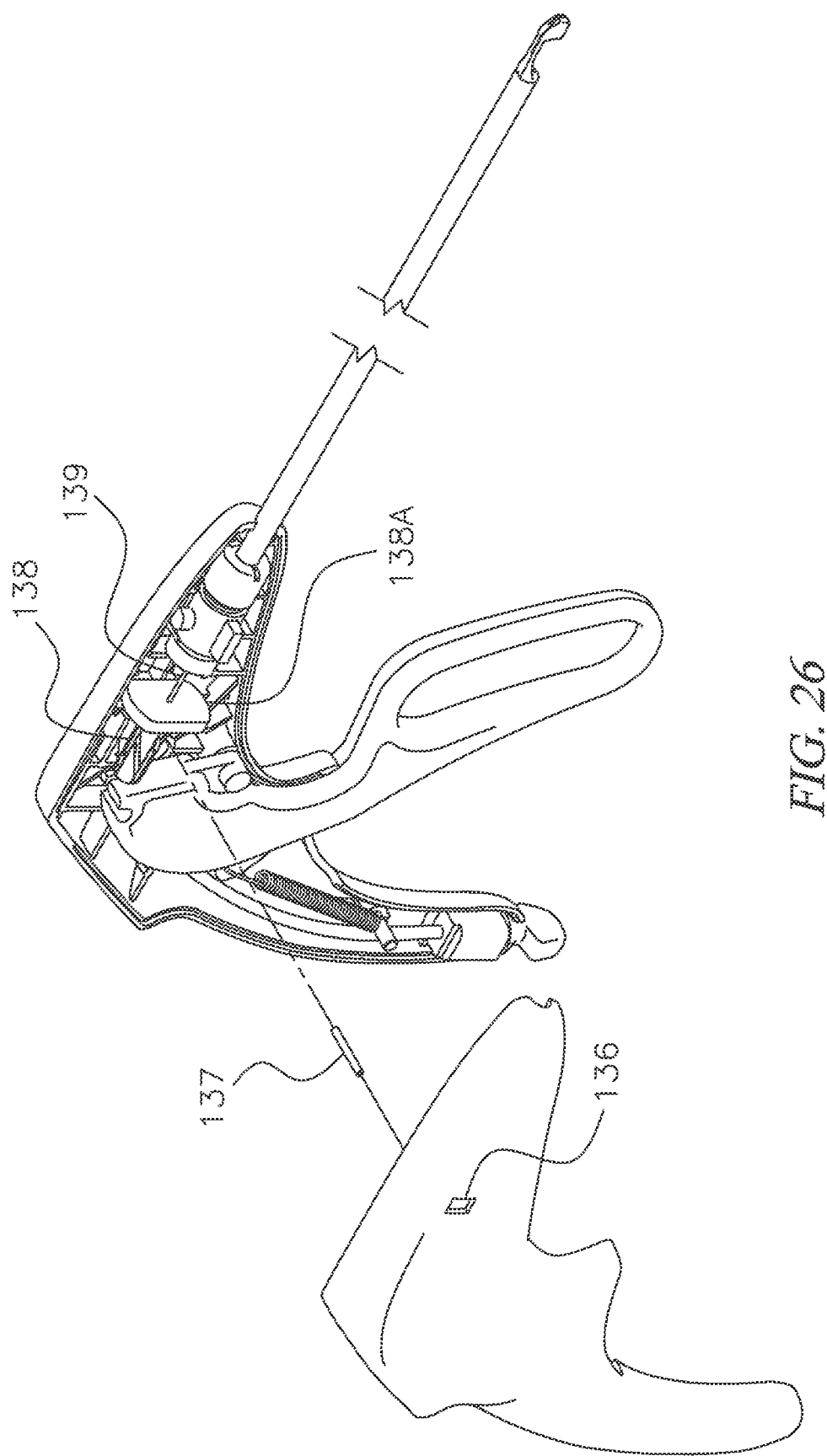
FIG. 26 is a partially exploded isometric view of the fourth example of the tissue suturing instrument of FIG. 1 in which a cam and follower mechanism and faceted needle are utilized to allow for automatic ferrule pick-up and release.

FIG. 26 shows this instrument in a perspective view illustrating window 136 in the right handle half; a comparable window (not shown) is located in the opposite location on the left handle half. These windows permit an instrument user to view from either handle an asymmetric rotating disc 138a that indicates whether the cam needle 139 is in the stripper or non-stripper orientation. Also, note rod 137 mounts into the right handle half to engage the slots in the rotating cam 138. When lever 36a rotates back, cam 138 drives forward, lifts towards the mid stroke, then lowers and rotates about rod 137, as seen in FIGS. 27A-27C.

FIG. 27A shows the rod 137 engaging the distal slot in cam 138. The rotating indicator disc 138a is vertically oriented indicating a non-faceted edge of the cam needle 139 faces the ferrule latch 140 (FIG. 27A; also see FIGS. 28-31J). Release of the lever 36a permits the cam needle 139 and its rotational cam 138 to travel back and elevates slightly at mid stroke, where rod 137 enters an obliquely oriented slot, to begin rotating the rotational cam 138 and its attached cam needle 139 (FIG. 27E). By completion of the lever 36a, the full rotation of the rotational cam 138 (FIG. 27A), the needle facet 139b (FIG. 27F) is now oriented towards the ferrule latch 140, which permits ferrule stripping.

Figure 28:
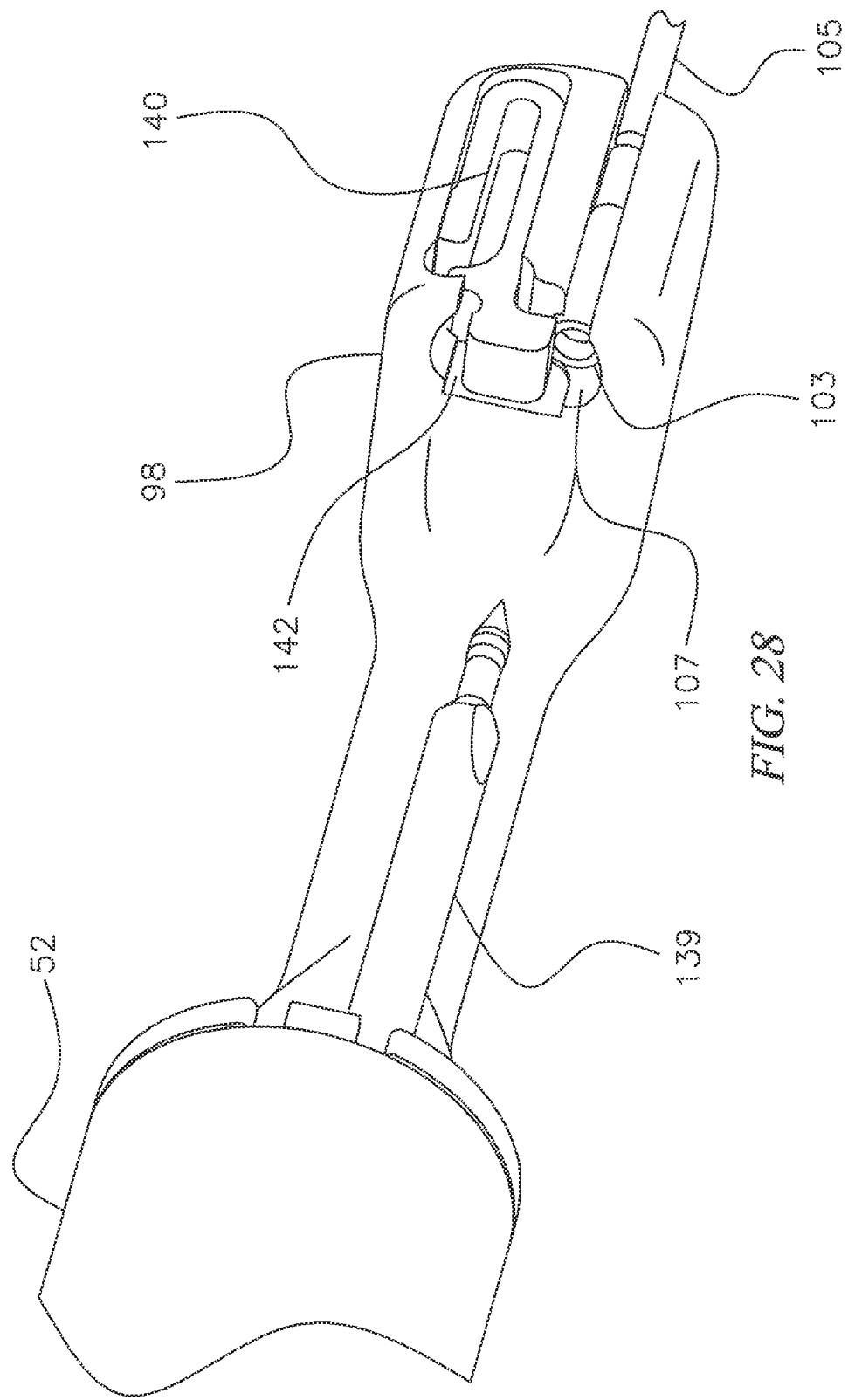
FIG. 28 is a close-up perspective view of the distal tip of the fourth example of the tissue suturing instrument of FIG.

FIG. 28 shows the partially retracted cam needle 139 having its ferrule 103 held by ferrule latch 140. Note this illustration shows a pocket 142 recessed in the distal tip 98 for holding the ferrule latch 140.

FIG. 29A shows cam needle 139 oriented with a non-faceted shoulder 139c engaging and lifting the ferrule engaging surface 140g of the ferrule latch 140. The ferrule 103 is not held by the ferrule latch 140, because the ferrule 103 latch 140 is compressed by the non-faceted shoulder 139c pushing against timing surface 140b. The ferrule 103 is able to be pulled from its ferrule compartment 107 by cam needle 139. FIG. 29B shows the distal end of the fourth example with cam needle 139 retracting back through the gap and the ferrule latch 140 engaging into the proximal edge of ferrule 103. FIG. 29B highlights cam needle 139 oriented to have a facet 139b towards the ferrule latch 140, to not engage timing surface 140b so that the ferrule engagement surface 140g contacts the proximal edge of ferrule 103. Surfaces 140f and 140e provide contacts to help maintain latch placement in its pocket 142.

FIGS. 30A-30J show one complete cycle of the cam needle 139 traversing the tissue bite area 104, picking up a ferrule 103, the ferrule 103 being returned to its ferrule compartment 107 and the ferrule 103 being stripped by the ferrule latch 140. This cycle reloads the ferrule 103 for another stitch placement. FIG. 30 shows the retracted cam needle 139 oriented with a non-faceted shoulder 139c facing the ferrule latch 140, which secures the ferrule 103 with its suture 105 in its ferrule compartment 107 in the distal tip 98. FIG. 30B shows cam needle 139 fully advanced into ferrule 103, with its non-faceted shoulder 139c compressing ferrule latch 140. FIG. 30C shows cam needle 139 pulling ferrule 107 and suture 105 back beyond the compressed ferrule latch 140. At approximately the midpoint of the cam needle 139 retraction, cam needle 139 begins its rotation with ferrule 103 and suture 105 rotating with cam needle 139. FIG. 30E shows cam needle 139 along with its ferrule 103 and suture 105 fully retracted back with its 900 rotation completed. FIG. 30F shows cam needle 139, ferrule 103 and suture 105 advancing back into ferrule compartment 107. A faceted shoulder 139a of cam needle 139 now faces the ferrule latch 140. FIG. 30G shows the cam needle 139, ferrule 103 and suture 105 fully placed back into its ferrule compartment 107. The faceted shoulder 139a of cam needle 139 does not cause ferrule latch 140 to compress up or deflect away from the proximal edge of ferrule 103. FIG.

30H shows the retraction of ferrule 103 stopped by ferrule latch 140, stripping ferrule 103 from its partially retracted cam needle 139. FIG. 30J shows the cam needle 139 now fully retracted back and rotated back 180.degree. so that the opposite side of the non-faceted shoulder 139c is oriented towards the ferrule latch. The ferrule 103 is reloaded back into its ferrule compartment 107 and cam needle 139 is ready to advance through more tissue 120, picking up ferrule 103 and pulling it along with its suture 105 back through another bite of tissue 120.

FIG. 31 illustrates a perspective view of one embodiment of an improved surgical suturing device 150. This embodiment of a sewing device 150 has a needle (not visible in this view) actuated by a handle 152 which is moveable relative to a housing 154 in a similar manner to the previous suturing device examples. A shaft 156, having a proximal end 158 and a distal end 160 is coupled to the housing 154 near the proximal end 158 of the shaft 156. A suturing guide tip 162 is coupled to the distal end 160 of the shaft 156. The needle (not visible in this view) may be actuated to traverse a tissue bite area 164 defined by the guide tip 162, to pick up a ferrule held in a ferrule pocket (also not visible in this view) in the distal end 166 of the guide tip 162. Those skilled in the art will realize that other embodiments may utilize other mechanisms for actuating the needle back and forth across the tissue bite area 164, for example, but not limited to an actuator utilizing: a rack and pinion feature, one or more gears, a solenoid, a motor, a slideable control, a rotatable control, or any combination or plurality thereof.

In the embodiment of FIG. 31, the shaft 156 has a bent portion 168 which is intended to make it easier for a surgeon holding the device 150 by the housing 154 to see the guide tip 162 past the shaft 156 and the housing 154. The angle created by the bent shaft 156 is apparent from a comparison of the orientation of a first longitudinal axis 170 of a proximal portion of the shaft 156 to the orientation of a second longitudinal axis 172 of the distal portion of the bent shaft. The illustrated angle of the bent shaft 156 is merely one example of a suitable angle, and greater or lesser angles for a bent shaft may be suitable for different embodiments. Other embodiments may not include a bend in the shaft 156. Still other embodiments may have a flexible shaft or otherwise present the shaft with the ability to effectively bend so that the guide tip 162 may be angled relative to the first longitudinal axis 170 as shown in this embodiment. Embodiments with a bend 168 in shaft 156 enable a surgeon to view the guide tip 162 at the distal end of the device 166 more easily in minimally invasive scenarios.

FIGS. 32A and 32B are enlarged perspective views of the guide tip 162 shown from differing perspectives so that the features of the guide tip 162 may be more fully explained. A ferrule holder 174 is located on the distal end 166 of the device and is aligned with the shaft 156 where the reciprocating needle (as actuated by the handle, for example as described in previous examples) can exit 176. This distal end 166 and the path that will be traversed by the needle, however, are visible from the operator's point of view because the distal end 166 is supported by framing arms 178, 180 which define a viewing port 182 to the tissue bite area 164 and the ferrule holder 174 in the distal end. As can be seen more clearly from the view of FIG. 32A, the viewing area 182 may be considered to be defined from a first orientation (for example, from the top of the guide tip), while the tissue bite area 164 may be considered to be defined from a second orientation (for example, from the side of the guide tip) by the proximal end 165 of the guide tip, the framing arms, 178, 180, and the distal end 166 of the guide tip.

FIGS. 33A and 33B are top and side views, respectively, of the guide tip, illustrating that the needle path 184 in the shaft and the ferrule holder 174 are aligned with each other. From the top view, of FIG. 33A, it can also be seen that the needle path 184 is aligned substantially centrally with a plane 186 defined by the first longitudinal axis 170 and the second longitudinal axis 172 (shown in FIG. 31). Furthermore, the plane 186 is substantially centered between the framing arms 178 and 180 to enable improved visualization of the needle path, as the needle can be expected to traverse the tissue bite area on a line centered between the framing arms 178, 180 when viewed from the top view of FIG. 33A or similar views. Furthermore, it should be noted when comparing the different views of FIGS. 33A and 33B that the viewing port 182 defined by the framing arms 178, 180 is substantially perpendicular to the tissue bite area 164 in this embodiment. Furthermore, the viewing port 182 may be considered to be substantially perpendicular to the plane 186 in which the first and second longitudinal axes 170, 172 lie.

FIG. 34 is an exploded view of the device tip of FIG. 32A. A needle 188 is slidable within the shaft 156. The needle 188 passes through and selectively out of a needle guide 190 in the guide tip 162. The distal end 166 of the guide tip has a first spring 192 which cooperates with the needle 188 to allow the needle first to remove the ferrule 194 attached to the suture 196 that is held by a ferrule holder in the guide tip, drawing it back across the tissue bite area and into the proximal end of the guide tip, and then, to return the ferrule to the distal end of the guide tip, leaving it there for another cycle, similar to examples discussed above for FIGS. 1-30J. Some examples may also have a second releasing spring 198 which rides along the needle 188 inside the guide tip on the proximal side of the guide tip. In normal operation, the ferrule, when coupled to the needle tip will not engage the second releasing spring 198. However, when the device handle is pushed backward beyond its normal limit, the second releasing spring 198 will push the ferrule off of the needle tip, making the end of the suture available to the surgeon for further steps, such as trimming and knotting.

Figure 35A:
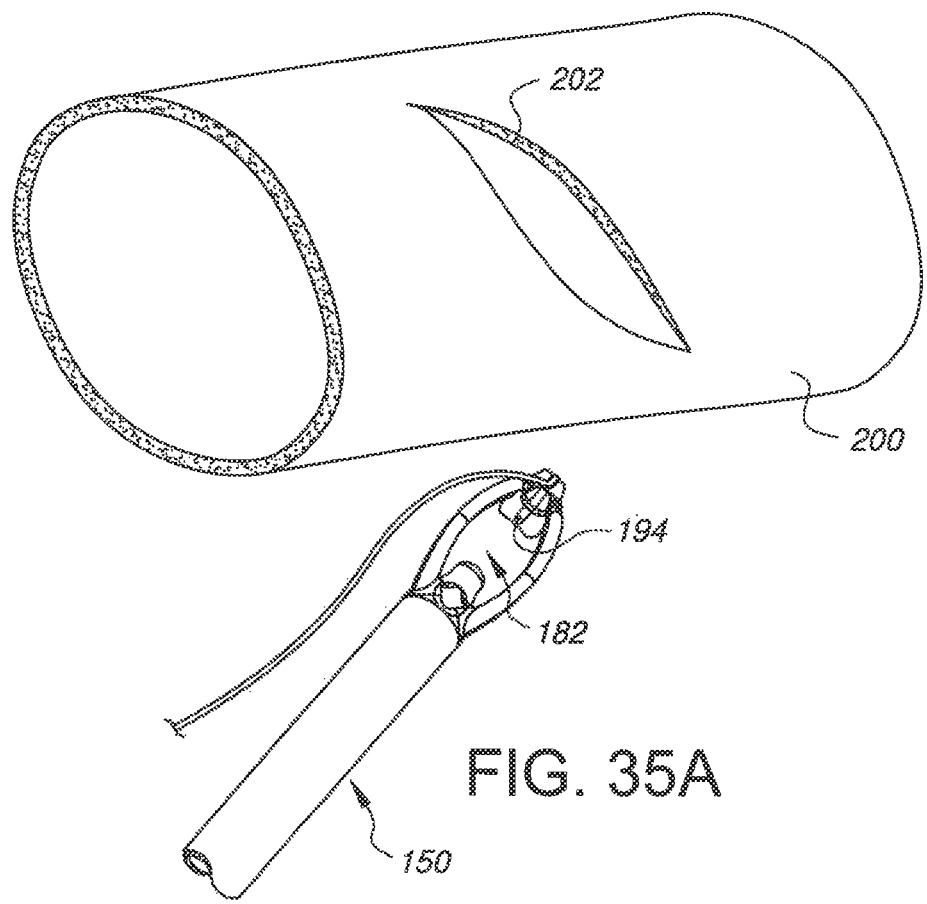
Figure 35B:
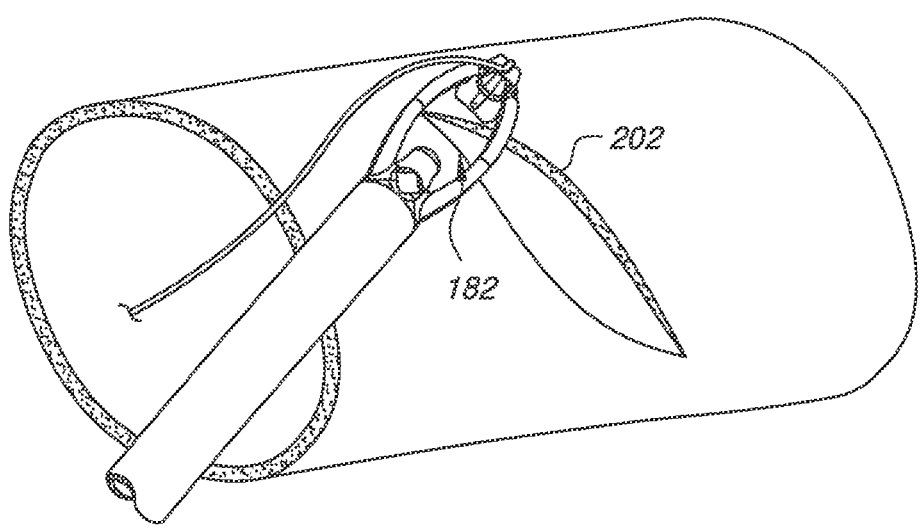
Figure 35C:
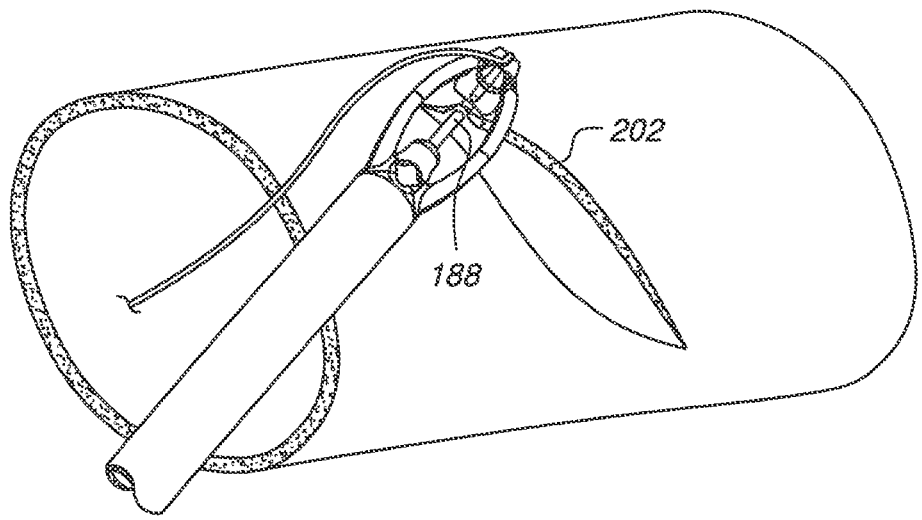
Figure 35D:
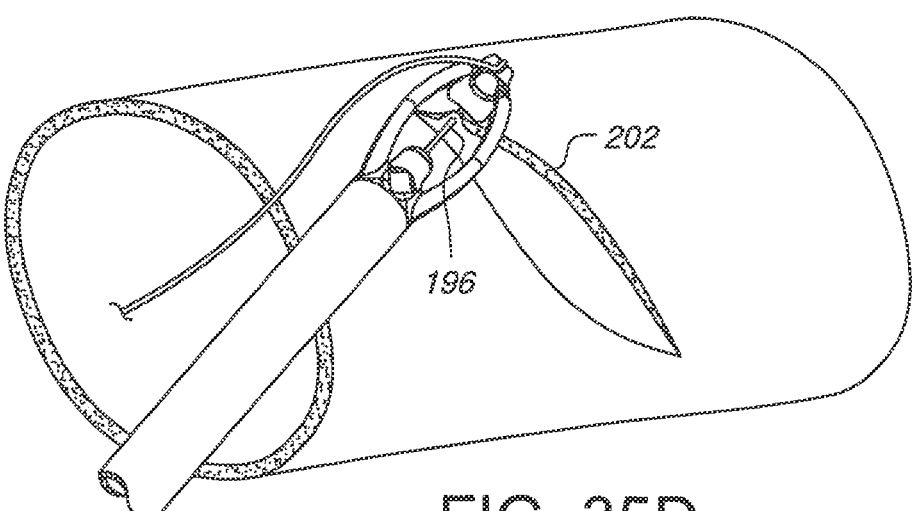
Figure 35E:
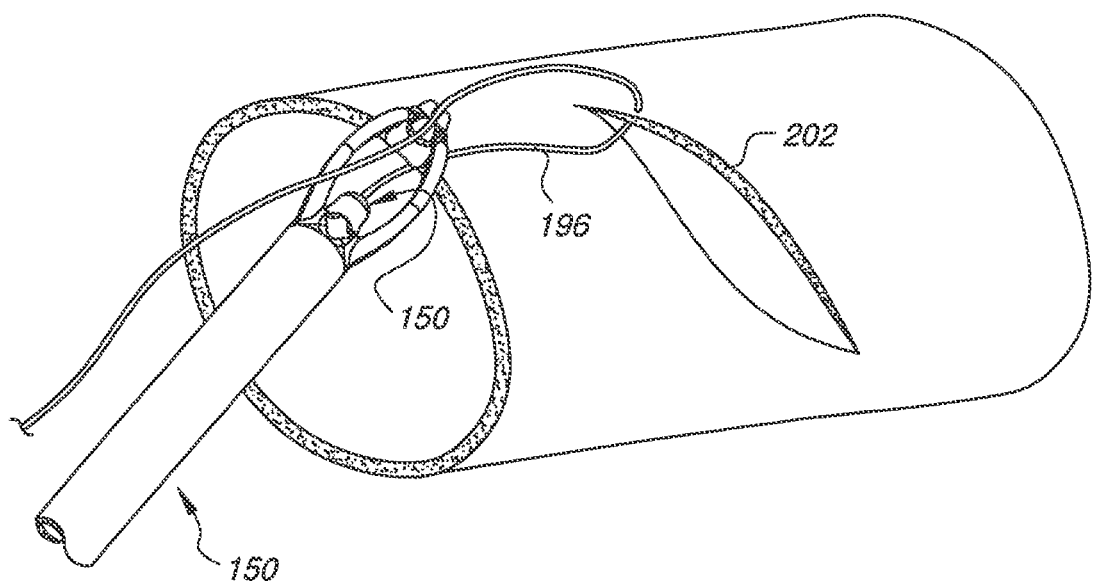
Figure 35F:
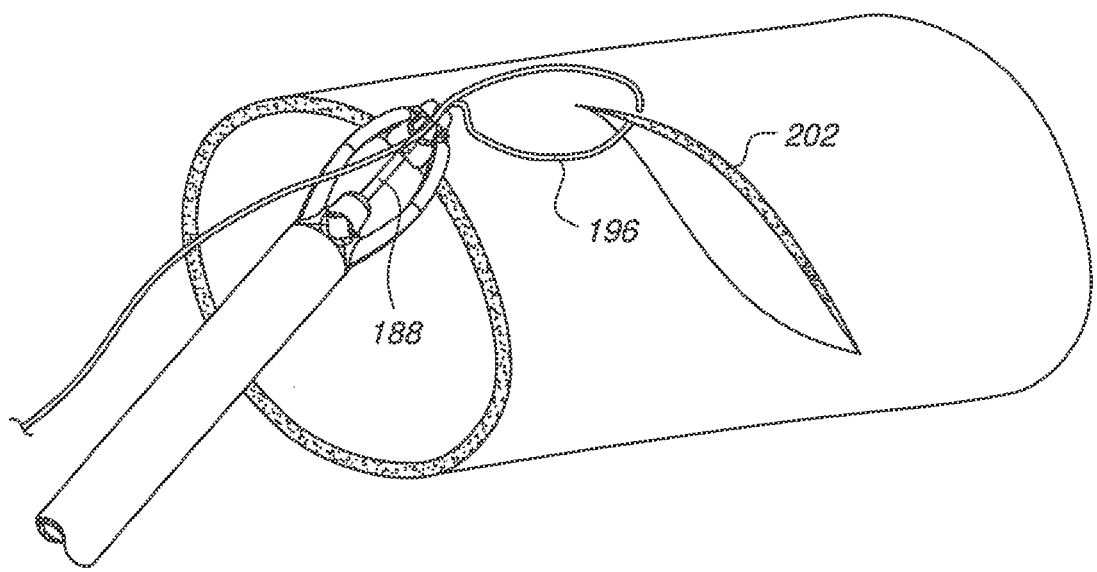
Figure 35G:
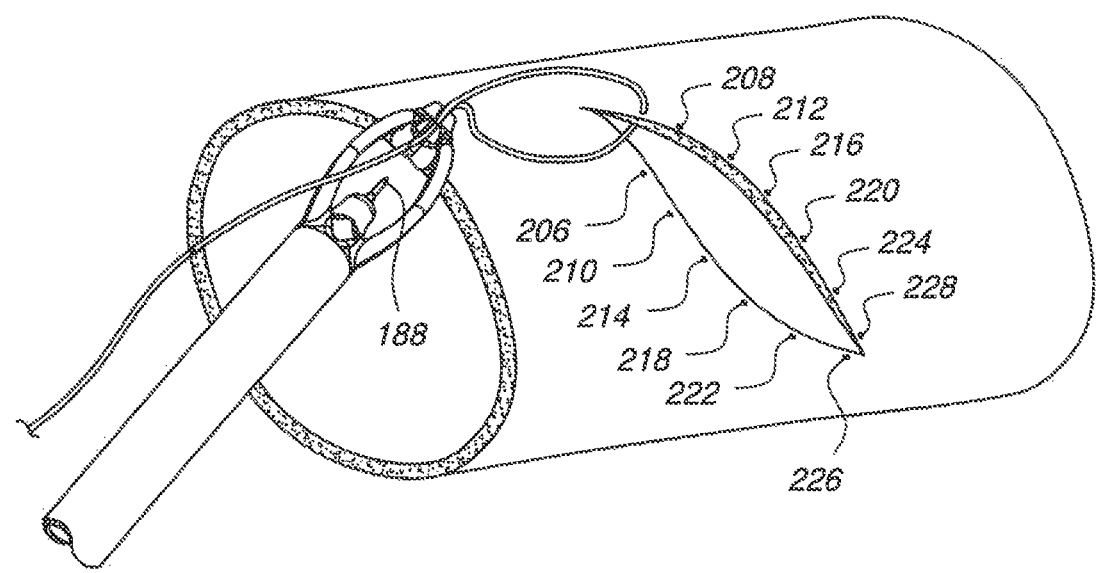
Figure 35H:
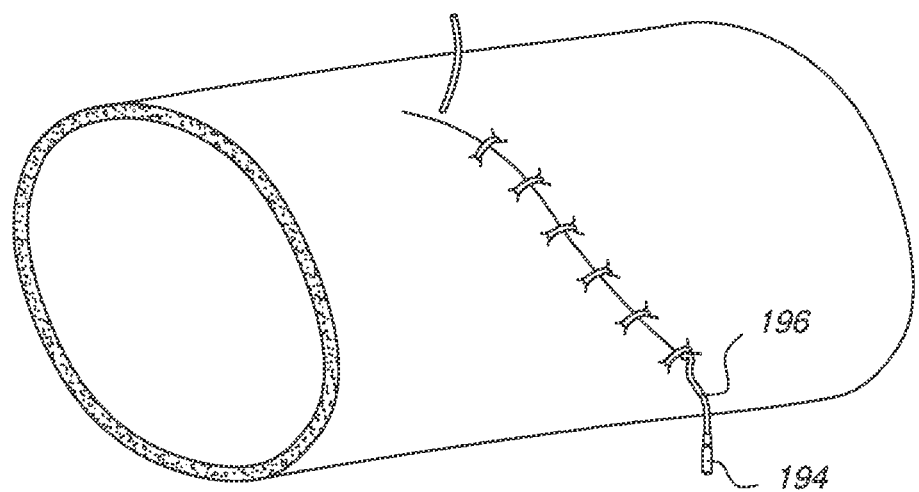

FIGS. 35A-35H schematically illustrate the operation of the embodied device of FIG. 32A. In FIG. 35A, a vessel 200 has an incision 202 in need of closure. One non-limiting example of such a vessel is an aorta that has had an aortotomy. The surgical suturing device 150 stands ready, with the suture ferrule 194 in the distal end of the device. The surgeon has the device positioned so that a direct view or a view provided by an imaging device, such as an endoscope or laparoscope allows the surgeon to see through the viewing port 182 of the device. In FIG. 35B, the tissue bite area of the device is placed over one side of the incision 202. Alignment can easily be seen through the viewing port 182 defined in the device. In FIG. 35C, the needle 188 is advanced from the shaft towards the distal end of the device. The needle passes through the tissue in the tissue bite area and engages the suture ferrule. In FIG. 35D, the needle has been retracted, pulling the ferrule and the associated suture 196 back through the tissue in a proximal direction. As illustrated in FIG. 35E, the device 150 may be pulled away from the incision 202. At this stage, the suture is free to disengage from the distal end of the device, but still remains coupled to the ferrule held by the needle inside the proximal end 204 of the device tip. FIG. 35F shows the needle 188 being advanced back across the tissue bite area to the distal end where the ferrule is returned to the ferrule holder. The first release spring engages the ferrule to hold it in the distal end as the needle 188 is then retracted again to the proximal end of the guide tip as illustrated in FIG. 35G. Note that the needle 188 is not yet fully retracted in the view of FIG. 35, but that the needle, when fully retracted will no longer be visible, similar to the starting point of FIG. 35A. The process of FIGS. 35B-35G can be repeated at multiple locations along the incision, for example, locations 206, 208, 210, 212, 214, 216, 218, 220, 222, 224, 226, 228 (non-limiting examples), and then the ferrule can be released from the device, resulting in a sutured incision as illustrated in FIG. 35H. At this point, the ferrule may be trimmed from the suture, and the suture ends may be tied off by any desired means.

The sewing device can be used for other types of closures, including for taking a bite of both sides of the incision in a single pass. A single suture may be used, or multiple sutures may be used, for example, when starting stitches from each end which will meet in the middle of the incision. The improvements in usability made possible by the centrally aligned viewing port provide greater accuracy for a surgeon when placing stitches.

Various advantages of a minimally invasive surgical suturing device with improved visualization have been discussed above. Embodiments discussed herein have been described by way of example in this specification. It will be apparent to those skilled in the art that the forgoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and the scope of the claimed invention. Additionally, the recited order of processing elements or sequences, or the use of numbers, letters, or other designations therefore, is not intended to limit the claims to any order, except as may be specified in the claims. Accordingly, the invention is limited only by the following claims and equivalents thereto.

What is claimed is:

1. A suturing device, comprising:
   a) a guide tip having:
      1) first and second framing arms that define a viewing port from a first orientation; and
      2) proximal and distal ends of the guide tip which, with the first and second framing arms, define a tissue bite area from a second orientation;
   b) a ferrule holder located in the distal end of the guide tip and centered relative to the first orientation; and
   c) a needle movable within and circumferentially rotatable relative to the guide tip along a path through the tissue bite area, circumferentially rotatable, and centrally viewable in the viewing port relative to the first orientation; and
   d) a ferrule removal spring in the distal end of the guide tip.

2. The suturing device of claim 1, wherein the first and second orientations are substantially perpendicular to each other.

3. The suturing device of claim 1, wherein the first and second framing arms are symmetrical.

4. The suturing device of claim 1, further comprising a ferrule releasing spring in the proximal end of the guide tip.

5. The suturing device of claim 1, further comprising:
   a ferrule held by the ferrule holder; and
   a suture coupled to the ferrule.

6. The suturing device of claim 1, further comprising a shaft having a proximal and a distal end, wherein the guide tip is coupled to the distal end of the shaft and the needle is movable within the shaft.

7. The suturing device of claim 6, wherein the shaft comprises a bend such that:
   the shaft has a first longitudinal axis on one side of the bend and a second longitudinal axis on a second side of the bend; and
   the first longitudinal axis and the second longitudinal axis lie in a plane which is substantially perpendicular to the viewing port.

8. The suturing device of claim 6, wherein the shaft comprises a bend such that:
   the shaft has a first longitudinal axis on one side of the bend and a second longitudinal axis on a second side of the bend; and
   the first longitudinal axis and the second longitudinal axis lie in a plane which is substantially centered in the viewing port.

9. The suturing device of claim 6, wherein the shaft is flexible.

10. The suturing device of claim 1, wherein the tissue bite area is visible through the viewing port.

11. A suturing device, comprising:
   a) a shaft having a proximal and a distal end, wherein the shaft comprises a bend such that the shaft has a first longitudinal axis on one side of the bend and a second longitudinal axis on a second side of the bend;
   b) a guide tip coupled to the distal end of the shaft, the guide tip having:
      1) first and second framing arms that define a viewing port such that the first longitudinal axis and the second longitudinal axis lie in a plane which is substantially centered in the viewing port; and
      2) proximal and distal ends of the guide tip which, with the first and second framing arms, define a tissue bite area which is visible through the viewing port;
   c) a ferrule holder located in the distal end of the guide tip; and
   d) a needle movable within and circumferentially rotatable relative to the guide tip along a path through the tissue bite area, circumferentially rotatable, and centrally viewable in the viewing port; and
   e) a ferrule removal spring in the distal end of the guide tip.

12. The suturing device of claim 11, wherein the first and second framing arms are symmetrical.

13. The suturing device of claim 11, further comprising a ferrule releasing spring in the proximal end of the guide tip.

14. The suturing device of claim 11, further comprising:
   a ferrule held by the ferrule holder; and
   a suture coupled to the ferrule.

15. The suturing device of claim 11, wherein the shaft is flexible.

16. A suturing device, comprising:
   a guide tip defining a viewing port and a tissue bite area;
   a needle movable within and circumferentially rotatable relative to the guide tip along a path through the tissue bite area, circumferentially rotatable, and centrally viewable in the viewing port; and
   a ferrule removal spring in the distal end of the guide tip.

17. The suturing device of claim 16, wherein the viewing port and the tissue bite area are substantially orthogonal to each other.

18. The suturing device of claim 16, further comprising a ferrule holder.

\* \* \* \* \*